United States Patent
Fuksova et al.

(10) Patent No.: US 7,816,350 B2
(45) Date of Patent: Oct. 19, 2010

(54) SUBSTITUTED [1,2,3] TRIAZOLO[4,5-D]PYRIMIDINES AS CDK INHIBITORS

(75) Inventors: Kveta Fuksova, Praha (CZ); Libor Havlicek, Praha (CZ); Vladimir Krystof, Ostrava (CZ); Rene Lenobel, Frydek Mistek (CZ); Miroslav Strnad, Olomouc (CZ)

(73) Assignees: Institute of Experimental Botany ASCR, Lysolaje (CZ); Univerzita Palackeho v Olomouci, Olomouc (CZ)

( * ) Notice: Subject to any disclaimer, the term of this patent is extended or adjusted under 35 U.S.C. 154(b) by 1422 days.

(21) Appl. No.: 11/051,059

(22) Filed: Feb. 4, 2005

(65) Prior Publication Data

US 2006/0035909 A1  Feb. 16, 2006

Related U.S. Application Data

(63) Continuation of application No. PCT/IB03/04188, filed on Aug. 22, 2003.

(30) Foreign Application Priority Data

Aug. 23, 2002  (GB) ............................ 0219746.5

(51) Int. Cl.
| | |
|---|---|
| C07D 487/04 | (2006.01) |
| A61K 31/519 | (2006.01) |
| A61P 35/00 | (2006.01) |
| A61P 25/28 | (2006.01) |
| A61P 17/06 | (2006.01) |
| A61P 3/10 | (2006.01) |
| A61P 13/12 | (2006.01) |
| A61P 37/02 | (2006.01) |
| A61P 31/20 | (2006.01) |
| A61P 31/22 | (2006.01) |

(52) U.S. Cl. ..................... 514/234.5; 514/252.16; 514/261.1; 544/118; 544/254

(58) Field of Classification Search ................ 544/254, 544/118; 514/261.1, 234.5, 252.16
See application file for complete search history.

(56) References Cited

U.S. PATENT DOCUMENTS

| | | | |
|---|---|---|---|
| 5,866,702 A | | 2/1999 | Mackman et al. |
| 6,107,301 A | | 8/2000 | Aldrich et al. |
| 6,458,796 B1 | * | 10/2002 | Haning et al. ............ 514/261.1 |
| 7,034,032 B2 | * | 4/2006 | Brown et al. ............ 514/261.1 |

FOREIGN PATENT DOCUMENTS

| | | |
|---|---|---|
| EP | 1142893 A1 | 10/2001 |
| JP | 59-62595 | 4/1984 |
| JP | 59-062595 * | 4/1984 |
| WO | WO-97/20842 A1 | 6/1997 |
| WO | WO-97/35539 A2 | 10/1997 |
| WO | WO-97/35846 A1 | 10/1997 |
| WO | WO-98/28300 A1 | 7/1998 |
| WO | WO-99/05143 A1 | 2/1999 |
| WO | WO-99/41254 A1 | 8/1999 |

OTHER PUBLICATIONS

Baindur et. al. (J. comb. Chem., 2003, 5, 653-659).*
Shealy et. al. (J. Org. Chem., 1961, 26, 4433-4440).*
Ashton, Wallace T., et al., "Synthesis and Antiherpetic Activity of (±)-9[[(Z)-2- (Hydroxymethyl)cyclopropl]methyl]guanine and Related Compounds," *J. Med. Chem.*, vol. 31:2304-2315 (1988).
Beauchamp, Lilia M., et al., "Modifications on the Heterocyclic Base of Acyclovir: Syntheses and Antiviral Properties," *J. Med. Chem.*, vol. 28:982-987 (1985).
Chorvat, Robert J., et al., "Synthesis Corticotropin-Releasing Factor Receptor Binding Affinity, and Pharmacokinetic Properties of Triazolo-, and Pyrrolopyrimidines and -pyridines," *J. Med. Chem.*, vol. 42:833-848 (1999).
Shealy, Y. Fulmer, et al., "v-Triazolo[4,5-d]pyrimidines. I. Synthesis and Nucleophilic Substitution of 7- Chloro Derivatives of 3-Substituted v-Triazolo[4,5-d]pyrimidines," *The Kettering-Meyer Laboratory, Southern Research Institute*, (1961).
Shealy, Y. Fulmer, et al., "v-Triazolo[4,5-d]pyrimidines. III. N-(3-Alkyl-5-amino-3H-v-triazolo[4,5-d ]pyrimidin-7-yl) -amino Acids," *Kettering-Meyer Laboratory, Southern Reserach Institute*, (1966).

* cited by examiner

*Primary Examiner*—James O Wilson
*Assistant Examiner*—Susanna Moore
(74) *Attorney, Agent, or Firm*—Lahive & Cockfield, LLP; Cynthia L. Kanik; Brian C. Trinque

(57) ABSTRACT

The present invention relates to a compound of formula I, or a pharmaceutically acceptable acid salt thereof.

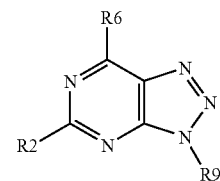

The invention further relates to the use of such compounds in the treatment of hyperproliferative skin disorders, viral infections, cancer, rheumatoid arthritis, lupus, type I diabetes, multiple sclerosis, restenosis, polycystic kidney disease, graft rejection, graft versus host disease and gout, or for psoriasis, parasitoses such as those caused by fungi or protists, or Alzheimer's disease.

Further aspects of the invention relate to the use of such compounds in the inhibition of cell proliferation, in the induction of apoptosis, to modulate the activity of adrenergic and/or purinergic receptors or to suppress immunostimulation. The invention also relates to the use of 2,6,9-trisubstituted 8-azapurines in maintaining mammalian ooctyes at the germinal vesicle stage.

8 Claims, 2 Drawing Sheets

SUBSTITUTED [1,2,3] TRIAZOLO[4,5-D]PYRIMIDINES AS CDK INHIBITORS

RELATED APPLICATIONS

This application is a continuation of PCT/IB2003/004188, filed on Aug. 22, 2003, which claims priority to GB 0219746.5, filed on Aug. 23, 2002. The entire contents of each of these applications is incorporated herein by reference.

BACKGROUND TO THE INVENTION

Purine analogues as cdk inhibitors are disclosed for example in WO 97/16452, WO 98/05335, WO/9720842, WO 97/16542, WO98/05335, WO 98/39007, WO 98/49146 and WO 99/07705. The teaching of these patents includes 2,6,9-trisubstituted purine derivatives only.

Nucleotide analogues containing phosphonate groups are disclosed for example in U.S. Pat. Nos. 4,659,825; 4,724,233; 5,124,051; 5,302,585; 5,208,221; 5,352,786; 5,356,886; 5,142,051; in EP publication numbers 269,947; 481,214; 630,381; 369,409; 454,427; 618,214; 398,231; 454,427; 468,119; 481,119; 481,214; 434,450 and in WO 95/07920; WO 094/03467, WO96/33200 and WO94/03467. The typical purine base is adenine, 2,6-diaminopurine and guanine. The purine bases may include the aza- and deaza-analogues thereof. 6,9-Substituted and 2,6,9-trisubstituted purines and related analogues are disclosed in WO 96/3320, and some special types of 2,6,9-trisubstituted azapurines are disclosed for example in U.S. Pat. No. 4,027,025; in EP publication number 0,288,431 and in WO 99/05142, WO 99/05143, WO 99/05144, WO 99/41254, WO 00/04021 and WO 00/34283.

It is an object of this invention to provide anticancer, antiinflammatory, antiviral, antineurodegenerative, neurodepressive and immunosuppressive compounds preferably having improved selectivity and efficiency index, i.e. that are less toxic yet more efficacious than analogues known heretofore.

SUMMARY OF THE INVENTION

This invention relates to new 8-azapurine derivatives and to their use in suitable utilities, especially diagnostic- and therapeutic methods.

More preferably, the invention relates to purine derivatives that are capable of exhibiting an inhibitory effect with respect to cyclin-dependent kinase proteins, abbreviated cdks and also with respect to viruses and immunostimulation.

A first aspect of the present invention relates to compounds of formula I, or pharmaceutically acceptable acid salts thereof,

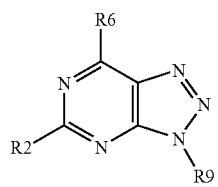

I wherein
R6 is
halogen;
NHNH$_2$;

R6'-X, wherein X is —NH—, —O—, —S—, or —N-(substituted arylalkyl);
R6' is:
H;
acyl, —C(O)R', wherein R' is cycloalkyl, cycloalkyl alkyl, aryl, heterocycle, heteroalkyl, heteroaryl, arylkyl, cycloheteroalkyl, cycloheteroalkyl alkyl, heteroarylalkyl, each of which may be substituted by one or more substituents selected from halogen, amino, hydroxy, mercapto, alkoxy, alkylmercapto, and alkylamino;
cycloalkyl, optionally substituted by one or more substituents selected from halogen, amino, acylamino, acyloxy, hydroxy, mercapto, alkoxy, alkylamino, dialkylamino, alkylmercapto, carboxyl, amido, sulfo, sulfamido, carbamoylamino, nitro and cyano;
cycloalkyl alkyl or —R(cycloalkyl), wherein R is C$_{1-6}$ alkyl, C$_{2-6}$ alkenyl or C$_{2-6}$ alkynyl, each of which may be branched or linear, and wherein said cycloalkyl is optionally substituted as defined above;
heterocycle, aryl, heteroaryl, —R-HetAr, arylalkyl, —RAr, cycloheteroalkyl, cycloheteroalkyl alkyl, —R(cycloheteroalkyl), heteroarylalkyl, —R-HetAr, each of which may be optionally substituted by one or more substituents from those listed above for substituted cycloalkyl, and where R is defined as above;
heteroalkyl or —R-Het, wherein Het is an optionally substituted heterocycle as defined above, and where R is defined as above;
R2 is independently
halogen;
NHNH$_2$;
R as defined above;
substituted C$_1$-C$_6$ alkyl, wherein said alkyl is substituted by one or more substituents selected from those listed above for substituted cycloalkyl
cycloalkyl as defined above;
cycloalkyl alkyl and —R(cycloalkyl) as defined above;
arylalkyl and —RAr as defined above;
heteroalkyl and —R-Het as defined above;
heteroarylalkyl and —R-HetAr as defined above;
cycloheteroalkyl alkyl and —R(cycloheteroalkyl) as defined above;
R2'-X, wherein X is —NH—, —O—, —S— or —N(alkyl)-;
R2' is independently
H;
alkyl, substituted alkyl, acyl, cycloalkyl, substituted cycloalkyl, cycloheteroalkyl, substituted cycloheteroalkyl, cycloalkyl alkyl, aryl, substituted aryl, arylalkyl, heterocycle, heteroaryl, substituted heteroaryl, heteroalkyl or heteroarylalkyl, as defined above;
R9 is independently
alkyl, substituted alkyl, cycloalkyl, substituted cycloalkyl, cycloheteroalkyl, substituted cycloheteroalkyl, cycloalkyl alkyl, aryl, substituted aryl, arylalkyl, heterocycle, heteroaryl, substituted heteroaryl, heteroalkyl or heteroarylalkyl, as defined above.

It is an object of this invention to 2-, 6-disubstituted 8-azapurines and 2-, 6-, 9-trisubstituted 8-azapurine, which inhibit the cdks.

It is another object of this invention to describe 2-, 6-disubstituted 8-azapurines and 2-, 6-, 9-trisubstituted 8-azapurine that are useful for inhibiting cell proliferation and/or inducing apoptosis.

The invention also constitutes a pharmaceutical composition, which comprises a 2-, 6-disubstituted 8-azapurines and 2-, 6-, 9-trisubstituted 8-azapurine, and a pharmaceutically acceptable carrier.

This invention further constitutes a method for inhibiting cell proliferation and inflammatory diseases to a mammal in need of an effective amount 2-, 6-disubstituted 8-azapurines and 2-, 6-, 9-trisubstituted 8-azapurines.

In one embodiment, this invention is 2-, 6-, 9-trisubstituted 8-azapurine composition matter of the formula Ia

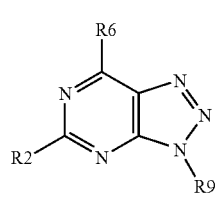

Ia and the pharmaceutically acceptable salts thereof, wherein

R6 is halogen, hydroxyl, amino, hydroxyamino, hydrazino, cyano, sulfo or R6'-X wherein X is an —NH—, —N(alkyl)-, —O— or —S— moiety;

R6' is substituted H, alkyl, substituted alkyl, cycloalkyl, aryl, substituted aryl, substituted heterocycle, substituted heteroaryl, substituted arylalkyl, substituted cycloheteroalkyl, substituted heteroarylalkyl, substituted heteroalkyl, substituted cycloalkyl alkyl and substituted cycloheteroalkyl alkyl by one or more than one halogen, hydroxyl, amino, mercapto, carboxyl, cyano, nitro, amido, sulfo, sulfamoyl, carbamino, ureido and guanidino group.

R2 is halogen, alkyl, aryl, substituted aryl, substituted alkyl, cycloalkyl, substituted cycloalkyl, cycloalkyl alkyl, arylalkyl, heteroalkyl, heteroarylalkyl, cycloheteroalkyl alkyl or R2'-X wherein X is an —NH—, —N(alkyl)-, —O— or —S— moiety.

R2' is H, alkyl, substituted alkyl, acyl, cycloalkyl, substituted cycloalkyl, aryl, substituted aryl, heterocycle, heteroaryl, substituted heteroaryl, arylalkyl, cycloheteroalkyl, substituted cycloheteroalkyl, heteroarylalkyl, heteroalkyl, cycloalkyl alkyl and cycloheteroalkyl alkyl by one or more than one halogen, hydroxyl, amino, mercapto, carboxyl, cyano, nitro, amido, sulfo, sulfamoyl, carbamino, ureido and guanidino group.

R9 is hydrogen, an alkyl, substituted alkyl, cycloalkyl, substituted cycloalkyl, cycloalkyl alkyl, cycloheteroalkyl alkyl, cycloheteroalkyl, substituted cycloheteroalkyl, aryl, substituted aryl, heterocycle, heteroaryl, substituted heteroaryl, arylalkyl, heteroarylalkyl, heteroalkyl;

In another embodiment, this invention is a method for inhibiting cdks and cell proliferation and/or for inducing apoptosis in mammals, comprising administering a therapeutically effective amount of a compound of the invention to the mammal. The cdk inhibiting molecules are useful for treating disorders, some of them involving cell proliferation, such as cancer, restenosis, rheumatoid arthritis, lupus, type I diabetes, multiple sclerosis, Alzheimer's disease, growth of parasites (animal, protists), graft rejection (host versus graft disease), graft versus host disease, and gout.

In another embodiment, this invention is a method for inhibiting or stimulating α- and β-adrenergic and purinergic receptors in mammals comprising administering a therapeutically effective amount of a compound of the invention to the mammal. The inhibiting and stimulating molecules are useful for treating inflammatory diseases and asthma.

In yet another embodiment, this invention is a pharmaceutical composition of matter comprising the composition in an admixture with one or more pharmaceutical excipients.

In still another embodiment, this invention is a composition useful for treating fungal infections (fungi) in humans, animal, and in plants.

2-, 6-disubstituted 8-azapurines and 2-, 6-, 9-trisubstituted 8-azapurines result in the acquisition of extremely high potency against DNA viruses on the part of the defined compounds.

Another aspect relates to the use of a compound of the invention in the manufacture of a medicament for treating one or more of the following disorders: a proliferative disorder; a viral disorder; a stroke; alopecia; a CNS disorder; a neurodegenerative disorder; and diabetes.

A further aspect of the invention relates to the use of a compound of formula 1 for inhibiting a protein kinase.

Another aspect of the invention relates to a method of treating a proliferative disease, said method comprising administering to a mammal a therapeutically effective amount of a compound of formula 1.

Yet another aspect of the invention relates the use of a compound of the invention in an assay for identifying further candidate compounds that influence the activity of one or more CDK enzymes.

DETAILED DESCRIPTION OF THE INVENTION

Figure 1:
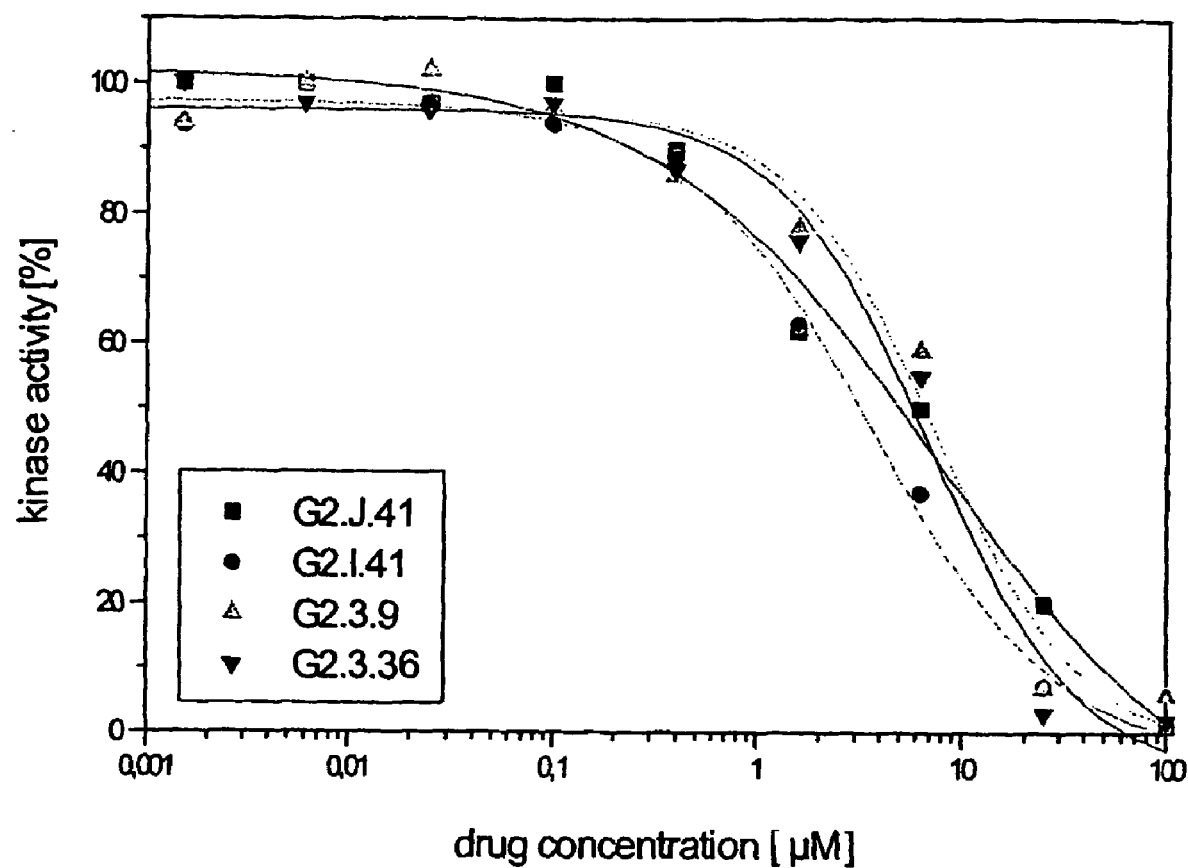
FIG. 1 shows the inhibition of p34$^{cdc2}$/cyclin B by several new 8-azapurines. Enzyme activity was assayed in the presence of increasing concentrations of inhibitors. Activity is presented as percentage of maximal activity, i.e. measured in the absence of inhibitors.

As used herein, and unless modified by the immediate context:

"Halogen" refers to fluorine, bromine, chlorine and iodine atoms.

"Hydroxy" refers to the group —OH.

"Mercapto" refers to group —SH.

"Alkyl" refers to branched or unbranched $C_1$-$C_6$ chain which is saturated or unsaturated. Such groups as methyl, propyl, isopropyl, tert-butyl, allyl, vinyl, ethinyl, propargyl, hexen-2-yl and the like can exemplify this term.

"Substituted alkyl" refers to alkyl as just described including one or more substituents such as hydroxyl, mercapto, alkylmercapto, halogen, alkoxy, amino, acylamino, hydrazino, carbamoyl, amido, carboxyl, sulfo, acyl and the like. These groups may be attached to any carbon atom of the alkyl moiety.

"Alkoxy" denotes the group —OR, where R is alkyl, substituted alkyl, aryl, substituted aryl, arylalkyl, substituted arylalkyl, cycloalkyl, substituted cycloalkyl, cycloheteroalkyl or substituted cycloheteroalkyl as defined.

"Alkylmercapto" denotes the group —SR, where R is as defined for "alkoxy" group.

"Sulfo" denotes the group —$SO_3R$, where R is H, alkyl or substituted alkyl.

"Sulfamido" denotes to the group —$SO_2NRR'$, where R and R' are H, alkyl or substituted alkyl.

"Acyl" denotes groups —C(O)R, where R is hydrogen, alkyl, substituted alkyl, aryl, substituted aryl, arylalkyl, substituted arylalkyl, cycloalkyl, substituted cycloalkyl as defined herein.

"Aryloxy" denotes groups —OAr, where Ar is an aryl, substituted aryl, heteroaryl or substituted heteroaryl group as defined herein.

"Alkylamino" denotes the group —NRR', where R and R' may independently be hydrogen, alkyl, substituted alkyl, aryl, substituted aryl, heteroaryl or substituted heteroaryl as defined herein.

"Amido" denotes the group —C(O)NRR', where R and R' may independently be hydrogen, alkyl, substituted alkyl, aryl, substituted aryl, heteroaryl, substituted heteroaryl as defined herein.

"Carboxyl" denotes the group —C(O)OR, where R is hydrogen, alkyl, substituted alkyl, aryl, substituted aryl, hetaryl or substituted hetaryl as defined herein.

"Acylamino" denotes the group —NHCOR, where R may be alkyl, substituted alkyl, heterocycle, aryl, substituted aryl, heteroaryl and substituted heteroaryl as defined herein.

"Carbamoylamino" denotes the group NHCOOR, where R is alkyl or aryl

"Aryl" or "Ar" refers to an aromatic carbocyclic group having at least one aromatic ring (e.g., phenyl or biphenyl) or multiple condensed rings in which at least one ring is aromatic (e.g., 1,2,3,4-tetrahydronaphthyl, naphthyl, anthryl, or phenanthryl).

"Substituted aryl" refers to aryl as just described which is optionally substituted with one or more functional groups such as halogen, alkyl, hydroxy, amino, acylamino, carbamoylamino, hydrazino, acyloxy, mercapto, alkoxy, alkylmercapto, alkylamino, amido, carboxyl, nitro, sulfo and the like.

"Heterocycle" refers to a unsaturated or aromatic carbocyclic group having at least one hetero atom, such as N, O or S, within the ring; the ring can be single (e.g. pyranyl, pyridyl or furyl) or multiple condensed (e.g., quinazolinyl, purinyl, quinolinyl or benzofuranyl) which can optionally be unsubstituted or substituted with, e.g., halogen, amino, acylamino, carbamoylamino, hydrazino, acyloxy, alkyl, alkoxy, alkylmercapto, alkylamino, amido, carboxyl, hydroxy, nitro, mercapto, sulfo and the like.

"Heteroaryl" refers to a heterocycle in which at least one heterocyclic ring is aromatic.

"Substituted heteroaryl" refers to a heterocycle optionally mono or poly substituted with one or more functional groups, e.g., halogen alkyl, alkoxy, alkylthio, alkylamino, amido, carboxyl, hydroxyl, nitro, mercapto, sulfo and the like.

"Arylalkyl" refers to the group —R—Ar where Ar is an aryl group and R is alkyl or substituted alkyl group. The aryl groups can optionally be unsubstituted or substituted with, e.g., halogen, amino, acylamino, carbamoylamino, hydrazino, acyloxy, alkyl, hydroxyl, alkoxy, alkylmercapto, alkylamino, amido, carboxyl, hydroxy, aryl, nitro, mercapto, sulfo and the like.

"Heteroalkyl" refers to the group —R-Het where Het is a heterocycle group and R is an alkyl group. Heteroalkyl groups can optionally be unsubstituted or substituted with e.g., halogen, alkyl, alkoxy, alkylmercapto, alkylamino, amido, carboxy, alkoxycarbonyl, aryl, aryloxy, nitro, mercapto, sulfonyl and the like.

"Heteroarylalkyl" refers to the group —R-HetAr where HetAr is an heteroaryl group and R is alkyl or substituted alkyl. Heteroarylalkyl groups can optionally be unsubstituted or substituted with, e.g., halogen, alkyl, substituted alkyl, alkoxy, alkylmercapto, nitro, thiol, sulfo and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, amino, acylamino, carbamoylamino, hydrazino, acyloxy, alkyl, substituted alkyl, alkoxy, alkylmercapto, aryl, nitro, mercapto, sulfo and the like.

"Cycloheteroalkyl" refers to a cycloalkyl group wherein one or more of the ring carbon atoms is replaced with a heteroatom (e.g., N, O, S).

"Substituted cycloheteroalkyl" refers to a cycloheteroalkyl group as herein defined which contains one or more substituents, such as halogen, alkyl, alkoxy, alkylmercapto, alkylamino, amino, acylamino, hydrazino, amido, carboxyl, hydroxy, nitro, mercapto, sulfo and the like.

"Cycloalkyl alkyl" denotes the group —R-cycloalkyl where cycloalkyl is a cycloalkyl group and R is an alkyl or substituted alkyl. Cycloalkyl groups can optionally be unsubstituted or substituted with e.g., halogen, alkyl, alkoxy, alkylmercapto, alkylamino, amino, acylamino, acyloxy, amido, carboxyl, hydroxy, nitro, mercapto, sulfo and the like.

"Cycloheteroalkyl alkyl" denotes the group —R-cycloheteroalkyl where R is a alkyl or substituted alkyl. Cycloheteroalkyl groups can optionally be unsubstituted or substituted with e.g. halogen, alkyl, alkoxy, alkylmercapto, alkylamino, amino, acylamino, acyloxy, amido, carboxyl, hydroxy, nitro, mercapto, sulfo and the like.

A preferred embodiment of this invention relates to 2-, 6-disubstituted 8-azapurines and 2-, 6-, 9-trisubstituted 8-azapurines, which are capable of inhibiting or stimulate the cyclin-dependent kinases and α- and β-adrenergic and purinergic receptors and have formula Ib

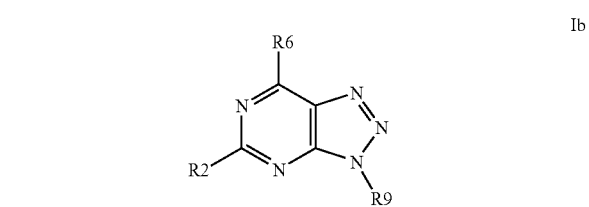

Ib and the pharmaceutically acceptable acid salts thereof, wherein

R6 is:

halogen

NHNH$_2$.

R6'-X, wherein X is —NH—, —O—, —S—;

R6'-X, wherein X is preferably —N(substituted arylakyl)-. Substituted arylalkyl is preferably mono, di or tri substituted benzylamine with halogen, amino, hydroxy, cyano, nitro, mercapto, alkoxy, alkylamino, dialkylamino, acylamino, carbanoylamino, acyloxy, alkylmercapto, carboxyl, amido, sulfo, sulfamido, sulfamoyl, ureido, guanadino or α-(aminomethyl)-mono-, di- or tri-substituted benzyl alcohol by substitutents defined for benzylamines;

R6' is:

H;

acyl, —C(O)R, wherein R is cycloalkyl, cycloalkyl alkyl, aryl, heterocycle, heteroalkyl, heteroaryl, arylkyl, cycloheteroalkyl, cycloheteroalkyl alkyl, heteroarylakyl. These alkyls can be substituted at each occurrence with 0-5 substituents selected from the group halogen, amino, hydroxy, mercapto, alkoxy, alkylmercapto, alkylamino;

cycloalkyl. The above said cycloalkyl can be substituted at each occurrence with 0-5 substituents selected from the group halogen, amino, acylamino, acyloxy, hydroxy, mercapto, alkoxy, alkylamino, dialkylamino, alkylmercapto, carboxyl, amido, sulfo, sulfamido, carbamoylamino, nitro or cyano. Preferable substituents are chloro, fluoro, hydroxy, carboxyl or amido;

cycloalkyl alkyl, —R(cycloalkyl), wherein R is lower alkyl, branched or linear, saturated or unsaturated. Typically methyl, ethyl, propyl, isopropyl, allyl, propargyl, isopentenyl, isobutenyl, and cycloalkyl is as defined above for cycloalkyl and substituted cycloalkyl. Cycloalkyl can be substituted as defined for substituted cycloalkyl; substituted aryl, wherein aryl is typically phenyl, biphenyl, naphthyl, tetrahydronaphthyl, fluorenyl, indenyl or fenanthrenyl. The aryl ring(s) can be substituted at each occurrence with 0-5 substituents selected from the group defined above for substituted cycloalkyl. Preferable substituents are chloro, fluoro, hydroxy, amino, acylamino, acyloxy, carboxyl or amido;

heterocycle, wherein heterocycle is preferentially thienyl, furyl, pyranyl, pyrrolyl, imidazolyl, pyrazolyl, pyridyl, pyrazinyl, pyrimidinyl, pyridazinyl, isothiazolyl, isoxazyl. Heterocycle ring can be substituted at each occurrence with 0-5 substituents selected from the groups defined above for substituted cycloalkyl;

aryl, where aryl is typically phenyl, biphenyl, naphthyl, tetrahydronaphthyl, fluorenyl, indenyl or fenanthrenyl. The aryl ring(s) can be substituted at each occurrence with 0-5 substituents selected from the groups defined above for substituted cycloalkyl. Preferable substituents are chloro, fluoro, hydroxy, amino, acylamino, acyloxy, carboxyl or amido;

heteroalkyl, —R-Het, wherein R is lower alkyl, typically methyl, ethyl, propyl, isopropyl, vinyl, propinyl, propenyl, ethinyl. Typical Het-substituents are as described above for the heterocycle group. The heterocycle ring can be substituted by 0 to 5 substituents as defined above for substituted cycloalkyl;

heteroaryl, —R-HetAr, wherein R is usually methyl, ethyl, propyl, isopropyl, vinyl, propinyl, propenyl and HetAr is benzothienyl, naphthothienyl, benzofuranyl, chromenyl, indolyl, isoindolyl, indazolyl, quinolinyl, isoquinolinyl, phtalazinyl, quinaxilinyl, cinnolinyl, quinazolinyl. The heteroaryl ring(s) can be substituted by 0 to 5 independent groups, which are defined in detail above for substituted cycloalkyl;

arylalkyl, —RAr, wherein R is $C_1$-$C_6$ lower alkyl, branched or linear, saturated or unsaturated, typically methyl, ethyl, propyl, isopropyl, vinyl, propinyl, propenyl. The aryl ring(s) can be substituted by 0 to 5 independent groups, which are defined in detail above for substituted cycloalkyl;

cycloheteroalkyl, wherein cycloheteroalkyl is preferentially piperidinyl, piperazinyl, morfolinyl, pyrrolidinyl, imidazolidinyl. The cycloheteroalkyl ring can be substituted by 0 to 5 substituents, preferably those defined above for substituted cycloalkyl;

cycloheteroalkyl alkyl, —R(cycloheteroalkyl), wherein R is as defined above for arylalkyl group. The cycloheteroalkyl ring can be substituted by 0 to 5 substituents defined above for cycloalkyl;

heteroarylalkyl, —R-HetAr, wherein R is lower alkyl, branched or linear, saturated or unsaturated, typically methyl, ethyl, propyl, isopropyl, vinyl, propinyl, propenyl, allyl, propargyl, isopentenyl. HetAr is typically benzothienyl, benzofuranyl, chromenyl, indolyl, isoindolyl, indazolyl, quinolinyl, phthalazinyl, quinoxalinyl, quinazolinyl, carbazolyl, acridinyl, indolinyl, and isoindolinyl. R and HetAr can independently be substituted by halogen, hydroxyl, amino, mercapto, methoxy, carboxyl or amido;

R2 is independently halogen $NHNH_2$;

$C_1$-$C_6$ alkyl, linear or branched, saturated or unsaturated;

substituted $C_1$-$C_6$ alkyl, wherein above said alkyl is substituted by 1 or 2 substituents, in particular by halogen, hydroxy, mercapto, amino, alkoxy, alkylmercapto, alkylamino, carboxyl, amido, carbamino sulfo or sulfamido;

$C_3$-$C_{15}$ cycloalkyl as defined above;

cycloalkyl alkyl and —R(cycloalkyl) as defined above;

arylalkyl and —RAr as defined above;

heteroalkyl and —R-Het as defined above;

heteroarylalkyl and —R-HetAr as defined above;

cycloheteroalkyl alkyl and —R(cycloheteroalkyl) as defined above;

R2'-X, wherein X is —NH—, —O—, —S— moiety;

R2'-X, wherein X is —N(alkyl)-. Alkyl is usually $C_1$-$C_6$ alkyl, methyl, ethyl, propyl isopropyl, vinyl, allyl, propargyl;

R2' is independently

H;

alkyl, substituted alkyl, acyl, cycloalkyl, substituted cycloalkyl, cycloheteroalkyl, substituted cycloheteroalkyl, cycloalkyl alkyl, aryl, substituted aryl, arylalkyl, heterocycle, heteroaryl, substituted heteroaryl, heteroalkyl or heteroarylalkyl. These groups are as defined for R6'. R2' are according to any one of the substituents defined above for R6'.

R9 is independently hydrogen, alkyl, substituted alkyl, cycloalkyl, substituted cycloalkyl, cycloheteroalkyl, substituted cycloheteroalkyl, cycloalkyl alkyl, aryl, substituted aryl, arylalkyl, heterocycle, heteroaryl, substituted heteroaryl, heteroalkyl or heteroarylalkyl. These groups are as defined above. Preferred R9 substituents are hydrogen and those defined for R6.

Preferred embodiments of the invention are the same for compounds of formula I, Ia and Ib.

In one preferred embodiment, said heterocycle is selected from thienyl, furyl, pyranyl, pyrrolyl, imidazolyl, pyrazolyl, pyridyl, pyrazinyl, pyrimidinyl, pyridazinyl, isothiazolyl, and isoxazyl;

said aryl is selected from phenyl, biphenyl, naphthyl, tetrahydronaphthyl, fluorenyl, indenyl and phenanthrenyl;

said cycloheteroalkyl is selected from piperidinyl, piperazinyl, morpholinyl, pyrrolidinyl, imidazolidinyl;

said HetAr is selected from benzothienyl, naphthothienyl, benzofuranyl, chromenyl, indolyl, isoindolyl, indazolyl, quinolinyl, isoquinolinyl, phthalazinyl, cinnolinyl, quinazoliny, quinoxalinyl, carbazolyl, acridinyl, indolinyl, and isoindolinyl.

In one preferred embodiment, R6 is R6'-N(substituted arylalkyl) and said N(substituted arylalkyl) is benzylamine substituted by one or more of halogen, amino, hydroxy, cyano, nitro, mercapto, alkoxy, alkylamino, dialkylamino, acylamino, carbanoylamino, acyloxy, alkylmercapto, carboxyl, amido, sulfo, sulfamido, or α-(aminomethyl)-di- and tri-substituted benzyl alcohol.

In another preferred embodiment, R6' is an aryl group optionally substituted by one or more substituents selected from chloro, fluoro, hydroxy, amino, acylamino, acyloxy, carboxyl and amido.

In one preferred embodiment, said cycloalkyl, cycloalkyl alkyl, —R(cycloalkyl), heterocycle, aryl, heteroaryl, —R-HetAr, arylalkyl, —RAr, cycloheteroalkyl, cycloheteroalkyl alkyl, —R(cycloheteroalkyl), heteroarylalkyl, or —R-HetAr group is substituted by one or more substituents selected from chloro, fluoro, hydroxy, carboxyl and amido.

Preferably, R is selected from methyl, ethyl, ethynyl, propyl, isopropyl, vinyl, propynyl, propenyl, allyl, propargyl, isopentenyl and isobutenyl.

In one particularly preferred embodiment of the invention, R9 is isopropyl or methyl.

In another particularly preferred embodiment, R6 is
anilino or benzylamino, each of which may optionally be substituted by one or more substituents selected from halogen, OH, $NO_2$, COOH, $NH_2$, acetoxy, sulfamoyl, acetyl, MeO and Me; or
substituted alkylamino.

More preferably still, R6 is
anilino, optionally substituted by one or more substituents selected from halogen, OH, COOH and $NH_2$; or
benzylamino, optionally substituted by one or more substituents selected from halogen, OH, $NO_2$, $NH_2$, acetoxy, sulfamoyl, acetyl, MeO and Me;
ureidopropylamino; or guanidinopropylamino.

In another particularly preferred embodiment, R2 is halogen; alkyl; optionally substituted alkylamino; optionally substituted cycloalkylamino; optionally substituted benzylamino; or optionally substituted phenylamino.

In another particularly preferred embodiment, R2 is halogen; alkyl; alkylamino optionally substituted by one or more substituents selected from OH, $NH_2$, guanadino and ureido; cycloalkylamino, optionally substituted by one or more $NH_2$ groups; benzylamino optionally substituted by one or more $NH_2$ or $NO_2$ groups; phenylamino, optionally substituted by one or more sulfamoyl groups.

In one especially preferred embodiment, R2 is selected from the C2 substituents listed in Tables 1-10.

In one especially preferred embodiment, R6 is selected from the C6 substituents listed in Tables 1-10.

The following derivatives are particularly preferred, namely: 2-[1-(hydroxymethyl)propylamino]-6-benzylamino-8-azapurine, 2-[((R)-2-(hydroxymethyl)pyrrolidine-1-yl)]-6-benzylamino-8-azapurine, 2-(2-aminopropylamino)-6-benzylamino-8-azapurine, 2-(2-hydroxypropylamino)-6-benzylamino-8-azapurine, 2-(1(R)-isopropyl-2-hydroxyethylamino)-6-benzylamino-8-azapurine, 2-(4-aminocyclohexylamino)-6-benzylamino-9-isopropyl-8-azapurine, 2-(2-aminocyclohexylamino)-6-benzylamino-8-azapurine, 2-[1-(hydroxymethyl)propylamino]-6-(3-acetoxybenzylamino)-8-azapurine, 2-[(R)-2-(hydroxymethyl)pyrrolidine-1-yl]-6-(3-acetoxybenzylamino)-8-azapurine, 2-(2-aminopropylamino)-6-(3-acetoxybenzylamino)-8-azapurine, 2-(2-hydroxypropylamino)-6-(3-acetoxybenzylamino)-8-azapurine, 2-1(R)-isopropyl-2-hydroxyethylamino)-6-(3-acetoxybenzylamino)-8-azapurine, 2-(4-aminocyclohexylamino)-6-(3-acetoxybenzylamino)-8-azapurine, 2-(2-aminocyclohexylamino)-6-(3-acetoxybenzylamino)-8-azapurine, 2-[1-(hydroxymethyl)propylamino]-6-(2-hydroxy-3-methoxybenzylamino)-8-azapurine, 2-[(R)-2-(hydroxymethyl)pyrrolidine-1-yl]-6-(2-hydroxy-3-methoxybenzylamino)-8-azapurine, 2-(2-aminopropylamino)-6-(2-hydroxy-3-methoxybenzylamino)-8-azapurine, 2-(2-hydroxypropylamino)-6-(2-hydroxy-3-methoxybenzylamino)-8-azapurine, 2-(1(R)-isopropyl-2-hydroxyethylamino)-6-(2-hydroxy-3-methoxybenzylamino)-8-azapurine, 2-(4-aminocyclohexylamino)-6-(2-hydroxy-3-methoxybenzylamino)-8-azapurine, 2-(2-aminocyclohexylamino)-6-(2-hydroxy-3-methoxybenzylamino)-8-azapurine, 2-[1-(hydroxymethyl)propylamino]-6-(2,3-dihydroxy-4-methoxybenzylamino)-8-azapurine, 2-[(R)-2-(hydroxymethyl)pyrrolidine-1-yl]-6-(2,3-dihydroxy-4-methoxybenzylamino)-8-azapurine, 2-(2-aminopropylamino)-6-(2,3-dihydroxy-4-methoxybenzylamino)-8-azapurine, 2-(2-hydroxypropylamino)-6-(2,3-dihydroxy-4-methoxybenzylamino)-8-azapurine, 2-(1(R)-isopropyl-2-hydroxyethylamino)-6-(2,3-dihydroxy-4-methoxybenzylamino)-8-azapurine, 2-(4-aminocyclohexylamino)-6-(2,3-dihydroxy-4-methoxybenzylamino)-8-azapurine, 2-(2-aminocyclohexylamino)-6-(2,3-dihydroxy-4-methoxybenzylamino)-8-azapurine, 2-[1-(hydroxymethyl)propylamino]-6-(2,5-dihydroxy-4-methoxybenzylamino)-8-azapurine, 2-[(R)-2-(hydroxymethyl)pyrrolidine-1-yl]-6-(2,5-dihydroxy-4-methoxybenzylamino)-8-azapurine, 2-(2-aminopropylamino)-6-(2,5-dihydroxy-4-methoxybenzylamino)-8-azapurine, 2-(2-hydroxypropylamino)-6-(2,5-dihydroxy-4-methoxybenzylamino)-8-azapurine, 2-(1(R)-isopropyl-2-hydroxyethylamino)-6-(2,5-dihydroxy-4-methoxybenzylamino)-8-azapurine, 2-(4-aminocyclohexylamino)-6-(2,5-dihydroxy-4-methoxybenzylamino)-8-azapurine, 2-(2-aminocyclohexylamino)-6-(2,5-dihydroxy-4-methoxybenzylamino)-8-azapurine, 2-[1-(hydroxymethyl)propylamino]-6-(2,6-dihydroxy-4-methoxybenzylamino)-8-azapurine, 2-[(R)-2-(hydroxymethyl)pyrrolidine-1-yl]-6-(2,6-dihydroxy-4-methoxybenzylamino)-8-azapurine, 2-(2-aminopropylamino)-6-(2,6-dihydroxy-4-methoxybenzylamino)-8-azapurine, 2-(2-hydroxypropylamino)-6-(2,6-dihydroxy-4-methoxybenzylamino)-8-azapurine, 2-(1(R)-isopropyl-2-hydroxyethylamino)-6-(2,6-dihydroxy-4-methoxybenzylamino)-8-azapurine, 2-(4-aminocyclohexylamino)-6-(2,6-dihydroxy-4-methoxybenzylamino)-8-azapurine, 2-(2-aminocyclohexylamino)-6-(2,6-dihydroxy-4-methoxybenzylamino)-8-azapurine, 2-[1-(hydroxymethyl)propylamino]-6-(2,3-dihydroxy-4-chlorobenzylamino)-8-azapurine, 2-[(R)-2-(hydroxymethyl)pyrrolidine-1-yl]-6-(2,3-dihydroxy-4-chlorobenzylamino)-8-azapurine, 2-(2-aminopropylamino)-6-(2,3-dihydroxy-4-chlorobenzylamino)-8-azapurine, 2-(2-hydroxypropylamino)-6-(2,3-dihydroxy-4-chlorobenzylamino)-8-azapurine, 2-(1(R)-isopropyl-2-hydroxyethylamino)-6-(2,3-dihydroxy-4-chlorobenzylamino)-8-azapurine, 2-(4-aminocyclohexylamino)-6-(2,3-dihydroxy-4-chlorobenzylamino)-8-azapurine, 2-(2-aminocyclohexylamino)-6-(2,3-dihydroxy-4-chlorobenzylamino)-8-azapurine, 2-[1-(hydroxymethyl)propylamino]-6-(2,5-dihydroxy-4-chlorobenzylamino)-8-azapurine, 2-[(R)-2-(hydroxymethyl)pyrrolidine-1-yl]-6-(2,5-dihydroxy-4-chlorobenzylamino)-8-azapurine, 2-(2-aminopropylamino)-6-(2,5-dihydroxy-4-chlorobenzylamino)-8-azapurine, 2-(2-hydroxypropylamino)-6-(2,5-dihydroxy-4- chlorobenzylamino)-8-azapurine, 2-(1(R)-isopropyl-2-hydroxyethylamino)-6-(2,5-dihydroxy-4-chlorobenzylamino)-8-azapurine, 2-(4-aminocyclohexylamino)-6-(2,5-dihydroxy-4-chlorobenzylamino)-8-azapurine, 2-[1-(hydroxymethyl)propylamino]-6-(2,6-dihydroxy-4-chlorobenzylamino)-8-azapurine, 2-[(R)-2-(hydroxymethyl)pyrrolidine-1-yl]-6-(2,6-dihydroxy-4-chlorobenzylamino)-8-azapurine, 2-(2-aminopropylamino)-6-(2,6-dihydroxy-4-chlorobenzylamino)-8-azapurine, 2-(2-hydroxypropylamino)-6-(2,6-dihydroxy-4-chlorobenzylamino)-8-azapurine, 2-(1(R)-isopropyl-2-hydroxyethylamino)-6-(2,6-dihydroxy-4-chlorobenzylamino)-8-azapurine, 2-(4-aminocyclohexylamino)-6-(2,6-dihydroxy-4-chlorobenzylamino)-8-azapurine, 2-(2-aminocyclohexylamino)-6-(2,6-dihydroxy-4-chlorobenzylamino)-8-azapurine, 2-(2-aminocyclohexylamino)-6-(2,6-dihydroxy-4-chlorobenzylamino)-8-azapurine, 2-[1-(hydroxymethyl)propylamino]-6-(2-acetoxybenzylamino)-8-azapurine, 2-[(R)-2-(hydroxymethyl)pyrrolidine-1-yl]-6-(2-acetoxybenzylamino)-8-azapurine, 2-(2-aminopropylamino)-6-(2-acetoxybenzylamino)-8-azapurine, 2-(2-hydroxypropylamino)-6-(2-acetoxybenzylamino)-8-azapurine, 2-(1(R)-isopropyl-2-hydroxyethylamino)-6-(2-acetoxybenzylamino)-8-azapurine, 2-(4-aminocyclohexylamino)-6-(2-acetoxybenzylamino)-8-azapurine, 2-(2-aminocyclohexylamino)-6-(2-acetoxybenzylamino)-8-azapurine, 2-[1-(hydroxymethyl)propylamino]-6-(2-aminobenzylamino)-8-azapurine, 2-[(R)-2-(hydroxymethyl)pyrrolidine-1-yl]-6-(2-aminobenzylamino)-8-azapurine, 2-(2-aminopropylamino)-6-(2-aminobenzylamino)-8-azapurine, 2-(2-hydroxypropylamino)-6-(2-aminobenzylamino)-8-azapurine, 2-(1(R)-isopropyl-2-hydroxyethylamino)-6-(2-aminobenzylamino)-8-azapurine, 2-(4-aminocyclohexylamino)-6-(2-aminobenzylamino)-8-azapurine, 2-(2-aminocyclohexylamino)-6-(2-aminobenzylamino)-8-azapurine, 2-[1-(hydroxymethyl)propylamino]-6-(2-amino-6-chlorobenzylamino)-8-azapurine, 2-[(R)2-(hydroxymethyl)pyrrolidine-1-yl]-6-(2-amino-6-chlorobenzylamino)-8-azapurine, 2-(2-aminopropylamino)-6-(2-amino-6-chlorobenzylamino)-8-azapurine, 2-(2-hydroxypropylamino)-6-(2-amino-6-chlorobenzylamino)-8-azapurine, 2-(1(R)-isopropyl-2-hydroxyethylamino)-6-(2-amino-6-chlorobenzylamino)-8-azapurine, 2-(4-aminocyclohexylamino)-6-(2-amino-6-chlorobenzylamino)-8-azapurine, 2-(2-aminocyclohexylamino)-6-(2-amino-6-chlorobenzylamino)-8-azapurine, 2-[1-(hydroxymethyl)propylamino]-6-(3-amino-4-chlorobenzylamino)-8-azapurine, 2-[(R)-2-(hydroxymethyl)pyrrolidine-1-yl]-6-(3-amino-4-chlorobenzylamino)-9-isopropyl(methyl,ethyl)-8-azapurine, 2-(2-aminopropylamino)-6-(3-amino-4-chlorobenzylamino)-8-azapurine, 2-(2-hydroxypropylamino)-6-(3-amino-4-chlorobenzylamino)-8-azapurine, 2-(1(R)-isopropyl-2-hydroxyethylamino)-6-(3-amino-4-chlorobenzylamino)-8-azapurine, 2-(4-aminocyclohexylamino)-6-(3-amino-4-chlorobenzylamino)-8-azapurine, 2-(2-aminocyclohexylamino)-6-(3-amino-4-chlorobenzylamino)-8-azapurine, 2-[1-(hydroxymethyl)propylamino]-6-(3-acetylbenzylamino)-8-azapurine, 2-[(R)-2-(hydroxymethyl)pyrrolidine-1-yl]-6-(3-acetylbenzylamino)-9-isopropyl(methyl,ethyl)-8-azapurine, 2-(2-aminopropylamino)-6-(3-acetylbenzylamino)-8-azapurine, 2-(2-hydroxypropylamino)-6-(3-acetylbenzylamino)-8-azapurine, 2-(1(R)-isopropyl-2-hydroxyethylamino)-6-(3-acetylbenzylamino)-8-azapurine, 2-(4-aminocyclohexylamino)-6-(3-acetylbenzylamino)-8-azapurine, 2-(2-aminocyclohexylamino)-6-(3-acetylbenzylamino)-8-azapurine, 2-[1-(hydroxymethyl)propylamino]-6-(2-acetylbenzylamino)-8-azapurine, 2-[(R)-2-(hydroxymethyl)pyrrolidine-1-yl]-6-(2-acetylbenzylamino)-8-azapurine, 2-(2-aminopropylamino)-6-(2-acetylbenzylamino)-8-azapurine, 2-(2-hydroxypropylamino)-6-(2-acetylbenzylamino)-8-azapurine, 2-(1(R)-isopropyl-2-hydroxyethylamino)-6-(2-acetylbenzylamino)-8-azapurine, 2-(4-aminocyclohexylamino)-6-(2-acetylbenzylamino)-8-azapurine, 2-(2-aminocyclohexylamino)-6-(2-acetylbenzylamino)-8-azapurine, 2-[1-(hydroxymethyl)propylamino]-6-anilino-8-azapurine, 2-[(R)-2-(hydroxymethyl)pyrrolidine-1-yl]-6-anilino-8-azapurine, 2-(2-aminopropylamino)-6-anilino-8-azapurine, 2-(2-hydroxypropylamino)-6-anilino-8-azapurine, 2-(1(R)-isopropyl-2-hydroxyethylamino)-6-anilino-8-azapurine, 2-(4-aminocyclohexylamino)-6-anilino-8-azapurine, 2-(2-aminocyclohexylamino)-6-anilino-8-azapurine, 2-[1-(hydroxymethyl)propylamino]-6-(3-chloroanilino)-8-azapurine, 2-[(R)-2-(hydroxymethyl)pyrrolidine-1-yl]-6-(3-chloroanilino)-8-azapurine, 2-(2-aminopropylamino)-6-(3-chloroanilino)-8-azapurine, 2-(2-hydroxypropylamino)-6-(3-chloroanilino)-8-azapurine, 2-(1(R)-isopropyl-2-hydroxyethylamino)-6-(3-chloroanilino)-8-azapurine, 2-(4-aminocyclohexylamino)-6-(3-chloroanilino)-8-azapurine, 2-(2-aminocyclohexylamino)-6-(3-chloroanilino)-8-azapurine, 2-[1-(hydroxymethyl)propylamino]-6-(4-chloroanilino)-8-azapurine, 2-[(R)(2-hydroxymethyl)pyrrolidine-1-yl]-6-(4-chloroanilino)-8-azapurine, 2-(2-aminopropylamino)-6-(4-chloroanilino)-8-azapurine, 2-(2-hydroxypropylamino)-6-(4-chloroanilino)-8-azapurine, 2-(1(R)-isopropyl-2-hydroxyethylamino)-6-(4-chloroanilino)-8-azapurine, 2-(4-aminocyclohexylamino)-6-(4-chloroanilino)-8-azapurine, 2-(2-aminocyclohexylamino)-6-(4-chloroanilino)-8-azapurine, 2-[1-(hydroxymethyl)propylamino]-6-(4-bromoanilino)-8-azapurine, 2-[(R)-2-(hydroxymethyl)pyrrolidine-1-yl]-6-(4-bromoanilino)-8-azapurine, 2-(2-aminopropylamino)-6-(4-bromoanilino)-8-azapurine, 2-(2-hydroxypropylamino)-6-(4-bromoanilino)-8-azapurine, 2-(1(R)-isopropyl-2-hydroxyethylamino)-6-(4-bromoanilino)-8-azapurine, 2-(4-aminocyclohexylamino)-6-(4-bromoanilino)-8-azapurine, 2-(2-aminocyclohexylamino)-6-(4-bromoanilino)-8-azapurine, 2-[1-(hydroxymethyl)propylamino]-6-(3-chloro-5-aminoanilino)-8-azapurine, 2-[(R)-2-(hydroxymethyl)pyrrolidine-1-yl]-6-(3-chloro-5-aminoanilino)-8-azapurine, 2-(2-aminopropylamino)-6-(3-chloro-5-aminoanilino)-8-azapurine, 2-(2-hydroxypropylamino)-6-(3-chloro-5-aminoanilino)-8-azapurine, 2-(1(R)-isopropyl-2-hydroxyethylamino)-6-(3-chloro-5-aminoanilino)-8-azapurine, 2-(4-aminocyclohexylamino)-6-(3-chloro-5-aminoanilino)-8-azapurine, 2-(2-aminocyclohexylamino)-6-(3-chloro-5-aminoanilino)-8-azapurine, 2-[1-(hydroxymethyl)propylamino]-6-(3-chloro-4-carboxyanilino)-8-azapurine, 2-[(R)-2-(hydroxymethyl)pyrrolidine-1-yl]-6-(3-chloro-4-carboxyanilino)-8-azapurine, 2-(2-aminopropylamino)-6-(3-chloro-4-carboxyanilino)-8-azapurine, 2-(2-hydroxypropylamino)-6-(3-chloro-4-carboxyanilino)-8-azapurine, 2-(1(R)-isopropyl-2-hydroxyethylamino)-6-(3-chloro-4-carboxyanilino)-8-azapurine, 2-(4-aminocyclohexylamino)-6-(3-chloro-4-carboxyanilino)-8-azapurine, 2-(2-aminocyclohexylamino)-6-(3-chloro-4-carboxyanilino)-8-azapurine, 5-[1-(hydroxymethyl)propylamino]-7-(3-carboxy-4-chloroanilino)-8-azapurine, 2-[(R)-2-

(hydroxymethyl)pyrrolidine-1-yl)-6-(3-carboxy-4-chloroanilino)-8-azapurine, 2-(2-aminopropylamino)-6-(3-carboxy-4-chloroanilino)-8-azapurine, 2-(2-hydroxypropylamino)-6-(3-carboxy-4-chloroanilino)-8-azapurine, 2-(1(R)-isopropyl-2-hydroxyethylamino)-6-(3-carboxy-4-chloroanilino)-8-azapurine, 2-(4-aminocyclohexylamino)-6-(3-carboxy-4-chloroanilino)-8-azapurine, 2-(2-aminocyclohexylamino)-6-(3-carboxy-4-chloroanilino)-8-azapurine, 2-[1-(hydroxymethyl)propylamino]-6-(3-amino-4-chloroanilino)-8-azapurine, 2-[(R)2-(hydroxymethyl)pyrrolidine-1-yl]-6-(3-amino-4-chloroanilino)-8-azapurine, 2-(2-aminopropylamino)-6-(3-amino-4-chloroanilino)-8-azapurine, 2-(2-hydroxypropylamino)-6-(3-amino-4-chloroanilino)-8-azapurine, 2-(1(R)-isopropyl-2-hydroxyethylamino)-6-(3-amino-4-chloroanilino)-8-azapurine, 2-(4-aminocyclohexylamino)-6-(3-amino-4-chloroanilino)-8-azapurine, 2-(2-aminocyclohexylamino)-6-(3-amino-4-chloroanilino)-8-azapurine, 2-[1-(hydroxymethyl)propylamino]-6-(3-chloro-4-aminoanilino)-8-azapurine, 2-[(R)2-(hydroxymethyl)pyrrolidine-1-yl]-6-(3-chloro-4-aminoanilino)-8-azapurine, 2-(2-aminopropylamino)-6-(3-chloro-4-aminoanilino)-8-azapurine, 2-(2-hydroxypropylamino)-6-(3-chloro-4-aminoanilino)-8-azapurine, 2-(1(R)-isopropyl-2-hydroxyethylamino)-6-(3-chloro-4-aminoanilino)-8-azapurine, 2-(4-aminocyclohexylamino)-6-(3-chloro-4-aminoanilino)-8-azapurine, 2-(2-aminocyclohexylamino)-6-(3-chloro-4-aminoanilino)-8-azapurine, 2-[1-(hydroxymethyl)propylamino]-6-(3-carboxy-4-hydroxyanilino)-8-azapurine, 2-[(R)2-(hydroxymethyl)pyrrolidine-1-yl]-6-(3-carboxy-4-hydroxyanilino)-8-azapurine, 2-(2-aminopropylamino)-6-(3-carboxy-4-hydroxyanilino)-8-azapurine, 2-(2-hydroxypropylamino)-6-(3-carboxy-4-hydroxyanilino)-8-azapurine, 2-(1(R)-isopropyl-2-hydroxyethylamino)-6-(3-carboxy-4-hydroxyanilino)-8-azapurine, 2-(4-aminocyclohexylamino)-6-(3-carboxy-4-hydroxyanilino)-8-azapurine, 2-(2-aminocyclohexylamino)-6-(3-carboxy-4-hydroxyanilino)-8-azapurine, 2-(2-hydroxypropylamino)-6-[N-(3,4-dihydroxybenzyl)-N-methyl]amino-8-azapurine, 2-(1(R)-isopropyl-2-hydroxyethylamino)-6-[N-(3,4-dihydroxybenzyl)-N-methyl]amino-8-azapurine, 2-(2-hydroxypropylamino)-6-[1-(3,4-dihydroxyphenyl)ethyl]amino-8-azapurine, 2-(1(R)-isopropyl-2-hydroxyethylamino)-6-[1-(3,4-dihydroxyphenyl)ethyl]amino-8-azapurine, 2-(1(R)-isopropyl-2-hydroxyethylamino)-6-[N-(2-(3,4-dihydroxyfenyl)ethyl)-N-methyl]amino-8-azapurine, 2-(1(R)-isopropyl-2-hydroxyethylamino)-6-[(R)-(1-phenyl-2-hydroxyethyl)amino]-8-azapurine, 2-(1(R)-isopropyl-2-hydroxyethylamino)-6-[(R,S)-(1-phenyl-2-hydroxyethyl)amino]-8-azapurine, 2-chloro-6-[(R,S)-(1-phenyl-2-hydroxyethyl)amino]-8-azapurine, 2-[1-(hydroxymethyl)propylamino]-6-benzylamino-8-azapurine, 2-(2-aminopropylamino)-6-benzylamino-8-azapurine, 2-(2-hydroxypropylamino)-6-benzylamino-8-azapurine, 2-(2-diethylamino)-6-(4-methoxybenzylamino)-8-azapurine, 2-(2-hydroxypropylamino)-6-(3-chloroanilino)-8-azapurine, 2-(2-hydroxypropylamino)-6-(3-chloro-4-carboxyanilino)-8-azapurine, 2-[(R)-(2-(hydroxymethyl)propyrrolidin-1-yl]-6-benzylamino-8-azapurine, 2-(1(R)-isopropyl-2-hydroxyethylamino)-6-(3-chloro-4-carboxyanilino)-8-azapurine, 2-(1(R)-isopropyl-2-hydroxyethylamino)-6-benzylamino-8-azapurine, 2-(1(R)-isopropyl-2-hydroxyethylamino)-6-(3-chloroanilino)-8-azapurine, 6-benzylamino-2-(3-nitrobenzylamino)-8-azapurine, 6-benzylamino-2-(4-nitrobenzylamino)-8-azapurine, 2-(3-aminobenzylamino)-6-benzylamino-8-azapurine, 2-(4-aminobenzylamino)-6-benzylamino-8-azapurine, 6-benzylamino-2-(3-sulfamoylfenylamino)-8-azapurine, 6-benzylamino-2-(4-sulfamoylfenylamino)-8-azapurine, 6-benzylamino-2-(3-sulfamoylbenzylamino)-8-azapurine, 6-benzylamino-2-(4-sulfamoylbenzylamino)-8-azapurine, 6-benzylamino-2-(3-ureidopropylamino)-8-azapurine, 6-benzylamino-2-(2-ureidoethylamino)-8-azapurine, 6-benzylamino-2-(3-guanidinopropyl)-8-azapurine, 6-benzylamino-2-(2-guanidinoethyl)-8-azapurine, 2-benzylamino-6-(3-nitrobenzylamino)-8-azapurine, 2-benzylamino-6-(4-nitrobenzylamino)-8-azapurine, 6-(3-aminobenzylamino)-2-benzylamino-8-azapurine, 6-(4-aminobenzylamino)-2-benzylamino-8-azapurine, 2-benzylamino-6-(3-sulfamoylfenylamino)-8-azapurine, 2-benzylamino-6-(4-sulfamoylfenylamino)-8-azapurine, 2-benzylamino-6-(3-sulfamoylbenzylamino)-8-azapurine, 2-benzylamino-6-(4-sulfamoylbenzylamino)-8-azapurine, 2-benzylamino-6-(3-ureidopropylamino)-8-azapurine, 2-benzylamino-6-(2-ureidoethylamino)-8-azapurine, 2-benzylamino-6-(3-guanidinopropyl)-8-azapurine, 2-benzylamino-6-(2-guanidinoethyl)-8-azapurine, 2-[1-(hydroxymethyl)propylamino]-6-benzylamino-9-isopropyl(methyl,ethyl)-8-azapurine, 2-[((R)-2-(hydroxymethyl)pyrrolidine-1-yl)]-6-benzylamino-9-isopropyl(methyl,ethyl)-8-azapurine, 2-(2-aminopropylamino)-6-benzylamino-9-isopropyl(methyl,ethyl)-8-azapurine, 2-(2-hydroxypropylamino)-6-benzylamino-3-isopropyl(methyl,ethyl)-8-azapurine, 2-(1(R)-isopropyl-2-hydroxyethylamino)-6-benzylamino-9-isopropyl(methyl,ethyl)-8-azapurine, 2-(4-aminocyclohexylamino)-6-benzylamino-9-isopropyl(methyl,ethyl)-8-azapurine, 2-(2-aminocyclohexylamino)-6-benzylamino-9-isopropyl(methyl,ethyl)-8-azapurine, 2-[1-(hydroxymethyl)propylamino]-6-(3-acetoxybenzylamino)-9-isopropyl(methyl,ethyl)-8-azapurine, 2-[(R)-2-(hydroxymethyl)pyrrolidine-1-yl]-6-(3-acetoxybenzylamino)-9-isopropyl(methyl,ethyl)-8-azapurine, 2-(2-aminopropylamino)-6-(3-acetoxybenzylamino)-9-isopropyl(methyl,ethyl)-8-azapurine, 2-(2-hydroxypropylamino)-6-(3-acetoxybenzylamino)-9-isopropyl(methyl,ethyl)-8-azapurine, 2-(1(R)-isopropyl-2-hydroxyethylamino)-6-(3-acetoxybenzylamino)-9-isopropyl(methyl,ethyl)-8-azapurine, 2-(4-aminocyclohexylamino)-6-(3-acetoxybenzylamino)-6-isopropyl(methyl,ethyl)-8-azapurine, 2-(2-aminocyclohexylamino)-6-(3-acetoxybenzylamino)-9-isopropyl(methyl,ethyl)-8-azapurine, 2-[1-(hydroxymethyl)propylamino]-6-(2-hydroxy-3-methoxybenzylamino)-9-isopropyl(methyl,ethyl)-8-azapurine, 2-[(R)-2-(hydroxymethyl)pyrrolidine-1-yl]-6-(2-hydroxy-3-methoxybenzylamino)-9-isopropyl(methyl,ethyl)-8-azapurine, 2-(2-aminopropylamino)-6-(2-hydroxy-3-methoxybenzylamino)-9-isopropyl(methyl,ethyl)-8-azapurine, 2-(2-hydroxypropylamino)-6-(2-hydroxy-3-methoxybenzylamino)-9-isopropyl(methyl,ethyl)-8-azapurine, 2-(1(R)-isopropyl-2-hydroxyethylamino)-6-(2-hydroxy-3-methoxybenzylamino)-9-isopropyl(methyl,ethyl)-8-azapurine, 2-(4-aminocyclohexylamino)-6-(2-hydroxy-3-methoxybenzylamino)-9-isopropyl(methyl,ethyl)-8-azapurine, 2-(2-aminocyclohexylamino)-6-(2-hydroxy-3-methoxybenzylamino)-9-isopropyl-8-azapurine, 2-[1-(hydroxymethyl)propylamino]-6-(2,3-dihydroxy-4-methoxybenzylamino)-9-isopropyl(methyl,ethyl)-8-azapurine, 2-((R)-2-(hydroxymethyl)pyrrolidine-1-yl)-6-(2,3-dihydroxy-4-methoxybenzylamino)-9-isopropyl(methyl,ethyl)-8-azapurine, 2-(2-aminopropylamino)-6-(2,3-dihydroxy-4-methoxybenzylamino)-9-isopropyl(methyl,ethyl)-8-azapurine, 2-(2-hydroxypropylamino)-6-(2,3- dihydroxy-4-methoxybenzylamino)-9-isopropyl(methyl, ethyl)-8-azapurine, 2-(1(R)-isopropyl-2-hydroxyethylamino)-6-(2,3-dihydroxy-4-methoxybenzylamino)-9-isopropyl(methyl,ethyl)-8-azapurine, 2-(4-aminocyclohexylamino)-6-(2,3-dihydroxy-4-methoxybenzylamino)-9-isopropyl(methyl,ethyl)-8-azapurine, 2-(2-aminocyclohexylamino)-6-(2,3-dihydroxy-4-methoxybenzylamino)-9-isopropyl(methyl,ethyl)-8-azapurine, 2-[1-(hydroxymethyl)propylamino]-6-(2,5-dihydroxy-4-methoxybenzylamino)-9-isopropyl(methyl, ethyl)-8-azapurine, 2-[(R)-2-(hydroxymethyl)pyrrolidine-1-yl]-6-(2,5-dihydroxy-4-methoxybenzylamino)-9-isopropyl (methyl,ethyl)-8-azapurine, 2-(2-aminopropylamino)-6-(2,5-dihydroxy-4-methoxybenzylamino)-9-isopropyl(methyl, ethyl)-8-azapurine, 2-(2-hydroxypropylamino)-6-(2,5-dihydroxy-4-methoxybenzylamino)-9-isopropyl(methyl, ethyl)-8-azapurine, 2-(1(R)-isopropyl-2-hydroxyethylamino)-6-(2,5-dihydroxy-4-methoxybenzylamino)-9-isopropyl(methyl,ethyl)-8-azapurine, 2-(4-aminocyclohexylamino)-6-(2,5-dihydroxy-4-methoxybenzylamino)-9-isopropyl(methyl,ethyl)-8-azapurine, 2-(2-aminocyclohexylamino)-6-(2,5-dihydroxy-4-methoxybenzylamino)-9-isopropyl(methyl,ethyl)-8-azapurine, 2-[1-(hydroxymethyl)propylamino]-6-(2,6-dihydroxy-4-methoxybenzylamino)-9-isopropyl(methyl, ethyl)-8-azapurine, 2-[(R)-2-(hydroxymethyl)pyrrolidine-1-yl]-6-(2,6-dihydroxy-4-methoxybenzylamino)-9-isopropyl (methyl,ethyl)-8-azapurine, 2-(2-aminopropylamino)-6-(2, 6-dihydroxy-4-methoxybenzylamino)-9-isopropyl(methyl, ethyl)-8-azapurine, 2-(2-hydroxypropylamino)-6-(2,6-dihydroxy-4-methoxybenzylamino)-9-isopropyl(methyl, ethyl)-8-azapurine, 2-(1(R)-isopropyl-2-hydroxyethylamino)-6-(2,6-dihydroxy-4-methoxybenzylamino)-9-isopropyl(methyl,ethyl)-8-azapurine, 2-(4-aminocyclohexylamino)-6-(2,6-dihydroxy-4-methoxybenzylamino)-9-isopropyl(methyl,ethyl)-8-azapurine, 2-(2-aminocyclohexylamino)-6-(2,6-dihydroxy-4-methoxybenzylamino)-9-isopropyl(methyl,ethyl)-8-azapurine, 2-[1-(hydroxymethyl)propylamino]-6-(2,3-dihydroxy-4-chlorobenzylamino)-9-isopropyl(methyl, ethyl)-8-azapurine, 2-[(R)-2-(hydroxymethyl)pyrrolidine-1-yl]-6-(2,3-dihydroxy-4-chlorobenzylamino)-9-isopropyl (methyl,ethyl)-8-azapurine, 2-(2-aminopropylamino)-6-(2, 3-dihydroxy-4-chlorobenzylamino)-9-isopropyl(methyl, ethyl)-8-azapurine, 2-(2-hydroxypropylamino)-6-(2,3-dihydroxy-4-chlorobenzylamino)-9-isopropyl(methyl, ethyl)-8-azapurine, 2-(1(R)-isopropyl-2-hydroxyethylamino)-6-(2,3-dihydroxy-4-chlorobenzylamino)-9-isopropyl(methyl,ethyl)-8-azapurine, 2-(4-aminocyclohexylamino)-6-(2,3-dihydroxy-4-chlorobenzylamino)-9-isopropyl(methyl,ethyl)-8-azapurine, 2-(2-aminocyclohexylamino)-6-(2,3-dihydroxy-4-chlorobenzylamino)-9-isopropyl(methyl,ethyl)-8-azapurine, 2-[1-(hydroxymethyl)propylamino]-6-(2,5-dihydroxy-4-chlorobenzylamino)-9-isopropyl(methyl,ethyl)-8-azapurine, 2-[(R)-2-(hydroxymethyl)pyrrolidine-1-yl]-6-(2,5-dihydroxy-4-chlorobenzylamino)-9-isopropyl(methyl,ethyl)-8-azapurine, 2-(2-aminopropylamino)-6-(2,5-dihydroxy-4-chlorobenzylamino)-9-isopropyl(methyl,ethyl)-8-azapurine, 2-(2-hydroxypropylamino)-6-(2,5-dihydroxy-4-chlorobenzylamino)-9-isopropyl(methyl,ethyl)-8-azapurine, 2-(1(R)-isopropyl-2-hydroxyethylamino)-6-(2,5-dihydroxy-4-chlorobenzylamino)-9-isopropyl(methyl,ethyl)-8-azapurine, 2-(4-aminocyclohexylamino)-6-(2,5-dihydroxy-4-chlorobenzylamino)-9-isopropyl(methyl,ethyl)-8-azapurine, 2-[1-(hydroxymethyl)propylamino]-6-(2,6-dihydroxy-4-chlorobenzylamino)-9-isopropyl(methyl,ethyl)-8-azapurine, 2-[(R)-2-(hydroxymethyl)pyrrolidine-1-yl]-6-(2,6-dihydroxy-4-chlorobenzylamino)-9-isopropyl(methyl,ethyl)-8-azapurine, 2-(2-aminopropylamino)-6-(2,6-dihydroxy-4-chlorobenzylamino)-9-isopropyl(methyl,ethyl)-8-azapurine, 2-(2-hydroxypropylamino)-6-(2,6-dihydroxy-4-chlorobenzylamino)-9-isopropyl(methyl,ethyl)-8-azapurine, 2-(1(R)-isopropyl-2-hydroxyethylamino)-6-(2,6-dihydroxy-4-chlorobenzylamino)-9-isopropyl-8-azapurine, 2-(4-aminocyclohexylamino)-6-(2,6-dihydroxy-4-chlorobenzylamino)-9-isopropyl(methyl,ethyl)-8-azapurine, 2-(2-aminocyclohexylamino)-6-(2,6-dihydroxy-4-chlorobenzylamino)-9-isopropyl(methyl,ethyl)-8-azapurine, 2-(2-aminocyclohexylamino)-6-(2,6-dihydroxy-4-chlorobenzylamino)-9-isopropyl(methyl,ethyl)-8-azapurine, 2-[1-(hydroxymethyl)propylamino]-6-(2-acetoxybenzylamino)-9-isopropyl(methyl,ethyl)-8-azapurine, 2-[(R)-2-(hydroxymethyl)pyrrolidine-1-yl]-6-(2-acetoxybenzylamino)-9-isopropyl(methyl,ethyl)-8-azapurine, 2-(2-aminopropylamino)-6-(2-acetoxybenzylamino)-9-isopropyl (methyl,ethyl)-8-azapurine, 2-(2-hydroxypropylamino)-6-(2-acetoxybenzylamino)-9-isopropyl(methyl,ethyl)-8-azapurine, 2-(1(R)-isopropyl-2-hydroxyethylamino)-6-(2-acetoxybenzylamino)-9-isopropyl(methyl,ethyl)-8-azapurine, 2-(4-aminocyclohexylamino)-6-(2-acetoxybenzylamino)-9-isopropyl(methyl,ethyl)-8-azapurine, 2-(2-aminocyclohexylamino)-6-(2-acetoxybenzylamino)-9-isopropyl(methyl,ethyl)-8-azapurine, 2-[1-(hydroxymethyl)propylamino]-6-(2-aminobenzylamino)-9-isopropyl(methyl,ethyl)-8-azapurine, 2-[(R)-2-(hydroxymethyl)pyrrolidine-1-yl]-6-(2-aminobenzylamino)-9-isopropyl(methyl,ethyl)-8-azapurine, 2-(2-aminopropylamino)-6-(2-aminobenzylamino)-9-isopropyl(methyl,ethyl)-8-azapurine, 2-(2-hydroxypropylamino)-6-(2-aminobenzylamino)-9-isopropyl(methyl,ethyl)-8-azapurine, 2-(1(R)-isopropyl-2-hydroxyethylamino)-6-(2-aminobenzylamino)-9-isopropyl(methyl,ethyl)-8-azapurine, 2-(4-aminocyclohexylamino)-6-(2-aminobenzylamino)-9-isopropyl (methyl,ethyl)-8-azapurine, 2-(2-aminocyclohexylamino)-6-(2-aminobenzylamino)-9-isopropyl(methyl,ethyl)-8-azapurine, 2-[1-(hydroxymethyl)propylamino]-6-(2-amino-6-chlorobenzylamino)-9-isopropyl(methyl,ethyl)-8-azapurine, 2-[(R)2-(hydroxymethyl)pyrrolidine-1-yl]-6-(2-amino-6-chlorobenzylamino)-9-isopropyl(methyl,ethyl)-8-azapurine, 2-(2-aminopropylamino)-6-(2-amino-6-chlorobenzylamino)-9-isopropyl(methyl,ethyl)-8-azapurine, 2-(2-hydroxypropylamino)-6-(2-amino-6-chlorobenzylamino)-9-isopropyl(methyl,ethyl)-8-azapurine, 2-(1(R)-isopropyl-2-hydroxyethylamino)-6-(2-amino-6-chlorobenzylamino)-9-isopropyl(methyl,ethyl)-8-azapurine, 2-(4-aminocyclohexylamino)-6-(2-amino-6-chlorobenzylamino)-9-isopropyl(methyl,ethyl)-8-azapurine, 2-(2-aminocyclohexylamino)-6-(2-amino-6-chlorobenzylamino)-9-isopropyl(methyl,ethyl)-8-azapurine, 2-[1-(hydroxymethyl)propylamino]-6-(3-amino-4-chlorobenzylamino)-9-isopropyl(methyl,ethyl)-8-azapurine, 2-[(R)-2-(hydroxymethyl)pyrrolidine-1-yl]-6-(3-amino-4-chlorobenzylamino)-9-isopropyl(methyl,ethyl)-8-azapurine, 2-(2-aminopropylamino)-6-(3-amino-4-chlorobenzylamino)-9-isopropyl(methyl,ethyl)-8-azapurine, 2-(2-hydroxypropylamino)-6-(3-amino-4-chlorobenzylamino)-9-isopropyl(methyl,ethyl)-8-azapurine, 2-(1(R)-isopropyl-2-hydroxyethylamino)-6-(3-amino-4-chlorobenzylamino)-9-isopropyl(methyl,ethyl)-8-azapurine, 2-(4-aminocyclohexylamino)-6-(3-amino-4-chlorobenzylamino)-9-isopropyl(methyl,ethyl)-8-azapurine, 2-(2-aminocyclohexylamino)-6-(3-amino-4-chlorobenzylamino)-9-isopropyl(methyl,ethyl)-8-azapurine, 2-[1-(hydroxymethyl)propylamino]-6-(3-acetylbenzylamino)-9-isopropyl(methyl,ethyl)-8-azapurine, 2-[(R)-2-(hydroxymethyl)pyrrolidine-1-yl]-6-(3-acetylbenzylamino)-9-isopropyl(methyl,ethyl)-8-azapurine, 2-(2-aminopropylamino)-6-(3-acetylbenzylamino)-9-isopropyl(methyl,ethyl)-8-azapurine, 2-(2-hydroxypropylamino)-6-(3-acetylbenzylamino)-9-isopropyl(methyl,ethyl)-8-azapurine, 2-(1(R)-isopropyl-2-hydroxyethylamino)-6-(3-acetylbenzylamino)-9-isopropyl(methyl,ethyl)-8-azapurine, 2-(4-aminocyclohexylamino)-6-(3-acetylbenzylamino)-9-isopropyl(methyl,ethyl)-8-azapurine, 2-(2-aminocyclohexylamino)-6-(3-acetylbenzylamino)-9-isopropyl(methyl,ethyl)-8-azapurine, 2-[1-(hydroxymethyl)propylamino]-6-(2-acetylbenzylamino)-9-isopropyl(methyl,ethyl)-8-azapurine, 2-[(R)-2-(hydroxymethyl)pyrrolidine-1-yl]-6-(2-acetylbenzylamino)-9-isopropyl(methyl,ethyl)-8-azapurine, 2-(2-aminopropylamino)-6-(2-acetylbenzylamino)-9-isopropyl(methyl,ethyl)-8-azapurine, 2-(2-hydroxypropylamino)-6-(2-acetylbenzylamino)-9-isopropyl(methyl,ethyl)-8-azapurine, 2-(1(R)-isopropyl-2-hydroxyethylamino)-6-(2-acetylbenzylamino)-9-isopropyl(methyl,ethyl)-8-azapurine, 2-(4-aminocyclohexylamino)-6-(2-acetylbenzylamino)-9-isopropyl(methyl,ethyl)-8-azapurine, 2-(2-aminocyclohexylamino)-6-(2-acetylbenzylamino)-9-isopropyl(methyl,ethyl)-8-azapurine, 2-[1-(hydroxymethyl)propylamino]-6-anilino-9-isopropyl(methylethyl)-8-azapurine, 2-[(R)-2-(hydroxymethyl)pyrrolidine-1-yl]-6-anilino-9-isopropyl(methyl,ethyl)-8-azapurine, 2-(2-aminopropylamino)-6-anilino-9-isopropyl(methyl,ethyl)-8-azapurine, 2-(2-hydroxypropylamino)-6-anilino-9-isopropyl(methyl,ethyl)-8-azapurine, 2-(1(R)-isopropyl-2-hydroxyethylamino)-6-anilino-9-isopropyl(methyl,ethyl)-8-azapurine, 2-(4-aminocyclohexylamino)-6-anilino-9-isopropyl(methyl,ethyl)-8-azapurine, 2-(2-aminocyclohexylamino)-6-anilino-9-isopropyl(methyl,ethyl)-8-azapurine, 2-[1-(hydroxymethyl)propylamino]-6-(3-chloroanilino)-9-isopropyl(methyl,ethyl)-8-azapurine, 2-[(R)-2-(hydroxymethyl)pyrrolidine-1-yl]-6-(3-chloroanilino)-9-isopropyl(methyl,ethyl)-8-azapurine, 2-(2-aminopropylamino)-6-(3-chloroanilino)-9-isopropyl(methyl,ethyl)-8-azapurine, 2-(2-hydroxypropylamino)-6-(3-chloroanilino)-9-isopropyl(methyl,ethyl)-8-azapurine, 2-(1(R)-isopropyl-2-hydroxyethylamino)-6-(3-chloroanilino)-9-isopropyl(methyl,ethyl)-8-azapurine, 2-(4-aminocyclohexylamino)-6-(3-chloroanilino)-9-isopropyl(methyl,ethyl)-8-azapurine, 2-(2-aminocyclohexylamino)-6-(3-chloroanilino)-9-isopropyl(methyl,ethyl)-8-azapurine, 2-[1-(hydroxymethyl)propylamino]-6-(4-chloroanilino)-9-isopropyl(methyl,ethyl)-8-azapurine, azapurine, 2-[(R)(2-hydroxymethyl)pyrrolidine-1-yl]-6-(4-chloroanilino)-9-isopropyl(methyl,ethyl)-8-azapurine, 2-(2-aminopropylamino)-6-(4-chloroanilino)-9-isopropyl(methyl,ethyl)-8-azapurine, 2-(2-hydroxypropylamino)-6-(4-chloroanilino)-9-isopropyl(methyl,ethyl)-8-azapurine, 2-(1(R)-isopropyl-2-hydroxyethylamino)-6-(4-chloroanilino)-9-isopropyl(methyl,ethyl)-8-azapurine, 2-(4-aminocyclohexylamino)-6-(4-chloroanilino)-9-isopropyl(methyl,ethyl)-8-azapurine, 2-(2-aminocyclohexylamino)-6-(4-chloroanilino)-9-isopropyl(methyl,ethyl)-8-azapurine, 2-[1-(hydroxymethyl)propylamino]-6-(4-bromoanilino)-9-isopropyl(methyl,ethyl)-8-azapurine, 2-[(R)-2-(hydroxymethyl)pyrrolidine-1-yl]-6-(4-bromoanilino)-9-isopropyl(methyl,ethyl)-8-azapurine, 2-(2-aminopropylamino)-6-(4-bromoanilino)-9-isopropyl(methyl,ethyl)-8-azapurine, 2-(2-hydroxypropylamino)-6-(4-bromoanilino)-9-isopropyl(methyl,ethyl)-8-azapurine, 2-(1(R)-isopropyl-2-hydroxyethylamino)-6-(4-bromoanilino)-9-isopropyl(methyl,ethyl)-8-azapurine, 2-(4-aminocyclohexylamino)-6-(4-bromoanilino)-9-isopropyl(methyl,ethyl)-8-azapurine, 2-(2-aminocyclohexylamino)-6-(4-bromoanilino)-9-isopropyl(methyl,ethyl)-8-azapurine, 2-[1-(hydroxymethyl)propylamino]-6-(3-chloro-5-aminoanilino)-9-isopropyl(methyl,ethyl)-8-azapurine, 2-[(R)-2-(hydroxymethyl)pyrrolidine-1-yl]-6-(3-chloro-5-aminoanilino)-9-isopropyl(methyl,ethyl)-8-azapurine, 2-(2-aminopropylamino)-6-(3-chloro-5-aminoanilino)-9-isopropyl(methyl,ethyl)-8-azapurine, 2-(2-hydroxypropylamino)-6-(3-chloro-5-aminoanilino)-9-isopropyl(methyl,ethyl)-8-azapurine, 2-(1(R)-isopropyl-2-hydroxyethylamino)-6-(3-chloro-5-aminoanilino)-9-isopropyl(methyl,ethyl)-8-azapurine, 2-(4-aminocyclohexylamino)-6-(3-chloro-5-aminoanilino)-9-isopropyl(methyl,ethyl)-8-azapurine, 2-(2-aminocyclohexylamino)-6-(3-chloro-5-aminoanilino)-9-isopropyl(methyl,ethyl)-8-azapurine, 2-[1-(hydroxymethyl)propylamino]-6-(3-chloro-4-carboxyanilino)-9-isopropyl(methyl,ethyl)-8-azapurine, 2-[(R)-2-(hydroxymethyl)pyrrolidine-1-yl]-6-(3-chloro-4-carboxyanilino)-9-isopropyl(methyl,ethyl)-8-azapurine, 2-(2-aminopropylamino)-6-(3-chloro-4-carboxyanilino)-9-isopropyl(methyl,ethyl)-8-azapurine, 2-(2-hydroxypropylamino)-6-(3-chloro-4-carboxyanilino)-9-isopropyl(methyl,ethyl)-8-azapurine, 2-(1(R)-isopropyl-2-hydroxyethylamino)-6-(3-chloro-4-carboxyanilino)-9-isopropyl(methyl,ethyl)-8-azapurine, 2-(4-aminocyclohexylamino)-6-(3-chloro-4-carboxyanilino)-9-isopropyl(methyl,ethyl)-8-azapurine, 2-(2-aminocyclohexylamino)-6-(3-chloro-4-carboxyanilino)-9-isopropyl(methyl,ethyl)-8-azapurine, 5-[1-(hydroxymethyl)propylamino]-7-(3-carboxy-4-chloroanilino)-3-isopropyl(methyl,ethyl)-8-azapurine, 2-[(R)-2-(hydroxymethyl)pyrrolidine-1-yl]-6-(3-carboxy-4-chloroanilino)-9-isopropyl(methyl,ethyl)-8-azapurine, 2-(2-aminopropylamino)-6-(3-carboxy-4-chloroanilino)-9-isopropyl(methyl,ethyl)-8-azapurine, 2-(2-hydroxypropylamino)-6-(3-carboxy-4-chloroanilino)-9-isopropyl(methyl,ethyl)-8-azapurine, 2-(1(R)-isopropyl-2-hydroxyethylamino)-6-(3-carboxy-4-chloroanilino)-9-isopropyl(methyl,ethyl)-8-azapurine, 2-(4-aminocyclohexylamino)-6-(3-carboxy-4-chloroanilino)-9-isopropyl(methyl,ethyl)-8-azapurine, 2-(2-aminocyclohexylamino)-6-(3-carboxy-4-chloroanilino)-9-isopropyl(methyl,ethyl)-8-azapurine, 2-[1-(hydroxymethyl)propylamino]-6-(3-amino-4-chloroanilino)-9-isopropyl(methyl,ethyl)-8-azapurine, 2-[(R)2-(hydroxymethyl)pyrrolidine-1-yl]-6-(3-amino-4-chloroanilino)-9-isopropyl(methyl,ethyl)-8-azapurine, 2-(2-aminopropylamino)-6-(3-amino-4-chloroanilino)-9-isopropyl(methyl,ethyl)-8-azapurine, 2-(2-hydroxypropylamino)-6-(3-amino-4-chloroanilino)-8-isopropyl(methyl,ethyl)-8-azapurine, 2-(1(R)-isopropyl-2-hydroxyethylamino)-6-(3-amino-4-chloroanilino)-9-isopropyl(methyl,ethyl)-8-azapurine, 2-(4-aminocyclohexylamino)-6-(3-amino-4-chloroanilino)-9-isopropyl(methyl,ethyl)-8-azapurine, 2-(2-aminocyclohexylamino)-6-(3-amino-4-chloroanilino)-9-isopropyl(methyl,ethyl)-8-azapurine, 2-[1-(hydroxymethyl)propylamino]-6-(3-chloro-4-aminoanilino)-9-isopropyl(methyl,ethyl)-8-azapurine, 2-[(R)2-(hydroxymethyl)pyrrolidine-1-yl]-6-(3-chloro-4-aminoanilino)-9-isopropyl(methyl,ethyl)-8-azapurine, 2-(2-aminopropylamino)-6-(3-chloro-4-aminoanilino)-9-isopropyl(methyl,ethyl)-8-azapurine, 2-(2-hydroxypropylamino)-6-(3-chloro-4-aminoanilino)-9-isopropyl(methyl,ethyl)-8-azapurine, 2-(1(R)-isopropyl-2-hydroxyethylamino)-6-(3-chloro-4- aminoanilino)-9-isopropyl(methyl,ethyl)-8-azapurine, 2-(4-aminocyclohexylamino)-6-(3-chloro-4-aminoanilino)-9-isopropyl(methyl,ethyl)-8-azapurine, 2-(2-aminocyclohexylamino)-6-(3-chloro-4-aminoanilino)-9-isopropyl(methyl,ethyl)-8-azapurine, 2-[1-(hydroxymethyl) propylamino]-6-(3-carboxy-4-hydroxyanilino)-9-isopropyl (methyl,ethyl)-8-azapurine, 2-[(R)2-(hydroxymethyl) pyrrolidine-1-yl]-6-(3-carboxy-4-hydroxyanilino)-9-isopropyl(methyl,ethyl)-8-azapurine, 2-(2-aminopropylamino)-6-(3-carboxy-4-hydroxyanilino)-9-isopropyl(methyl,ethyl)-8-azapurine, 2-(2-hydroxypropylamino)-6-(3-carboxy-4-hydroxyanilino)-9-isopropyl(methyl,ethyl)-8-azapurine, 2-(1(R)-isopropyl-2-hydroxyethylamino)-6-(3-carboxy-4-hydroxyanilino)-9-isopropyl(methyl,ethyl)-8-azapurine, 2-(4-aminocyclohexylamino)-6-(3-carboxy-4-hydroxyanilino)-9-isopropyl(methyl,ethyl)-8-azapurine, 2-(2-aminocyclohexylamino)-6-(3-carboxy-4-hydroxyanilino)-9-isopropyl(methyl,ethyl)-8-azapurine, 2-(2-hydroxypropylamino)-6-[N-(3,4-dihydroxybenzyl)-N-methyl]amino-9-isopropyl(methyl,ethyl)-8-azapurine, 2-(1(R)-isopropyl-2-hydroxyethylamino)-6-[N-(3,4-dihydroxybenzyl)-N-methyl]amino-9-isopropyl(methyl, ethyl)-8-azapurine, 2-(2-hydroxypropylamino)-6-[1-(3,4-dihydroxyphenyl)ethyl]amino-9-isopropyl(methyl,ethyl)-8-azapurine, 2-(1(R)-isopropyl-2-hydroxyethylamino)-6-[1-(3,4-dihydroxyphenyl)ethyl]amino-9-isopropyl(methyl, ethyl)-8-azapurine, 2-(1(R)-isopropyl-2-hydroxyethylamino)-6-[N-(2-(3,4-dihydroxyfenyl)ethyl)-N-methyl]amino-9-isopropyl(methyl,ethyl)-8-azapurine, 2-(1(R)-isopropyl-2-hydroxyethylamino)-6-[(R)-(1-phenyl-2-hydroxyethyl)amino]-9-isopropyl(methyl,ethyl)-8-azapurine, 2-(1(R)-isopropyl-2-hydroxyethylamino)-6-[(R,S)-(1-phenyl-2-hydroxyethyl)amino]-9-isopropyl(methyl, ethyl)-8-azapurine, 2-chloro-6-[(R,S)-(1-phenyl-2-hydroxyethyl)amino]-9-isopropyl(methyl,ethyl)-8-azapurine, 2-[1-(hydroxymethyl)propylamino]-6-benzylamino-9-isopropyl(methyl,ethyl)-8-azapurine, 2-(2-aminopropylamino)-6-benzylamino-9-isopropyl(methyl, ethyl)-8-azapurine, 2-(2-hydroxypropylamino)-6-benzylamino-9-isopropyl(methyl,ethyl)-8-azapurine, 2-(2-diethylamino)-6-(4-methoxybenzylamino)-9-isopropyl (methyl,ethyl)-8-azapurine, 2-(2-hydroxypropylamino)-6-(3-chloroanilino)-9-isopropyl(methyl,ethyl)-8-azapurine, 2-(2-hydroxypropylamino)-6-(3-chloro-4-carboxyanilino)-9-isopropyl(methyl,ethyl)-8-azapurine, 2-[(R)-(2-(hydroxymethyl)propyrrolidin-1-yl]-6-benzylamino-9-isopropyl(methyl,ethyl)-8-azapurine, 2-(1(R)-isopropyl-2-hydroxyethylamino)-6-(3-chloro-4-carboxyanilino)-9-isopropyl(methyl,ethyl)-8-azapurine, 2-(1(R)-isopropyl-2-hydroxyethylamino)-6-benzylamino-9-isopropyl(methyl, ethyl)-8-azapurine, 2-(1(R)-isopropyl-2-hydroxyethylamino)-6-(3-chloroanilino)-9-isopropyl (methyl,ethyl)-8-azapurine.

Salts/Esters

The compounds of the invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of compounds of the invention. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those agents, and mixtures thereof. The terms used in the claims encompass these forms, provided said forms retain the appropriate functional activity (though not necessarily to the same degree).

The present invention also includes all suitable isotopic variations of the agent or pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes the use of solvate forms of the compounds of the present invention. The terms used in the claims encompass these forms.

Polymorphs

The invention furthermore relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes the compounds of the present invention in prodrug form. Such prodrugs are generally compounds of the invention in which one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Utility

The novel compounds of this invention per se or as intermediates in the preparation of novel compound having a wide variety of diagnostic, therapeutic and industrial utilities. The compounds of the present invention have been found to possess anti-proliferative activity and are therefore believed to be of use in the treatment of proliferative disorders, such as cancers, leukaemias or other disorders associated with uncontrolled cellular proliferation such as psoriasis and restenosis.

As defined herein, an anti-proliferative effect within the scope of the present invention may be demonstrated by the ability to inhibit cell proliferation in an in vitro whole cell assay, for example using any of the cell lines A549, HeLa, HT-29, MCF7, Saos-2, CCRF-CEM, HL-60 and K-562, or by showing kinase inhibition in an appropriate assay. These assays, including methods for their performance, are described in more detail in the accompanying Examples. Using such assays it may be determined whether a compound is anti-proliferative in the context of the present invention.

One preferred embodiment of the present invention therefore relates to the use of one or more compounds of the invention in the preparation of a medicament for treating a proliferative disorder.

As used herein the phrase "preparation (or manufacture) of a medicament" includes the use of a compound of the invention directly as the medicament in addition to its use in a screening programme for further therapeutic agents or in any stage of the manufacture of such a medicament.

The term "proliferative disorder" is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, anti-parasitic disorders such as malaria, emphysema and alopecia. In these disorders, the compounds of the present invention may induce apoptosis or maintain stasis within the desired cells as required. Preferably, the proliferative disorder is a cancer or leukaemia.

In another preferred embodiment, the proliferative disorder is psoriasis.

The compounds of the invention may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of the invention may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

A further aspect of the invention relates to a method of treating a proliferative disease, said method comprising administering to a mammal a therapeutically effective amount of a compound of formula 1.

In a preferred embodiment of this aspect, the proliferative disorder is cancer or leukaemia.

In an even more preferred embodiment of this aspect, the compound is administered in an amount sufficient to inhibit at least one CDK enzyme.

Preferably, the compound of the invention is administered in an amount sufficient to inhibit at least one of CDK1, CDK2, CDK3, CDK4, CDK6, CDK7, CDK8 and/or CDK9.

More preferably, the compound of the invention is administered in an amount sufficient to inhibit at least one of CDK2 and/or CDK4. Even more preferably, the CDK enzyme is CDK2.

In one preferred embodiment of this aspect, the compound is administered orally.

Another aspect of the invention relates to the use of a compound of formula 1 as an anti-mitotic agent.

Yet another aspect of the invention relates to the use of a compound of formula 1 for treating a neurodegenerative disorder. Preferably, the neurodegenerative disorder is neuronal apoptosis.

Another aspect of the invention relates to the use of a compound of formula 1 as an antiviral agent.

Thus, another aspect of the invention relates to the use of a compound of the invention in the preparation of a medicament for treating a viral disorder, such as human cytomegalovirus (HCMV), herpes simplex virus type 1 (HSV-1), human immunodeficiency virus type 1 (HIV-1), and varicella zoster virus (VZV).

In a more preferred embodiment of the invention, the compound of the invention is administered in an amount sufficient to inhibit one or more of the host cell CDKs involved in viral replication, i.e. CDK2, CDK7, CDK8, and CDK9 [Wang D, De la Fuente C, Deng L, Wang L, Zilberman I, Eadie C, Healey M, Stein D, Denny T, Harrison L E, Meijer L, Kashanchi F. Inhibition of human immunodeficiency virus type 1 transcription by chemical cyclin-dependent kinase inhibitors. J. Virol. 2001; 75: 7266-7279].

As defined herein, an anti-viral effect within the scope of the present invention may be demonstrated by the ability to inhibit CDK2, CDK7, CDK8 or CDK9.

In a particularly preferred embodiment, the invention relates to the use of one or more compounds of the invention in the treatment of a viral disorder which is CDK dependent or sensitive. CDK dependent disorders are associated with an above normal level of activity of one or more CDK enzymes. Such disorders preferably associated with an abnormal level of activity of CDK2, CDK7, CDK8 and/or CDK9. A CDK sensitive disorder is a disorder in which an aberration in the CDK level is not the primary cause, but is downstream of the primary metabolic aberration. In such scenarios, CDK2, CDK7, CDK8 and/or CDK9 can be said to be part of the sensitive metabolic pathway and CDK inhibitors may therefore be active in treating such disorders.

Another aspect of the invention relates to the use of compounds of the invention, or pharmaceutically acceptable salts thereof, in the preparation of a medicament for treating diabetes.

In a particularly preferred embodiment, the diabetes is type II diabetes.

GSK3 is one of several protein kinases that phosphorylate glycogen synthase (GS). The stimulation of glycogen synthesis by insulin in skeletal muscle results from the dephosphorylation and activation of GS. GSK3's action on GS thus results in the latter's deactivation and thus suppression of the conversion of glucose into glycogen in muscles.

Type II diabetes (non-insulin dependent diabetes mellitus) is a multi-factorial disease. Hyperglycaemia is due to insulin resistance in the liver, muscles, and other tissues, coupled with impaired secretion of insulin. Skeletal muscle is the main site for insulin-stimulated glucose uptake, there it is either removed from circulation or converted to glycogen. Muscle glycogen deposition is the main determinant in glucose homeostasis and type II diabetics have defective muscle glycogen storage. There is evidence that an increase in GSK3 activity is important in type II diabetes [Chen, Y. H.; Hansen, L.; Chen, M. X.; Bjorbaek, C.; Vestergaard, H.; Hansen, T.; Cohen, P. T.; Pedersen, O. *Diabetes,* 1994, 43, 1234]. Furthermore, it has been demonstrated that GSK3 is over-expressed in muscle cells of type II diabetics and that an inverse correlation exists between skeletal muscle GSK3 activity and insulin action [Nikoulina, S. E.; Ciaraldi, T. P.; Mudaliar, S.; Mohideen, P.; Carter, L.; Henry, R. R. *Diabetes,* 2000, 49, 263].

GSK3 inhibition is therefore of therapeutic significance in the treatment of diabetes, particularly type II, and diabetic neuropathy.

It is notable that GSK3 is known to phosphorylate many substrates other than GS, and is thus involved in the regulation of multiple biochemical pathways. For example, GSK is highly expressed in the central and peripheral nervous systems.

Another aspect of the invention therefore relates to the use of compounds of the invention, or pharmaceutically acceptable salts thereof, in the preparation of a medicament for treating a CNS disorders, for example neurodegenerative disorders. Preferably, the CNS disorder is Alzheimer's disease.

Tau is a GSK-3 substrate which has been implicated in the etiology of Alzheimer's disease. In healthy nerve cells, Tau co-assembles with tubulin into microtubules. However, in Alzheimer's disease, tau forms large tangles of filaments, which disrupt the microtubule structures in the nerve cell, thereby impairing the transport of nutrients as well as the transmission of neuronal messages.

Without wishing to be bound by theory, it is believed that GSK3 inhibitors may be able to prevent and/or reverse the abnormal hyperphosphorylation of the microtubule-associated protein tau that is an invariant feature of Alzheimer's disease and a number of other neurodegenerative diseases, such as progressive supranuclear palsy, corticobasal degeneration and Pick's disease. Mutations in the tau gene cause inherited forms of fronto-temporal dementia, further underscoring the relevance of tau protein dysfunction for the neurodegenerative process [Goedert, M. *Curr. Opin. Gen. Dev.,* 2001, 11, 343].

Another aspect of the invention relates to the use of compounds of the invention, or pharmaceutically acceptable salts thereof, in the preparation of a medicament for treating bipolar disorder.

Yet another aspect of the invention relates to the use of compounds of the invention, or pharmaceutically acceptable salts thereof, in the preparation of a medicament for treating a stroke.

Reducing neuronal apoptosis is an important therapeutic goal in the context of head trauma, stroke, epilepsy, and motor neuron disease [Mattson, M. P. Nat. Rev. Mol. Cell. Biol., 2000, 1, 120]. Therefore, GSK3 as a pro-apoptotic factor in neuronal cells makes this protein kinase an attractive therapeutic target for the design of inhibitory drugs to treat these diseases.

Yet another aspect of the invention relates to the use of compounds of the invention, or pharmaceutically acceptable salts thereof, in the preparation of a medicament for treating alopecia.

Hair growth is controlled by the Wnt signalling pathway, in particular Wnt-3. In tissue-culture model systems of the skin, the expression of non-degradable mutants of β-catenin leads to a dramatic increase in the population of putative stem cells, which have greater proliferative potential [Zhu, A. J.; Watt, F. M. Development, 1999, 126, 2285]. This population of stem cells expresses a higher level of non-cadherin-associated β-catenin [DasGupta, R.; Fuchs, E. Development, 1999, 126, 4557], which may contribute to their high proliferative potential. Moreover, transgenic mice overexpressing a truncated β-catenin in the skin undergo de novo hair-follicle morphogenesis, which normally is only established during embryogenesis. The ectopic application of GSK3 inhibitors may therefore be therapeutically useful in the treatment of baldness and in restoring hair growth following chemotherapy-induced alopecia.

A further aspect of the invention relates to a method of treating a GSK3-dependent disorder, said method comprising administering to a subject in need thereof, a compound according to the invention, or a pharmaceutically acceptable salt thereof, as defined above in an amount sufficient to inhibit GSK3.

Preferably, the compound of the invention, or pharmaceutically acceptable salt thereof, is administered in an amount sufficient to inhibit GSK3β.

In one embodiment of the invention, the compound of the invention is administered in an amount sufficient to inhibit at least one PLK enzyme.

The polo-like kinases (PLKs) constitute a family of serine/threonine protein kinases. Mitotic *Drosophila melanogaster* mutants at the polo locus display spindle abnormalities [Sunkel et al., *J. Cell Sci.,* 1988, 89, 25] and polo was found to encode a mitotic kinase [Llamazares et al., *Genes Dev.,* 1991, 5, 2153]. In humans, there exist three closely related PLKs [Glover et al., *Genes Dev.,* 1998, 12, 3777]. They contain a highly homologous amino-terminal catalytic kinase domain and their carboxyl termini contain two or three conserved regions, the polo boxes. The function of the polo boxes remains incompletely understood but they are implicated in the targeting of PLKs to subcellular compartments [Lee et al., *Proc. Natl. Acad. Sci. USA,* 1998, 95, 9301; Leung et al., *Nat. Struct. Biol.,* 2002, 9, 719], mediation of interactions with other proteins [Kauselmann et al., *EMBO J.,* 1999, 18, 5528], or may constitute part of an autoregulatory domain [Nigg, *Curr. Opin. Cell Biol.,* 1998, 10, 776]. Furthermore, the polo box-dependent PLK1 activity is required for proper metaphase/anaphase transition and cytokinesis [Yuan et al., *Cancer Res.,* 2002, 62, 4186; Seong et al., *J. Biol. Chem.,* 2002, 277, 32282].

Studies have shown that human PLKs regulate some fundamental aspects of mitosis [Lane et al., *J. Cell. Biol.,* 1996, 135, 1701; Cogswell et al., *Cell Growth Differ.,* 2000, 11, 615]. In particular, PLK1 activity is believed to be necessary for the functional maturation of centrosomes in late G2/early prophase and subsequent establishment of a bipolar spindle. Depletion of cellular PLK1 through the small interfering RNA (siRNA) technique has also confirmed that this protein is required for multiple mitotic processes and completion of cytokinesis [Liu et al., *Proc. Natl. Acad. Sci. USA,* 2002, 99, 8672].

In a more preferred embodiment of the invention, the compound of the invention is administered in an amount sufficient to inhibit PLK1.

Of the three human PLKs, PLK1 is the best characterized; it regulates a number of cell division cycle effects, including the onset of mitosis [Toyoshima-Morimoto et al., *Nature,* 2001, 410, 215; Roshak et al., *Cell. Signalling,* 2000, 12, 405], DNA-damage checkpoint activation [Smits et al., *Nat. Cell Biol.,* 2000, 2, 672; van Vugt et al., *J. Biol. Chem.,* 2001, 276, 41656], regulation of the anaphase promoting complex [Sumara et al., *Mol. Cell,* 2002, 9, 515; Golan et al., *J. Biol. Chem.,* 2002, 277, 15552; Kotani et al., *Mol. Cell,* 1998, 1, 371], phosphorylation of the proteasome [Feng et al., *Cell Growth Differ.,* 2001, 12, 29], and centrosome duplication and maturation [Dai et al., *Oncogene,* 2002, 21, 6195].

Specifically, initiation of mitosis requires activation of M-phase promoting factor (MPF), the complex between the cyclin dependent kinase CDK1 and B-type cyclins [Nurse, *Nature,* 1990, 344, 503]. The latter accumulate during the S and G2 phases of the cell cycle and promote the inhibitory phosphorylation of the MPF complex by WEE1, MIK1, and MYT1 kinases. At the end of the G2 phase, corresponding dephosphorylation by the dual-specificity phosphatase CDC25C triggers the activation of MPF [Nigg, *Nat. Rev. Mol. Cell Biol.,* 2001, 2, 21]. In interphase, cyclin B localizes to the cytoplasm [Hagting et al., *EMBO J.,* 1998, 17, 4127], it then becomes phosphorylated during prophase and this event causes nuclear translocation [Hagting et al., *Curr. Biol.,* 1999, 9, 680; Yang et al., *J. Biol. Chem.,* 2001, 276, 3604]. The nuclear accumulation of active MPF during prophase is thought to be important for initiating M-phase events [Takizawa et al., *Curr. Opin. Cell Biol.,* 2000, 12, 658]. However, nuclear MPF is kept inactive by WEE1 unless counteracted by CDC25C. The phosphatase CDC25C itself, localized to the cytoplasm during interphase, accumulates in the nucleus in prophase [Seki et al., *Mol. Biol. Cell,* 1992, 3, 1373; Heald et al., *Cell,* 1993, 74, 463; Dalal et al., *Mol. Cell. Biol.,* 1999, 19, 4465]. The nuclear entry of both cyclin B [Toyoshima-Morimoto et al., *Nature,* 2001, 410, 215] and CDC25C [Toyoshima-Morimoto et al., *EMBO Rep.,* 2002, 3, 341] are promoted through phosphorylation by PLK1 [Roshak et al.,

*Cell. Signalling,* 2000, 12, 405]. This kinase is an important regulator of M-phase initiation.

In one particularly preferred embodiment, the compounds of the invention are ATP-antagonistic inhibitors of PLK1.

In the present context ATP antagonism refers to the ability of an inhibitor compound to diminish or prevent PLK catalytic activity, i.e. phosphotransfer from ATP to a macromolecular PLK substrate, by virtue of reversibly or irreversibly binding at the enzyme's active site in such a manner as to impair or abolish ATP binding.

In another preferred embodiment, the compound of the invention is administered in an amount sufficient to inhibit PLK2 and/or PLK3.

Mammalian PLK2 (also known as SNK) and PLK3 (also known as PRK and FNK) were originally shown to be immediate early gene products. PLK3 kinase activity appears to peak during late S and G2 phase. It is also activated during DNA damage checkpoint activation and severe oxidative stress. PLK3 also plays an important role in the regulation of microtubule dynamics and centrosome function in the cell and deregulated PLK3 expression results in cell cycle arrest and apoptosis [Wang et al., *Mol. Cell. Biol.,* 2002, 22, 3450]. PLK2 is the least well understood homologue of the three PLKs. Both PLK2 and PLK3 may have additional important post-mitotic functions [Kauselmann et al., *EMBO J.,* 1999, 18, 5528].

Another aspect of the invention relates to the use of a compound of formula 1 for inhibiting a protein kinase.

In a preferred embodiment of this aspect, the protein kinase is a cyclin dependent kinase.

Preferably, the protein kinase is CDK1, CDK2, CDK3, CDK4, CDK6, CDK7, CDK8 or CDK9, more preferably CDK2.

A further aspect of the invention relates to a method of inhibiting a protein kinase, said method comprising contacting said protein kinase with a compound of formula 1.

In a preferred embodiment of this aspect, the protein kinase is a cyclin dependent kinase, even more preferably CDK2.

The compounds of this invention are suitable as intermediates for use in the preparation of affinity absorption matrices that harness the chemical properties of the compound's substituent groups. For example, the phosphonate groups in matrix bound form are useful in the chromatographic separation of positively charged molecules. Other immobilised examples of the compounds herein are useful in purifying proteins, e.g., cell cycle enzymes (cdk's), enzymes involved in recognition of the compound of this invention, e.g. transport proteins. Suitable methods of incorporation of the compounds of this invention into polymeric resins will be readily apparent to the skilled artisan, for instance the compounds are incorporated by cross-linking hydroxyl groups of the phosphonate or hydroxymethyl substituents using cross-linking agents heretofore known. Linking through a group other than the heterocyclic base will produce a resin useful in hydrophobic affinity chromatography.

The compounds of the formula I and their pharmaceutically acceptable salts inhibit selectively the enzyme p34$^{cdc2}$/cyclin B kinase and related cdks (cdk2, cdk5, cdk7, cdk9, erk1, erk2).

In another embodiment, this invention is a method for inhibiting cdks and cell proliferation and/or for inducing apoptosis in mammals comprising administering a therapeutically effective amount of the composition of claim 1 to the mammal. The cdk inhibiting molecules are useful for treating disorders, some of them involving cell proliferation, such as cancer, restenosis, rheumatoid arthritis, lupus, type I diabetes, multiple sclerosis, Alzheimer's disease, growth of parasites (animal, protists), graft rejection (host versus graft disease), graft versus host disease, and gout.

In still another embodiment, this invention is a composition useful for treating fungal infections (fungi) in humans, animals and plants.

Di- and trisubstituted 8-azapurine derivatives result in the acquisition of extremely high potency against DNA viruses on the part of the defined compounds. Such compounds otherwise have been considered to have little or no activity against DNA viruses.

Moreover, surprisingly the chirally enriched or pure (S)-enantiomer is antivirally active. Heretofore, only the (R)-enantiomer was notably antivirally active, and then only against the retroviruses. An important aspect of the present invention is a methods for inhibiting proliferation of a DNA virus dependent upon events associated with cell proliferation for replication. The DNA virus includes any of the herpesvirus family, and most particularly human cytomegalovirus. The method involves administering prophylactically or therapeutically effective amount of a cyclin-dependent kinase inhibitor to a patient or animal. The therapeutically effective amount is that sufficient to inhibit cellular CDK activity to extent impending viral replication. Other herpesviruses such as herpes simplex, for example, and other cytomegalovirus are also treatable by the procedures of the present invention.

In addition to other cdc2-related kinases, this kinase controls certain steps of cell division cycles, in particular the transition from $G_1$ phase into the S phase and in particular the transition from the $G_2$ phase into the M-phase. Out the basis of this findings, it can be expected that the compounds of the formula I and their pharmaceutically acceptable salts can be used as antimitotic compounds and for treatment of proliferative diseases, such as cancer and restenosis. Thus in very low concentration (micromolar and lower), they are capable of inhibiting cell cycle transitions ($G_1$/S, $G_2$/M, M-phase/metaphase) carried out on the different animal bodies and embryos. Furthermore, the compounds are useful in treating auto-immune diseases, e.g. rheumatoid arthritis, lupus, type I diabetes, multiple sclerosis, etc.; in treating Alzheimer's disease, cardiovascular disease such as restenosis, graft rejection (host vs. graft disease), graft vs. host disease, gout; and in treating cancer, polycystic kidney disease and other proliferative diseases whose pathogenesis involves abnormal cell proliferation.

In addition to proliferative disorders, the treatment of differentiative disorders which result from, for example, de-differentiation of tissue which may (optionally) be accompanied by abortive reentry into mitosis. Such degenerative disorders include chronic neurodegenerative diseases of the nervous system, including Alzheimer's disease, Parkinson's disease, Huntington's chorea, amylotrophic lateral sclerosis and the like, as well as spinocerebellar degenerations. Other differentiative disorders include, for example, disorders associated with connective tissue, such as may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors.

In addition to therapeutic applications (e.g., for both human and veterinary uses) it will be apparent the subject compounds can be used as a cell culture additive for controlling proliferative and/or differentiation states of cells in vitro, for instance, by controlling the level of activation of a CDK. To illustrate, in vitro neuronal culture systems have proved to be fundamental and indispensable tools for the study of neural development, as well as the identification of neutrophic factors. Once a neuronal cell has become terminally-differentiated, it typically will not change to another terminally differentiated cell-type. However, neuronal cells can nevertheless readily lose their differentiated state. This is commonly observed when they are grown in culture from adult tissue, and when they form a blastema during regeneration. By preventing the activation of a Go/G1 CDK, the subject inhibitors can prevent mitotic progression and hence provide a means for ensuring an adequately restrictive environment in order to maintain neuronal cells at various stages of differentiations, and can be employed, for instance, in cell cultures designed to test the specific activities of trophic factors. Other tissue culture systems, which require maintenance of differentiation, will be readily apparent to those skilled in the art. In this respect, each of the CDK4 inhibitors can be used for ex vivo tissue generation, as for example, to enhance the generation of prosthetic tissue devices for implantation.

It is likely that inhibition by the compounds, of the invention of the catalytic activity of cyclin-dependent kinases in mediated by interaction of the compounds at the ATP-binding site of the enzyme. Such compounds are particularly desirable for reducing excessive cell growth, since they allow inhibition of the kinase activity regardless of the cause underlying the excessive kinase activity leading to excessive cell proliferation. Thus, the compounds of the invention are active in situations in which the excessive kinase activity results from the kinase being a mutated hyperactive, form of the kinase and situations in which the kinase is present at excessive levels. Such compounds can also block excessive kinase activity in situations in which the cyclin regulating the kinase is present at excessive levels or its binding to the kinase is enhanced. Furthermore, compounds which block kinase activity by interacting with the ATP binding site of the enzyme are also useful for inhibiting kinase activity in situations in which a natural inhibitor of cyclin-kinase complexes is mutated.

It will also be apparent that differential screening assays can be used to select for those compounds of the present invention with specificity for non-human CDK enzymes. Thus, compounds, which act specifically on eukaryotic pathogens, e.g., are anti-fungal or anti-parasitic agents can be selected from the subject benzopyranone inhibitors. To illustrate inhibitors of the *Candida* CDK kinase, CKS 1, can be used in the treatment of candidiasis- and opportunistic infection that commonly occurs in debilitated and immunosuppressed patients. CKS 1 inhibitors could be used to treat these infections in patients with leukemias and lymphomas, in people who are receiving immunosuppressive therapy, and in patients with such predisposing factors as diabetes mellitus or AIDS, where fungal infections are a particular problem.

By way of illustration, the assays described in the art can be used to screen for agents which may ultimately be useful for inhibiting at least one fungus implicated in such mycosis as candidiasis, aspergillosis, mucormycosis, blastomycosis, geotrichosis, cryptococcosis, chromoblastomycosis, coccidiodomycosis, conidiosporosis, histoplasmosis, maduromycosis, rhinosporidosis, nocaidiosis, paraactinomycosis, penicilliosis, monoliasis, or sporotrichosis. For example, if the mycotic infection to which treatment is desired is candidiasis, an assay as described above or in the appended examples can comprise comparing the relative effectiveness of a test compound on inhibiting a mammalian CDK enzyme with its effectiveness towards a CDK enzyme from yeast, such as selected from the group consisting of *Candida albicans, Candida stellatoidea, Candida tropicalis, Candida parapsilosis, Candida krusei, Candida pseudotropicalis, Candida auiller-*

*mondii*, or *Candida rugosa*. *Candida* CDK genes have been described, such as in U.S. Ser. No. 08/463,090.

Likewise, the differential screening assays can be used to identify anti-fungal agents which may have therapeutic value in the treatment of aspergillosis by making use of the CDK genes cloned from yeast such as *Aspergillus fumigatus, Aspergillus flavus, Aspergillus niger, Aspergillus nidulans*, or *Apergillus terreus*.

Likewise, where the mycotic infection is mucormycosis, the CDK assay can be derived from yeast such as *Rhizopus arrhizus, Rhizopus oryzae, Absidia corymbifera, Absidia ramosa*, or *Mucor pusillus*. Sources of other CDK enzymes include the pathogen *Pneumocystis carinii*.

In addition to such therapeutic uses, anti-fungal agents developed with such differential screening assays can be used, for example, as preservatives in foodstuff, feed supplement for promoting weight gain in livestock, or in disinfectant formulations for treatment of non-living matter, e.g., for decontaminating hospital equipment and rooms.

In similar fashion, side-by-side comparison of inhibition of a mammalian CDK and an insect CDK, such as the *Drosophilia* CDK5 gene (Hellmich et al. (1994) *FEBS Lett* 356: 317-21), will permit selection amongst the subject 8-azapurine derivatives of inhibitors, which discriminate between the human/mammalian and insect enzymes. Accordingly, the present invention expressly contemplates the use and formulations of the subject benzopyranone in insecticides, such as for use in management of insect like the fruit fly.

In yet another embodiment, certain of the subject CDK inhibitors can be selected on the basis of inhibitory specificity for plant CDK's relative to the mammalian enzyme. For example, a plant CDK can be sidposed in a differential screen with one or more of the human enzymes to select those 8-azapurine compounds of greatest selectivity for inhibiting the plant enzyme. Thus, the present invention specifically contemplates formulations of the subject CDK inhibitors for agricultural applications, such as in the form of a defoliant or the like.

This invention also concerns novel compounds that have been discovered to be potent and specific inhibitors of IκB-α kinase which prevents signal induced NF-κB activation and cytokine synthesis in vitro and in vivo. Such inhibitors are expected to inhibit synthesis of cytokines and adhesion proteins whose synthesis is transcriptionally regulated by NF-κB. Pro-inflammatory cytokines such as IL-1, IL-6, TNF and adhesion proteins (e.g. ICAM, VCAM and selections) belong to this class of molecules and have implicated in the pathogenesis of inflammatory diseases. Thus a potent inhibitor of IκB-α kinase is useful in the clinical management of diseases where the NF-κB activation is required for disease induction.

The invention also concerns novel compounds which affect the activation and/or signal transduction of α- and β-adrenergic receptors e.g. phosphatidyl turnover and cyclic AMP synthesis respectively. Activation of β-adrenergic receptors has an anti-inflammatory effect by decreasing the cytokine production of macrophages, astrocytes, and by preventing an increase in vascular permeability. On the other hand a decreased β-adrenergic receptor activation is useful in diseases like multiple sclerosis, rheumatoid arthritis. The novel compounds may also affect P2-purinergic receptor activation linked to phosphatidyl turnover and inhibition of activation of cyclic AMP synthesis or P1-purinergic receptor activation positively or negatively coupled to the activation of adenylate cyclase depending on the receptor subtype. Modulation of purinergic receptor signalling may be useful in cerebral ischaemia, stroke, treatments of neurodegenerative diseases (e.g. Parkinson's disease), renal failure, treatment of lung dysfunction, and in inhibition of cancer growth.

Studies carried out on the derivatives of the invention have demonstrated, in addition, the strong effect on apoptosis of many cancer cell lines. It has been seen that apoptosis can be induced at stage $G_1$ or $G_2$ and following damage of the DNA, some cells stop at stage $G_1$ and p53-dependent apoptotic pathway is then induced. In other situations, it seems that cells stop at $G_2$/M stage in response to damage caused to the DNA, and activation of an independent p53 apoptotic path is observed. This path has proved particularly significant in the therapy of tumours in which a less active p53 is observed. The interest is therefore assessed that by application of the derivatives of the invention, p53-independent apoptosis will be stimulated in cells, which have stopped at stage $G_2$ through damage to the DNA using agents such as mitoxantrone or cis-platinum. The cdk inhibitors of this invention can thus increase the therapeutic potential of the anti-tumour agents currently used.

The compounds of this invention also are useful as linkers or spacers in preparation of affinity absorption matrices (as opposed to functioning as affinity moieties per se as noted above), immobilised enzymes for process control, or immunoassay reagents. The compounds herein contain a multiplicity of functional groups that are suitable as sites for cross-linking desired substances. For example, it is conventional to link affinity reagents such as hormones, peptides, antibodies, drugs, and the like to insoluble substrates. These insolubilised bound reagents are employed in known fashion to absorb binding partners for the affinity reagents from manufactured preparations, diagnostic samples and other impure mixtures. Similarly, immobilised enzymes are used to perform catalytic conversions with easy recovery of enzyme. Bifunctional compounds are commonly used to link analytes to detectable groups in preparing diagnostic reagents.

Many functional groups present in the compounds of this invention are suitable for use in cross-linking. For example, the phosphonic acid is used to form esters with alcohols or amides with amines. The R groups substituted with OH, azido (which is reduced to amino if desired before cross-linking) or vinyl are exemplary suitable sites. Similarly, the amino, halo, acyl and other reactive sites found on group B are suitable. Suitable protection of reactive groups will be used where necessary while assembling the cross-linked reagent. In general, the compounds here are used by linking them through phosphonic acid or amino group to the hydroxyl or amino groups of the linking partner in the same fashion as shown herein, and covalently bound to the other binding partner through an R group. For example a first binding partner such as a steroid hormone is esterified and then this conjugate is cross-linked through hydroxymethyl R to cyanogen bromide activated Sepharose, whereby immobilised steroid is obtained. Other chemistries for conjugation are well known. See for example Maggio, "Enzyme-Immunoassay" (CRC, 1988, pp 71-135) and references cited therein.

The 8-azapurines of this invention are labelled with any conventional detectable label, e.g. a fluorescent moiety such a fluorescein, radioisotopes such as $^{14}C$ or $^3H$, stable free radicals, avidin, biotin and the like all of which previously have been used as labels for immunoassays or diagnostic probes. The label will be present on the oligonucleotide or on the residue of an analogue of this invention. Suitable labelling methods are well known and are readily used with reactive groups such as hydroxyl, allyl and the like. A simple method is to label the compound of this invention with $^3H$ by proton exchange. The compounds also are biotinylated using conventional methods. See for instance U.S. Pat. No. 5,276,143 for analogous structures. However, the compounds of this invention also are useful directly in diagnostic probe assays without an exogenous detectable label. In one embodiment of this alternative, antibodies are raised against the compounds of this invention. Such antibodies (which in turn are labelled or used in a double antibody configuration) bind to the analogue of this invention and thereby are useful in detecting its presence as label for a protein or oligonucleotide.

The compounds of the invention are useful for treatment of microbial infections, for treatment of tumours or for other indications described below. Microbial infections treatable by the compounds of this invention include viruses, parasites, yeast and fungi, but it is believed that the compounds are most effective against viruses, which constitutes the preferred utility. Exemplary viral infections include infections caused by DNA or RNA viruses including herpesviruses (herpes simplex virus type 1 (HSV-1), HSV-2, varicella zoster virus (VZV), Epstein-Barr virus (EBV), cytomegalovirus (CMV), human herpesvirus type 6 (HHV-6), HHV-7, HHV-8, bovine herpesvirus type 1, equine herpesvirus type 1), papillomaviruses (HPV types 1-55, including carcinogenic HPV), flaviviruses (including yellow fever virus, African swine fever virus and Japanese encephalitis virus), togaviruses (including Venezuelan equine encephalomyelitis virus), influenza viruses (types A-C), retroviruses (HIV-1, HIV-2, HTLV-I, HTLV-II, SIV, FeLV, FIV, MoMSV), adenoviruses (types 1-8), poxviruses (vaccinia virus), enteroviruses (poliovirus types 1-3, Coxsackie, hepatitis A virus, and ECHO virus), gastroenteritis viruses (Norwalk viruses, rotaviruses), hantaviruses (Hantaan virus), polyomavirus, papovaviruses, rhinoviruses, parainfluenza virus types 1-4, rabies virus, respiratory synctial virus (RSV), hepatitis viruses A, B, C and E, and the like.

The antiviral activity of individual compounds is determined by routine assay of antiviral (or other antimicrobial) activity using enzyme inhibition assays, tissue culture assays, animal model assays and the like as will be understood by those skilled in the art.

Protozoan parasite infections are treated using the compounds of the invention. The term protozoa include those members of the subphyla Sarcomastigophora and Sporozoa of the phylum Protozoa. More particularly, the term protozoa as used herein include genera of parasitic protozoa, which are important to man, because they either cause disease in man or in his domestic animals. These genera for the most part are classified in the superclass Mastigophora of the subphylum Sarcomastigophora and the class Telesporea of the subphylum Sporozoa in the classification according to Baker (1969). Illustrative genera of these parasitic protozoa include *Histomonas, Pneumocystis, Trypanosoma, Giardia, Trichomonas, Eimeria, Isopora, Leishmania, Entamoeba, Toxoplasma* and *Plasmodium*. Parasitic protozoans include *Plasmodium falciparum, Plasmodium berghei, Plasmodium malariae, Plasmodium vivax, Leishmania braziliensis, Leishmania donovani, Trypanosoma cruzi, Trypanosoma brucei, Trypanosoma rhodesiense, Pneumocystis carinii, Entamoeba histolytica, Trichomonas vaginalis* and the like (de Vries, E. et al., "*Mol. Biochem. Parasitol.*" 1991; 47:43-50) and trypanosomes (Kaminsky et al. "*J. Parasitol.*" 1994; 80(6): 1026-1030). The compounds in which R is $CH_2OH$ and B is 3-deazaadenine are particularly interesting in the treatment of malarial parasites.

Compounds of the invention are used to treat yeast or fungal infections caused by *Candida glabrata, Candida tropicalis, Candida albicans*, and other *Candida* species, *Cryptococcus* species including *Cryptococcus neoformans, Blastomyces* species including *Blastomyces dermatitidis,* *Torulopsis* species including *Torulopsis glabrata, Coccidioides* species including *Coccidioides immitis, Aspergillus* species and the like.

The compounds of the invention can also be (1) applied to tissue culture systems to eliminate or reduce viral spread or growth during the production of biopharmaceutical or other products (such as proteins or vaccines), (2) used to eliminate or reduce viral spread or growth in clinical sample (such as blood), and (3) used to stop growth of tissue culture cells while leaving the cells to carry on with protein production.

The compounds herein have been found to suppress immunostimulation. Accordingly, they can suppress metabolic activities of T-lymphocytes stimulated by diverse agents, e.g. concanavalin A, they principally will find application in the treatment of autoimmune diseases, e.g. arthritis, or in suppression of transplant rejection. Their therapeutically active concentrations are in the range of 1 mg/kg to 50 mg/kg of body weight.

Assays

Another aspect of the invention relates to the use of a compound as defined hereinabove in an assay for identifying further candidate compounds that influence the activity of one or more CDK enzymes.

Preferably, the assay is capable of identifying candidate compounds that are capable of inhibiting one or more CDK enzymes.

More preferably, the assay is a competitive binding assay.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of formula 1 with a CDK enzyme in the presence of a known substrate of said CDK enzyme and detecting any change in the interaction between said CDK enzyme and said known substrate.

A sixth aspect of the invention provides a method of detecting the binding of a ligand to a CDK enzyme, said method comprising the steps of:
(i) contacting a ligand with a CDK enzyme in the presence of a known substrate of said CDK enzyme;
(ii) detecting any change in the interaction between said CDK enzyme and said known substrate;
and wherein said ligand is a compound of formula 1.

One aspect of the invention relates to a process comprising the steps of:

(a) performing an assay method described hereinabove;

(b) identifying one or more ligands capable of binding to a ligand binding domain; and (c) preparing a quantity of said one or more ligands.

Another aspect of the invention provides a process comprising the steps of:

(a) performing an assay method described hereinabove;

(b) identifying one or more ligands capable of binding to a ligand binding domain; and (c) preparing a pharmaceutical composition comprising said one or more ligands.

Another aspect of the invention provides a process comprising the steps of:

(a) performing an assay method described hereinabove;

(b) identifying one or more ligands capable of binding to a ligand binding domain;

(c) modifying said one or more ligands capable of binding to a ligand binding domain;

(d) performing the assay method described hereinabove;

(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of proliferative disorders.

The above methods may be used to screen for a ligand useful as an inhibitor of one or more CDK enzymes.

Processes for Preparation

Substituted 8-azapurines of the formula (I) can be conveniently prepared by various methods well known from analogous reactions (e.g. "Advances in Heterocyclic Chemistry" 29, (1986). It is, for example, possible to provide a precursor of the ring system, which can be ring-closed either on the pyrimidine side or the triazole side to complete the structure by known methods. According to the invention there is further provided a process for the preparation of compound of formula (I),

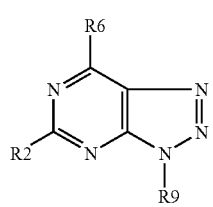

(I)

wherein $R_2$, $R_6$ and $R_9$ have above mentioned meanings, wherein a) a compound of formula (Ia),

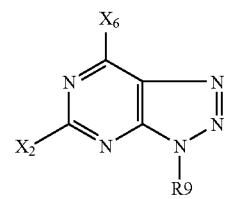

(Ia)

wherein $R_9$ is as defined in the formula (I), $X_2$ and $X_6$ are leaving groups, or $X_2$ is a leaving group and $X_6$ is $R_6$ or $X_2$ is $R_2$ and $X_6$ is a leaving group, wherein $R_2$ and $R_6$ have above mentioned meanings, is converted into a compound of the formula I, or b) a compound of the formula I, wherein substituents $R_2$, $R_6$ and $R_9$ have above mentioned meanings, is converted to further compound I by interconverting functional groups using known methods, or c) a compound II,

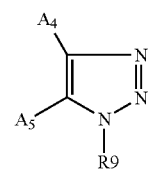

(II)

wherein $A_4$ is a reactive functional acid derivate and $A_5$ is an amino group reacting with a one-carbon reagent suitable for complexing the pyrimidine group, or d) a compound III

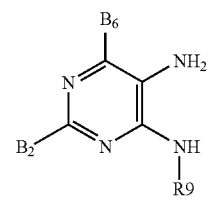

(III)

wherein $B_2$ and $B_6$ are $R_2$ and $R_6$, which have above mentioned meanings or $B_2$ and $B_6$ are leaving groups, is reacted with a nitrogen donor or reagent system, which is capable of complexing the triazole system by interaction with 4,5-diamino-substitutions, or e) a compound IV,

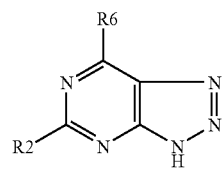

(IV)

wherein $R_2$ and $R_6$ have above mentioned meanings, is reacted with $R_9X_7$(V), wherein $X_7$ is a leaving group.

In process a) X substituents may, be for example a halogen. Halogen atoms are optionally, either progressively or simultaneously, subjected to a nucleophilic substitution in order to replace them by $R_2$ and $R_6$ substituent, that have above mentioned meanings.

In process b), for example the compounds of the formula I wherein R2 or R6 is mercapto may be prepared by treatment of compounds of the formula I wherein R2 or R6 is hydroxy with phosphorous pentasulfide, or for compounds of formula I where R2 or R6 is alkylthio may be prepared by treatment of compounds of formula I wherein R2 or R6 is mercapto with appropriate alkyl halogenide, or for compounds I wherein R2 or R6 is amino may be prepared by treatment of compounds of formula I where $R_2$ or $R_6$ is alkylthio with ammonia.

In process e) a compound of the formula I may be obtained either directly from compound of the formula IV or from the chloromercuri derivate of compound of the formula IV by reaction with $R_9X_7$ (V), where $X_7$ is a reactive functional acid derivate, such as for example halogenide or ester.

Compounds of the formula Ia can be prepared from a compound of the formula Ib,

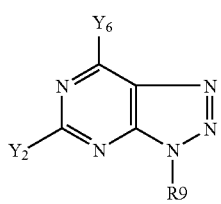

(Ib)

wherein $R_9$ is as defined in the formula I, $Y_2$ and $Y_6$ are hydroxy groups, or $Y_2$ is $R_2$ and $Y_6$ is a hydroxy group, or $Y_2$ is a hydroxy group and $Y_6$ is $R_6$, $R_2$ and $R_6$ have above mentioned meanings, for example by chlorination using chloride of phosphoric acid in the presence of an organic base (e.g. lutidine) or by thionylchloride, catalysed by dimethylformamide.

Compounds of the formula Ib can be prepared by condensation of a compound of formula the II, wherein $A_4$, for example carbamido or cyano group, and $A_5$ is an amino group with urea, ethyl carbonate and so on, for preparation or compound Ib, wherein $Y_2$ and $Y_6$ are hydroxy groups, or $Y_2$ is a hydroxy group and $Y_6$ is a amino group, or with quanidine for the preparation of a compound Ib, wherein $Y_2$ and $Y_6$ are amino groups, or for example with thiourea for the preparation of a compound Ib, wherein $Y_2$ is thio group and $Y_6$ is a hydroxy group.

Compound of the formula Ib, wherein $Y_2$ and $Y_6$ are amino groups, can be prepared by reacting a compound of the formula II, wherein $A_4$ and $A_5$ are both carbamido groups, by reacting with an inorganic bromate (e.g. kalium bromate).

Compound of the formula Ib, wherein $Y_2$ is alkyl, aryl, or substituted alkyl or aryl, can be prepared by condensation of compound of formula II with $R_2X_8$ (VI), where $X_8$ is a reactive functional acid derivate, such as for example ester or chloride, and R2 has above mentioned meanings.

Compounds of the formula Ib can be prepared by cyclisation a compound III, wherein $A_9$ is a $R_9$ as defined above, $B_2$ and $B_6$ are $R_2$ and $R_6$, preferentially selected from the group hydroxy, halogeno, or amino groups, by nitrous acid, for example an inorganic nitrite (e.g. sodium nitrite) in aqueous, acidic medium, or in organic solvent using alkylnitrite (e.g. amylnitrite).

Compounds of the formula IV can be prepared for example by cyclisation of compound of the formula III, or from a compound of the formula II wherein $R_9$ is hydrogen, by the methods described herein.

If necessary, some of the above reactions can be carried out with the reactive substituents, appropriately protected with blocking groups, which can be removed later.

The use of protecting groups is fully described for example in "Protective Groups in Organic Synthesis", 2nd edition, T. W. Greene and P. G. M. Wutz, Wiley-Interscience (1991).

The invention also relates to pharmaceutically acceptable salts of compounds of the formula I.

PMP and PME nucleotides are prepared by methods known for example from WO 94/03467, WO95/07920 and WO 96/33200. In general, the 6-chloro-8-azapurine is first alkylated in DMF either in the presence of an equivalent amount of sodium hydride or cesium carbonate at 60-100° C. The products are then isolated by chromatography on silica gel and crystallised from ethyl acetate by slow addition of petroleum ether until crystallisation occurs (the 2-amino-6-chloropurinyl PME/PMP compounds are crystalline, but the 6-chloropurinyl PME/PMP compounds are oils). The obtained 6-chloro compound is treated in ethanol solution with an excess (5 to 10 times) of the corresponding amine under reflux. The reaction is followed by TLC or HPLC analysis. The mixture is then evaporated, deionized on a cation exchanger column (Dowex 50), washed with 20% aqueous methanol, and the compound freed by the use of 2.5% ammonia in 20% aqueous methanol. The eluate is evaporated and dried over phosphorus pentoxide, the residue treated with 10% (v/v) bromotrimethylsilane in acetonitrile (5 ml per mM of compound) in order to deprotect the hydroxyl groups. The mixture is allowed to stand overnight and worked up by usual way. PMP/PME nucleotides can be easily brominated at R8 an subsequently modified at this position as described above for trisubstituted purines.

In an alternative method for making compounds of this invention, 2,6-dichloro-8-azapurine is treated for 3-12 h with excess (5-10 fold) of primary or secondary amine in absolute ethanol or methanol at reflux temperature or in an autoclave at 100-120° C. The residue is purified by crystallisation, deionization on a cation exchange resin or by silica gel chromatography. The obtained 6-substituted purine derivative is pretreated in dimethylformamide solution with one-half molar equivalent of cesium carbonate, one molar equivalent sodium hydride for 1 h at 100° C. and the appropriate phosphoro-organic synthon used for example for the preparation of PME-, (R)-PMP or (S)-PMP derivatives (1.1-1.5 molar equivalents is added to the mixture). The mixture is heated at 100-120° C. for 8-16 h, stripped off the solvent and the diester intermediate isolated by silica gel chromatography. The further treatment with bromotrimethylsilane and purification is performed as above. It is not essential to employ the phosphonyl-protecting group where it is expected that the R6-substituent may be labile to the TMS deprotection. In this case, the free acid is used as the starting material for addition of the amine.

Pharmaceutical Compositions

Another aspect relates to a pharmaceutical composition comprising a compound of the invention as defined above admixed with one or more pharmaceutically acceptable diluents, excipients or carriers. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2$^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention. Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 150 mg/day will be administered to the patient.

Combinations

In a particularly preferred embodiment, the one or more compounds of the invention are administered in combination with one or more other therapeutically active agents, for example, existing drugs available on the market. In such cases, the compounds of the invention may be administered consecutively, simultaneously or sequentially with the one or more other active agents.

By way of example, it is known that anticancer drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance in early tumor cells which would have been otherwise responsive to initial chemotherapy with a single agent. An example of the use of biochemical interactions in selecting drug combinations is demonstrated by the administration of leucovorin to increase the binding of an active intracellular metabolite of 5-fluorouracil to its target, thymidylate synthase, thus increasing its cytotoxic effects.

Numerous combinations are used in current treatments of cancer and leukemia. A more extensive review of medical practices may be found in "Oncologic Therapies" edited by E. E. Vokes and H. M. Golomb, published by Springer.

Beneficial combinations may be suggested by studying the growth inhibitory activity of the test compounds with agents known or suspected of being valuable in the treatment of a particular cancer initially or cell lines derived from that cancer. This procedure can also be used to determine the order of administration of the agents, i.e. before, simultaneously, or after delivery. Such scheduling may be a feature of all the cycle acting agents identified herein.

Therapeutic Administration

Suitable routes for administration include oral, rectal, topical (including dermal, ocular, buccal and sublingual), vaginal and parenteral (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

The therapeutical composition comprise about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present invention are prepared in a manner known per se, for example by means of convectional mixing, granulating, coating, dissolving or lyophilising processes.

Preferably, solutions of the active ingredient, and in addition also suspensions or dispersions, especially isotonic aqueous solutions, dispersions or suspensions, are used, it being possible for these to be prepared before use, for example in the case of lyophilised compositions which comprise the active substance by itself or together with a carrier, for example mannitol. The pharmaceutical compositions can be sterilised and/or comprise excipients, for example preservatives, stabilisers, wetting agents and/or emulsifiers, solubilizing agents, salts for regulating the osmotic pressure and/or buffers, and they are prepared in a manner known per se, for example by means of convectional dissolving or lyophilising processes. The solutions or suspensions mentioned can comprise viscosity-increasing substances, such as sodium carboxymethylcellulose, carboxymethylcellulose, dextran, polyvinylpyrrolidone or gelatin.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, acid, arachidonic acid, behenic acid or corresponding unsaturated acids, for example oleic acid, elaidic acid, euric acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris) and/or "Miglyol 812" (triglyceride of saturated fatty acids of chain length $C_8$ to $C_{12}$ from Hüls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients. Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidine, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterisation of different doses of active ingredient.

Pharmaceutical compositions, which can be used orally, are also hard capsules of gelatin and soft, closed capsules of gelatin and a plasticiser, such as glycerol or sorbitol. The hard capsules can contain the active ingredient in the form of granules, mixed for example with fillers, such as maize starch, binders and/or lubricants, such as talc or magnesium stearate, and stabilisers if appropriate. In soft capsules, the active ingredient is preferably dissolved or suspended in suitable liquid excipients, such as greasy oils, paraffin oil or liquid polyethylene glycols or fatty acid esters of ethylene glycol or propylene glycol, it being likewise possible to add stabilisers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parental administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate stabilisers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also contain emulsifiers and/or additives mentioned in connection with the ointments which increase uptake of water.

Creams are oil-in-water emulsions, which comprise more than 50% of water. Oily bases used are, in particular, fatty alcohols, for example lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding non-ionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example titanium oxide or zinc oxide, and furthermore talc and/or aluminium silicates, which have the task of binding the moisture or secretions present.

Foams are administered from pressurised containers and they are liquid oil-in-water emulsions present in aerosol foam. As the propellant gases, halogenated hydrocarbons, such as polyhalogenated alkanes, for example dichlorofluoromethane and dichlorotetrafluoroethane, or, preferably, non-halogenated gaseous hydrocarbons, air, $N_2O$, or carbon dioxide are used. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with the ethanol, and, if necessary, other excipients and additives, are admixed.

The present invention further provides veterinary compositions comprising at least one active ingredient as above defined together with a veterinary carrier therefor. Veterinary carriers are materials for administering the composition and may be solid, liquid or gaseous materials, which are inert or acceptable in the veterinary art and are compatible with the active ingredient. These veterinary compositions may be administered orally, parenterally or by any other desired route.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

Figure 2:
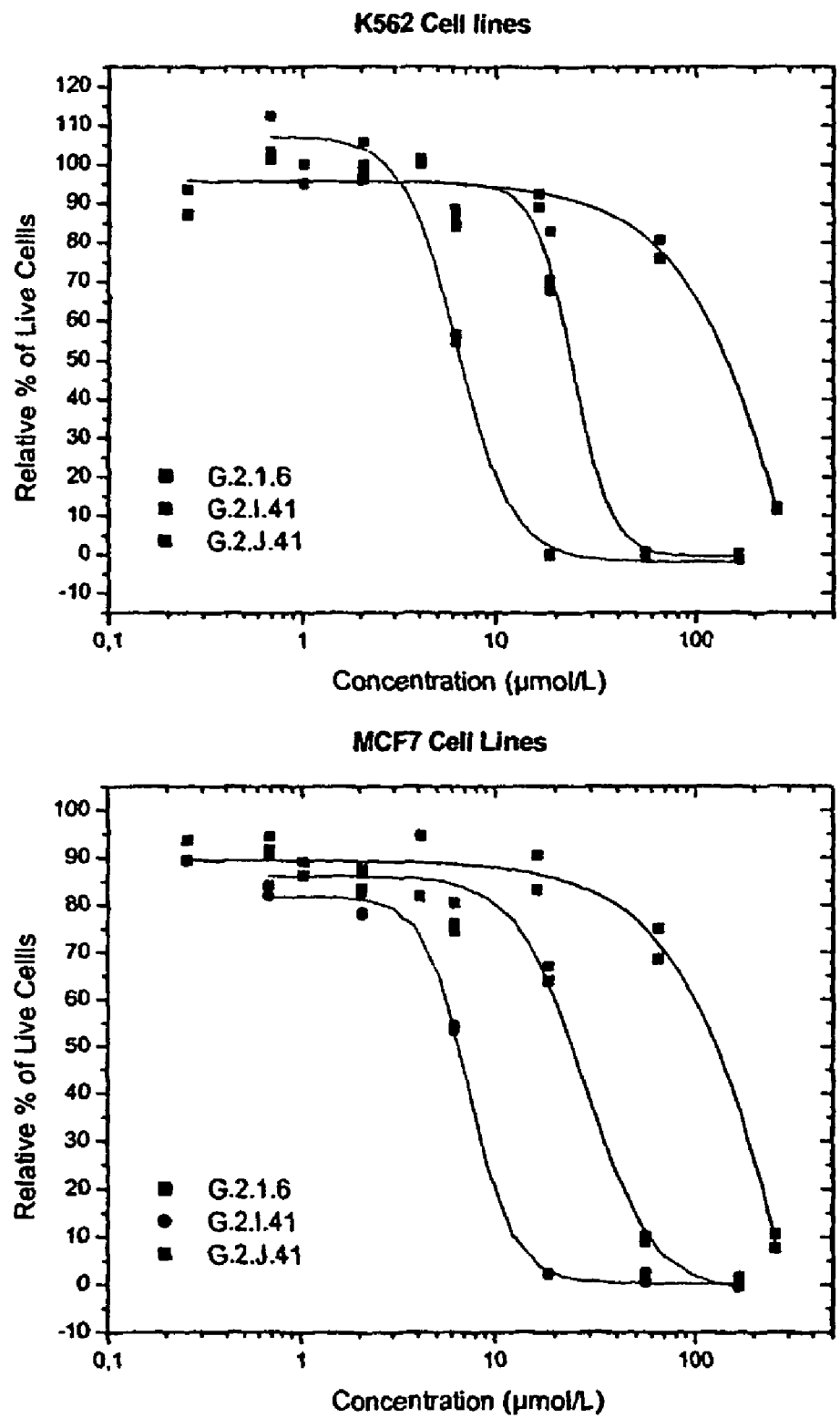
FIG. 2 shows the inhibition of growth of K562 (A) and MCF7 (B) tumour cell lines by different 8-azapurines. Cytotoxicity was determined in the presence of MTT. Activity is presented as percentage of maximum activity (in the absence of inhibitors).

The invention is further described by way of the following non-limiting examples, and with reference to FIGS. 1 and 2 wherein:

FIG. 1 shows the inhibition of p34$^{cdc2}$/cyclin B by several new 8-azapurines. Enzyme activity was assayed in the presence of increasing concentrations of inhibitors. Activity is presented as percentage of maximal activity, i.e. measured in the absence of inhibitors.

G.2.3.9: 2-R-(1-hydroxymethyl)propylamino-6-(3-hydroxybenzyl)amino-9-isopropyl-8-azapurine;

G.2.3.36: 2-(1-hydroxymethyl-2-methyl)propylamino6-(3-hydroxybenzyl)amino-9-isopropyl-8-azapurine;

G.2.I.41: 2-(4-aminocyclohexyl)amino-6-(3-chlorophenyl)amino-9-isopropyl-8-azapurine;

G.2.J.41: 2-(4-aminocyclohexyl)amino-6-(2-hydroxybenzyl)amino-9-isopropyl-8-azapurine.

FIG. 2 shows the inhibition of growth of K562 (A) and MCF7 (B) tumour cell lines by different 8-azapurines. Cytotoxicity was determined in the presence of MTT. Activity is presented as percentage of maximum activity (in the absence of inhibitors). G.2.1.6: 2-(3-hydroxypropylamino)-6-benzylamino-9-isopropyl-8-azapurine;

G.2.I.41: 2-(4-aminocyclohexyl)amino-6-(3-chlorophenyl)amino-9-isopropyl-8-azapurine;

G.2.J.41: 2-(4-aminocyclohexyl)amino-6-(2-hydroxybenzyl)amino-9-isopropyl-8-azapurine.

EXAMPLES $^1$H NMR spectra (δ, ppm, Hz) were measured on Varian Unity 300 instrument (300 Hz, CDCl$_3$), MS was measured on Waters/Micromass ZMD (direct inlet, ES$^+$, ES$^-$).

Thin layer chromatography was performed with TLC silica gel plates (Aldrich) and column chromatography with silica gel 60 (Merck).

The following chromatografic systems were used:
I) ethyl acetate:methanol:ammonia
II) chloroform
III) chloroform:methanol:ammonia
IV) chloroform:methanol
V) toluene:chloroform Example 1

4-Amino-5-carboxyamido-1-isopropyl-1,2,3-triazole

To a solution of absolute ethanol (10 ml) and sodium (10 mmol), isopropylazide (10 mmol) and 2-cyanoacetamide (10 mmol) was added. The mixture was heated during one hour to 90° C. and kept at this temperature for 4 hours. The reaction mixture was concentrated in vacuo and the residue diluted with water (1 ml). The product was obtained by extraction with ethyl acetate, evaporation of organic layer and crystallisation from water.

Yield=38.7%; m.p. 193-7° C.; TLC (I—12:3:1), $R_F$=0.6.

Example 2

2,6-Dihydroxy-9-isopropyl-8-azapurine

To a solution of sodium ethoxide, obtained from sodium (5 mmol) in absolute ethanol (13 ml) warmed to 90° C., 4-amino-5-carboxyamido-1-isopropyl-1,2,3-triazole (2.4 mmol), prepared as described in Example 1, and then diethyl carbonate (0.95 ml) during 40 minutes were added. The reaction mixture was heated at 90° C. for 4 hours. After cooling, the volatile components were evaporated in vacuo and water (2.5 ml) and acetic acid (1.4 ml) were added to the residue. The reaction mixture was concentrated in vacuo and purified by ionex (Dowex H$^+$, H$_2$O as eluant). The water phase was again evaporated in vacuo and the product was purified by chromatography (SiO$_2$, I—from 12:3:1 to 12:6:1)

Yield=30.5%; m.p. 303-6° C.; TLC (I—12:3:1) $R_F$=0.21 .

Example 3

2,6-Dichloro-9-isopropyl-8-azapurine

The mixture of 2,6-dihydroxy-9-isopropyl-8-azapurine (0.24 mmol), prepared as described in Example 2, phosphoryl chloride (0.6 ml) and lutidine (0.25 ml) was heated during 150 minutes to 120° C. and then at this temperature kept for 3 hours. After concentration in vacuo (bath temperature up to 80° C.) the residue was cooling and poured into ice-$H_2O$. The reaction mixture was extracted with benzene, the benzene solution was neutralized and dried and then evaporated to give the crude dichloro derivate.

Yield of crude product=87%; TLC (I—12:3:1), $R_F$=0.36

Example 4

2-Chloro-6-benzylamino-9-isopropyl-8-azapurine

The crude 2,6-dichloro-9-isopropyl-8-azapurine (ca 0.086 mmol), prepared as described in Example 3, was suspended in n-butanol (0.8 ml) and heated to dissolve. After cooling the solution, 6-benzylamine (0.36 mmol) was added. The product started to precipitate after a few minutes later. The reaction mixture was stirred overnight. The precipitate was separated and washed with cold n-butanol.

Yield=82.7%; m.p. 184-5° C.; TLC (II) $R_F$=0.16.

Example 5

2-Chloro-6-(3-hydroxybenzylamino)-9-isopropyl-8-azapurine

The compound was prepared according to the method of Example 4 using 3-hydroxybenzylamine. After separation of solid the mother liquid was purified by chromatography ($SiO_2$, IV—9:1 as eluant).

Yield=86%; m.p. 188-191° C.; TLC (IV—9:1) $R_F$=0.72

Example 6

2-Chloro-6-(3-chloroanilino)-9-isopropyl-8-azapurine

The compound was prepared according to the method of Example 4 using 3-chloroaniline. The reaction mixture was stirred for three days. The purification of the mother liquid was made by chromatography ($SiO_2$, V—7:3 as eluant).

Yield=83.4%; TLC (II) $R_F$=0.36 (IV—99:1)$R_F$=0.54
M.S: 323.0 (100%, M+H$^+$), 325.0 (63%, M+H$^+$)

Example 7

2-Chloro-6-(2-hydroxybenzylamino)-9-isopropyl-8-azapurine

The compound was prepared according to the method of Example 6 using 2-hydroxybenzylamine. The purification of mother liquid was realised by chromatography ($SiO_2$, IV—95:5 as eluant).

Yield=95.4%; TLC (II) $R_F$=0.33 (IV)$R_F$=0.66

Further compounds prepared in accordance with the methods of Examples 4-7 are shown in Table 1.

Example 8

2-(3-Hydroxypropylamino)-6-benzylamino-9-isopropyl-8-azapurine

The mixture of 2-chloro derivate from Example 4 (0.066 mmol), n-butanol (0.3 ml) and 3-amino-1-propanol was heated at 100° C. for 90 minutes. The reaction mixture was evaporated to dryness in vacuo and then purified by chromatography ($SiO_2$, III—99:10:0.1 as eluant).

Yield=85.2%; m.p.=123-5° C.; TLC (III—99:10:0.1) $R_F$=0.15

$^1$H NMR: 1.65 d (6H, J=7.0 Hz, $(CH_3)_2$CH), 1.80 m (2H, $CH_2\underline{CH_2}CH_2$), 3.65 m (3.65 m (2H, $\overline{CH_2}CH_2CH_2$), 4.76 bs (2H, $\overline{CH_2}$Ph), 4.88 sept (1H, J=6.6 Hz, $\overline{C\underline{H}}(CH_3)_2$) 5.27 bs (1H, N$\overline{H}$), 6.30 bs (1H, NH), 7.30-7.40 m (5H, Ph).

Example 9

2-(1-Hydroxymethyl-2-methylpropylamino)-6-(3-hydroxybenzylamino)-9-isopropyl-8-azapurine The compound was prepared from 2-chloro derivate of Example 5 and the appropriate amine according to the method of Example 8. The reaction mixture was heated at 90° C. for 21 hours. After purification by chromatography ($SiO_2$, IV—97:3 as eluent) the final product was purified again by chromatography ($SiO_2$, ethylacetate as eluent).

Yield=67.9%; m.p.=150-2° C.; TLC (IV—97:3) $R_F$=0.45
MS: 386.3 (100% M+H$^+$)

$^1$H NMR: 0.99 d (3H, J=6.8 Hz, $(CH_3)_2$CHC*), 1.01 d (3H, J=6.8 Hz, $(CH_3)_2$CHC*), 1.63 d (3H, J=7.0 Hz, $(CH_3)_2$CHN), 1.64 d (3H, J=7.0 Hz, $(CH_3)_2$CHN), 1.96 m (1H, CH* $\underline{CH}(CH_3)_2$)), 3.70 m (1H, $\underline{CHH}$OH), 3.81-3.90 m (2H, CH H$\overline{OH}$+$\underline{CH}$*NH), 4.70 bs (2H, $CH_2$Ph), 4.89 sept (1H, J=6.6 Hz, $C\underline{H}(CH_3)_2$), 9.73-6.95 m (3H, Ph), 7.18 dd (1H, J=7.8 Hz, Ph).

Example 10

2-(1-Hydroxymethyl-2-methylpropylamino)-6-(3-chloroanilino)-9-isopropyl-8-azapurine The compound was prepared according to the method of Example 9 with 2-chloro derivate of Example 6. The reaction mixture was heated at 95° C. for 28 hours. The crude product was purified by chromatography ($SiO_2$, IV—98.5:1.5 as eluant).

Yield=56.5%; m.p.=160-3° C.; TLC (IV—99:1) $R_F$=0.15
MS: 390.2 (100% M+H$^+$), 392.2 (35%, M+H$^+$)

$^1$H NMR: 1.03 d (3H, J=7.0 Hz, $(CH_3)_2$CHC*), 1.05 d (3H, J=7.0 Hz, $(CH_3)_2$CHC*) 1.64 d (6H, J=6.7 Hz, $(CH_3)_2$CHN), 1.78 bs (1H, OH), 2.01 m (1H, J=7.0 Hz, C*HC$\underline{H}(CH_3)_2$), 3.68-4.02 m (3H, $CH_2$OH+C$\underline{H}$*), 4.87 sept (1H, J=6.7 Hz, $(CH_3)_2$C$\underline{H}$N), 5.30 bs (1H, NH), 7.09 d (1H, J=7.7 Hz, Ph), 7.23-7.25 m (1H, Ph), 7.48 m (1H, Ph), 8.00 bs (1H, NH), 8.29 bs (1H, Ph).

Example 11

2-(trans-4-Aminocyklohexylamino)-6-(3-chloroanilino)-9-isopropyl-8-azapurine The compound was prepared according to the method of Example 10 with 2-chloro derivate of Example 6. Reaction mixture was heated at 95° C. for 2 hours and at 115° C. for 4 hours. The crude product (after evaporation also 1,4-diaminocyclohexane in high vacuo) was purified by chromatography (SiO$_2$, III—85:15:0.5 as eluant).

Yield=89.7%; m.p. 221-3° C.; TLC (III, 85:15:0.5) R$_F$=0.29 (IV —80:20) R$_F$=0.50

MS: 401.3 (100% M+H$^+$), 403.3 (33% M+H$^+$)

$^1$H NMR: 1.20-1.36 m (4H, cyclohexyl), 1.66 d (6H, J=6.7 Hz, (CH$_3$)$_2$CH), 1.93 m (2H, cyclohexyl), 2.20 m (2H, cyclohexyl), 2.72 m (1H, cyclohexyl), 3.85 m (1H, cyclohexyl), 4.93 sept (1H, J=6.7 Hz, (CH$_3$)$_2$CH), 5.08 d (1H, NH), 7.09 d (1H, J=7.6 Hz, Ph) 7.23-7.31 (1H, Ph), 7.44 m (1H, Ph), 7.65 bs (1H, NH), 8.05 bs (1H, Ph).

Example 12

2-(trans-4-Aminocyclohexylamino)-6-(2-hydroxybenzylamino)-9-isopropyl-8-azapurine The title product was prepared according to the method of Example 11 with 2-chloro derivative of Example 7.

Yield=84.8%; m.p.=120-3° C.; TLC (III—85:15:0.5) R$_F$=0.26 (IV—80:20) R$_F$=0.47

MS: 397.2 (100% M+H$^+$)

Example 13

2-[1(R)-Hydroxymethylpropylamino]-6-benzylamino-9-isopropyl-8-azapurine

The title compound was prepared according to the method of Example 10 with 2-chloro derivative of Example 4.

Yield=54%; m.p.=115-18° C.; TLC (IV—95.5:1.5), R$_F$=0.25; MS: 372.3 (100% M+H$^+$)

$^1$H NMR: 1.02 t (3H, J=7.4 Hz, CH$_3$CH$_2$), 1.56 m (2H, CH$_2$CH$_3$), 1.64 d (6H, J=6.9 Hz, (CH$_3$)$_2$CH), 3.64 m (1H, CHNH), 3.77-4.02 m (2H, AB, CH$_2$OH), 4.77 bs (2H, CH$_2$Ph), 4.89 sept (1H, J=6.9 Hz, CH(CH$_3$)$_2$), 5.14 bs (1H, NH), 6.54 bs (1H, NH), 7.25-7.38 m (5H, Ph).

Further compounds prepared in accordance with the methods of Examples 7-13 are shown in Table 2.

Example 14

2-Methyl-6-hydroxy-9-isopropyl-8-azapurine

To a solution of sodium ethoxide obtained from sodium (6 mmol) in absolute ethanol (5 ml), isopropylazide (3.2 mmol) and 2-cyanoacetamide (2.5 mmol) were added. The reaction mixture was slowly heated to 90° C. and then kept under reflux for 1 hour, then anhydrous ethyl acetate (5 mmol) was added and the refluxing continued for 9 hours. The reaction mixture was concentrated in vacuo and the residue was diluted with water (0.5 ml) and acetic acid (1 ml). The solution was concentrated in vacuo again, then water was added and reaction mixture extracted with chloroform. The chloroform layer was evaporated and the residue was crystallised from methanol.

Yield=31.6%
m.p. 205-13° C.

Example 15

2-Methyl-6-chloro-9-isopropyl-8-azapurine and 2-methyl-6-benzylamino-9-isopropyl-8-azapurine Thionylchloride (2 mmol), N,N-dimethylformamide (0.6 mmol) and 2-methyl-6-hydroxy-9-isopropyl-8-azapurine, prepared as described in Example 14, suspended in chloroform (1.3 ml) were heated under reflux for 90 minutes (the mixture became clear nearly immediately). The volatile components were evaporated, the residue cooled and poured into ice-H$_2$O. Water was separated from the reaction mixture and residue was dried under vacuum. The crude product was obtained by extraction of the solid residue with benzene, evaporation of organic solvent and dilution with n-butanol (1.4 ml).

TLC (II) R$_F$=0.29

Benzylamine (0.84 mmol) was added to the solution of 6-chloro derivative in n-butanol. The reaction mixture was heated at 100° C. for 90 minutes and then partially concentrated in vacuo. After cooling, the precipitate was separated, washed with cold n-butanol and dried under vacuum. The residual liquid was evaporated and both—the precipitate and residue from mother liquid—were purified by chromatography (SiO$_2$, IV—99:1).

Yield=29%; m.p. 133-9° C.; TLC (IV—99:1) R$_F$=0.24

$^1$H NMR: 1.69 d (6H, J=6.6 Hz, (CH$_3$)$_2$CH), 2.63 s (3H, CH$_3$), 4.88 bs (2H, CH$_2$Ph), 5.12 sept (1H, J=6.6 Hz, CH(CH$_3$)$_2$), 7.30-7.43 m (5H, Ph).

MS: 283.1 (100% M+H$^+$)

Further compounds prepared in accordance with the methods of Examples 14 and 15 are shown in Table 3.

Example 16

4,5-Diamino-2,6-dichloropyrimidine a) 4-Amino-2,6-dichloro-5-nitropyrimidine

The mixture of 4-amino-2,6-dihydroxy-5-nitropyrimidine (17 mmol), phosphoryl chloride (21 ml) and lutidine (4.5 ml) was vigorously stirred and heated to 120° C. in 100 minutes. This temperature was kept for another 3 hours. After concentration in vacuo, the reaction residue was cooling (0° C.), ice-H$_2$O was added and the reaction mixture was extracted with diethyl ether. The etheric solution was dried, decolorized with activated carbon and then evaporated to give crude product (58.7%). This product was purified by crystallization from benzene.

Yield=41.7%; m.p.=161-2° C.; TLC (II) R$_F$=0.16; (III-95:15:1) R$_F$=0.69

MS: 206.9 (100%, M−H$^+$), 208.9 (66% M−H$^+$)

b) 4,5-Diamino-2,6-dichloropyrimidine

To a solution of 4-amino-2,6-dichloro-5-nitropyrimidine, prepared as described in a), in methanol (30 ml), was added Raney nickel freshly prepared from 500 mg of alloy. The reaction mixture was stirred 20 hours in the hydrogen atmosphere. Then a new catalyst, prepared from 500 mg of alloy, was added and the reaction mixture was stirred next 24 hours in the hydrogen atmosphere. The catalyst was removed, the reaction mixture was concentrated in vacuo and the residue was extracted with hot water. Product, which was obtained after cooling of the water solution, was purified by chromatography (SiO$_2$, VI—1:1)

Yield=47.9%; TLC (IV, 95:5) R$_F$=0.14; (V, 1:1) R$_F$=0.27

MS: 179.1 (100%, M+H$^+$), 181.2 (83%, M+H$^+$)

Example 17

2,6-Dichloro-8-azapurine 4,5-Diamino-1,6-dichloropyrimidine (0.55 mmmol), prepared as described in Example 16, was suspended in water (2 ml) and heated to dissolve. After cooling the solution in the ice-water bath, acetic acid (2 ml) was added to the solution. Sodium nitrite in water (0.5 mol/1-2 ml) was added to this stirred solution at 0° C. during 15 minutes. After next 20 minutes in the ice-water bath, the reaction mixture was extracted with diethyl ether. The etheric solution was neutralized and dried and then evaporated to give the crude product (100%). This product was purified by crystallization from absolute diethyl ether.

Yield=47%; m.p.>260° C.; TLC (I, 12:2:1) $R_F$=0.22
MS: 188.0 (100%, M–H$^+$), 190.0 (65%, M–H$^+$)

Example 18

2-Chloro-6-benzylamino-8-azapurine 2,6-Dichloro-8-azapurine (0.84 mmol), prepared as described in Example 17, was dissolved in n-butanol (4 ml) and benzylamine (1.4 mmol) was added. The reaction mixture was stirred at room temperature overnight. After concentration in vacuo the product was purified by chromatography (SiO$_2$, IV—from 1% MeOH and 0.25% acetic acid to 2% MeOH with 0.35% acetic acid).

Yield=63%; Mp 122-4° C.; MS: 259.2 (100%, M+H$^+$), 261.1 (31%, M+H$^+$)

Example 19

2-Chloro-6-(3-chloroanilino)-8-azapurine

The compound was prepared according to the method of Example 18 using 3-chloroaniline (4 equivalents).

The crude product was purified by chromatography (SiO$_2$, IV—8:2).

Yield=72%; TLC (IV—8:2) $R_F$=0.33; MS: 279.1 (100%, M+H$^+$), 281.0 (65%, M+H$^+$)

Example 20

2-(3-Aminopropylamino)-6-benzylamino-8-azapurine

The mixture of 2-chloro derivate (0.65 mmol) from Example 18, n-butanol (4 ml) and 1,3-diaminopropane (13 mmol) was heated at 120° C. for 4 hours. The reaction mixture was evaporated to dryness in vacuo and then purified by chromatography (SiO$_2$, III—from 20% MeOH and 5% NH$_4$OH to 25% MeOH and 5% NH$_4$OH). The final product was purified by crystallization from system chloroform/absolute diethyl ether.

Yield=88.8%; m.p. 119-24° C.; TLC (III—20:8:0.75) $R_F$=0.3

MS: 299.3 (100%, M+H$^+$), 300.3 (25%, M+H$^+$) $^1$H NMR (400 MHz, CD$_3$OD): 1.788 tt (2H, 6.6, 6.8, CH$_2$C$\underline{H}_2$CH$_2$), 2.755 t (2H, 6.9, C$\underline{H}_2$NH$_2$), 3.508 t (2H, 6.6, NHC$\underline{H}_2$), 5.582 s (2H, C$\underline{H}_2$Ph), 7.26-7.35 m (5H, Ph).

Example 21

2-(4-Hydroxycyklohexylamino)-6-(3-chloroanilino)-8-azapurine

The compound was prepared according to the method of Example 20 using 4-hydroxycyclohexylamine (only 5 equivalents). The crude product was purified by chromatography (SiO$_2$, III—95:15:1).

Yield=44%; m.p. 246-9° C.; TLC (VII—12:3:1) $R_F$=0.16
MS: 360 (100%, M+H$^+$), 362 (35%, M+H$^+$)

Further compounds prepared in accordance with the methods of Examples 14-21 are shown in Table 4.

Example 22

Preparation of Affinity Sorbent

Preparation of 2-(3-aminopropylamino)-3-(3-carboxy-4-chloroanilino)-9-isopropyl-8-azapurine Epoxy Activated Sepharose 6B Affinity Matrix Freeze-dried epoxy activated Sepharose 6B (Pharmacia LKB, Piscataway, N.J.) was chosen for the coupling reaction due to its ability to form an ether bond between a hydroxyl-containing ligand and the epoxide group on the Sepharose. The gel was swollen according to the manufacturer's instructions, (100 mg) of any one of the compound defined in claim 1 was dissolved in 1 ml coupling solution (1.2:1, v/v, DMF, 0.1N NaOH) and mixed with 0.5 ml of swollen gel at pH 10-11 for 72 h at room temperature with gentle agitation. Excess reactive groups were blocked with 1M ethanolamine for 4 hours at 50° C. and the gel slurry was poured into 1-ml syringe column. The resin was activated with three alternating cycles of twenty column volumes each of pH 4.0 (0.1M acetate, 0.5 M NaCl) and pH 8.0 (0.1M tris-HCl, 0.5 M NaCl) buffers followed by twenty column volumes of reaction buffer (20 mM HEPES, pH 7.3, 10 mM MgCl$_2$, 15 mM glycerophosphate, 0.5 mM sodium orthovanadate, 0.5 mM EGTA). The column was stored at 4° C. in the reaction buffer containing 0.1% sodium azide and regenerated prior to each use with alternating cycles of low and high pH as described above.

The Sf9 insect cell lysate (500 µg protein in 1-ml reaction buffer) was passed over the affinity column matrix sequentially five times and the flow through was saved (unbound material). The matrix was then washed three times with 1 ml reaction buffer (wash 1-3) then three times each reaction buffer containing 0.5M NaCl (eluate 1-3). The coupled proteins were eluted at low pH (pH 4.0, 0.1M acetate, 0.5M NaCl) as described above and aliquots (20 µl from 1 ml) of each sample were assayed for their ability to phosphorylate histone H1 and other substrate proteins as described in Example 17. The presence of CDK complexes was also determined by SDS-PAGE.

Table 5 shows the results of inhibitory activity of novel compounds against CDC2 and IκB-α in comparison with the data on the prototype compounds (trisubstituted purines olomoucine, roscovitine and purvalanol A). Most of the 2,6,9-trisubstituted 8-azapurine derivatives showed marked inhibitory activity in in vitro kinase assays.

Example 24

CDK Inhibitory Activity on Plant Kinases

Protein extraction and purification of pant CDK by binding to p13$^{suc1}$-beads or immunopurification with an antibody specific to the cdc2a-MS protein was carried out as described previously (Bögre et al. 1997, Plant Physiol. 113, 1997, 841-852). The MMK1 protein kinase was purified with a specific antibody from *Vicia faba* extracts as described by Bögre et al. 1997a, Plant Cell 9, 75-83). Protein kinase activity was measures as described above in Example 23. The quantification of radioactivity incorporated into histone H1 or myelin basic protein was undertaken using phosphoimager.

Example 23

CDK Inhibition Assays

Proteins

Cyclin-dependent kinases (p34$^{cdc2}$, p33$^{cdk2}$) and cyclins (cyclin B, E) are produced in Sf9 insect cells coinfected with appropriate baculoviral constructs. The cells are harvested 68-72 hrs post infection in lysis buffer for 30 min on ice and the soluble fraction is recovered by centrifugation at 14.000 g for 10 min. The protein extract is stored at −80° C.

Lysis buffer: 50 mM Tris pH 7.4, 150 mM NaCl, 5 mM EDTA, 20 mM NaF, 1% Tween, 1 mM DTT, 0.1 mM PMSF, leupeptine, aprotonine.

Enzyme Inhibition Assays

To carry out experiments on kinetics under linear conditions, the final point test system for kinase activity measurement is used. The kinase is added to reaction mixture in such a way as to obtain linear activity with respect to the concentration of enzyme and with respect to time.

The p34$^{cdc2}$ and p33$^{cdk2}$ kinase inhibition determination involves the use of 1 mg/ml histone H1 (Sigma, type III-S) in the presence of 15 µM [γ-$^{32}$P]ATP (500-100 cpm/pmol) (Amersham) in a final volume of 20 µl. Kinase activity is determined at 30° C. in the kinase buffer.

Tested compounds are usually dissolved to 100 mM solutions in DMSO, final concentration of DMSO in reaction mixture never exceeds 1%. The controls contain suitable dilutions of DMSO.

After 10 min, addition 3×SDS sample buffer stops the incubations. Phosphorylated proteins are separated electrophoretically using 12.5% SDS polyacrylamide gel. The measurement of kinase activity is done using digital image analysis.

The kinase activity is expressed as a percentage of maximum activity, the apparent inhibition constants are determined by graphic analysis (FIG. 1). IC50 was calculated from dose response curves showed on FIG. 1.

Kinase buffer: 50 mM Hepes pH 7.4, 10 mM MgCl$_2$, 5 mM EGTA, 10 mM 2-glycerolphosphate, 1 mM NaF, 1 mM DTT Table 6 shows the results of inhibitory activity of novel compounds against plant CDK and MPA kinases in comparison with the data on the prototype compounds (trisubstituted purines olomoucine, roscovitine and purvalanol A). Most of the 2,6,9-trisubstituted 8-azapurine derivatives showed marked inhibitory activity in in vitro plant kinase assays.

Example 25

Modulation of the Activity of β-Adrenergic Receptors

Rat C6 glioma (ATCC N° CCL107) was cultivated in monolayer in serum-free chemically defined medium containing Ham's F10/minimal essential medium (1:1 vol/vol), 2 mM L-glutamine, 1% (vol/vol) minimal essential medium vitamins (100×), 1% (vol/vol) minimal essential medium nonessential amino acids (100×), 100 U/ml penicillin, 100 µg/ml streptomycin and 30 nM sodium selenite. Incubation was at 37° C. in a humidified atmosphere. Assays were performed in the logarithmic growth phase at a density of 2.5× 10$^5$ cells/cm$^2$. Intracellular cAMP synthesis was induced by addition of 5 µM (−) isoproterenol. After 30 min incubation at 37° C. the medium was removed and the cellular amount of cAMP determined using the cAMP-enzyme immunoassay kit of Amersham. The I$_{50}$ is determined from a dose-response curve in duplicate (Table 7). The effect of seven 8-azapurine-analogs was measured after simultaneous addition with isoproterenol.

As P2Y$_1$-like and A2 purinergic receptors, negatively and positively coupled to adenylate cyclase respectively, are present on rat C6 glioma it has to be determined if the modulation of the synthesis of cAMP is due to inhibition of the activation of β-adrenergic receptors by isoproterenol are due to activation of purinergic receptors.

Example 26

In Vitro Cytotoxic Activity of Novel Compounds

One of the parameters used, as the basis for colorimetric assays is the metabolic activity of viable cells. For example, a microtiter assay, which uses the tetrazolium salt MTT, is now widely used to quantitate cell proliferation and cytotoxicity. For instance, this assay is used in drug screening programs and in chemosensitivity testing. Because only metabolically active cells cleave tetrazolium salts, these assays detect viable cells exclusively. In the case of MTT assay, yellow soluble tetrazolium salt is reduced to coloured water-insoluble formazan salt. After it is solubilized, the formazan formed can easily and rapidly be quantified in a conventional ELISA plate reader at 570 nm (maximum absorbance). The quantity of reduced formazan corresponds to number of vital cells in the culture.

Human T-lymphoblastic leukemia cell line CEM; promyelocytic HL-60 and monocytic U937 leukemias; breast carcinoma cell lines MCF-7, BT549, MDA-MB-231; glioblastoma U87MG cells; cervical carcinoma cells HELA; sarcoma cells U2OS and Saos2; hepatocellular carcinoma HepG2; mouse immortalized bone marrow macrophages B2.4 and B10A.4; P388D1 and L1210 leukemia; B16 and B16F10 melanomas were used for routine screening of compounds. The cells were maintained in Nunc/Corning 80 cm$^2$ plastic tissue culture flasks and cultured in cell culture medium (DMEM with 5 g/l glucose, 2 mM glutamine, 100 U/ml penicillin, 100 µg/ml streptomycin, 10% fetal calf serum and sodium bicarbonate).

The cell suspensions that were prepared and diluted according to the particular cell type and the expected target cell density (2.500-30.000 cells per well based on cell growth characteristics) were added by pipette (80 µl) into 96/well microtiter plates. Inoculates were allowed a pre-incubation period of 24 hours at 37° C. and 5% CO$_2$ for stabilisation. Four-fold dilutions of the intended test concentration were added at time zero in 20 µl aliquots to the microtiter plate wells. Usually, test compound was evaluated at six 4-fold dilutions. In routine testing, the highest well concentration was 266.7 µM, but it can be the matter of change dependent on the agent. All drug concentrations were examined in duplicates. Incubations of cells with the test compounds lasted for 72 hours at 37° C., in 5% CO$_2$ atmosphere and 100% humidity. At the end of incubation period, the cells were assayed by using the MTT. Ten microliters of the MTT stock solution were pipetted into each well and incubated further for 1-4 hours. After this incubation period, formazan was solubilized by addition of 100 µl/well of 10% SDS in water (pH=5.5) followed by further incubation at 37° C. overnight. The optical density (OD) was measured at 540 nm with the Labsystem iEMS Reader MF (UK). The tumour cell survival (TCS) was calculated using the following equation: TCS= (OD$_{drug\ exposed\ well}$/mean OD$_{control\ wells}$)×100%. The IC$_{50}$ value, the drug concentration lethal to 50% of the tumour cells, was calculated from the obtained dose response curves (FIG. 2).

Cytoxicity of novel compounds was tested on panel of cell lines of different histogenetic and species origin (Table 8). Higher activities were found in all tumour cell lines tested. Notably, the higher effectiveness of novel derivatives was also found in cell lines bearing various mutations or deletions in cell cycle associated proteins, e.g. HL-60, BT549, Hela, U2OS, MDA-MB231, and Saos2. It indicates that these substances should be equally effective in tumours with various alterations of tumour suppressor genes, namely p53, Rb, etc. Importantly, this observation distinguishes the novel compounds from flavopiridol and related compounds, as their biological activity is dependent on p53

Example 27

Immunosuppressive Activity

One of the most important parameters of specific cellular immunity is proliferative response of lymphocytes to antigens or polyclonal mitogens. The majority of normal mammalian peripheral lymphocytes comprise resting cells. Antigens or nonspecific polyclonal mitogens have the capacity to activate lymphoid cells and this is accompanied by dramatic changes of intracellular metabolism (mitochondrial activity, protein synthesis, nucleic acids synthesis, formation of blastic cells and cellular proliferation). Compounds with ability to selectively inhibit lymphocyte proliferation are potent immunosuppressants. Variety of in vitro assays was developed to measure proliferative response of lymphocytes. The most commonly used is $^3$H-thymidine incorporation method.

During cell proliferation, DNA has to be replicated before the cell is divided into two daughter cells. This close association between cell doublings and DNA synthesis is very attractive for assessing cell proliferation. If labeled DNA precursors are added to the cell culture, cells that are about to divide incorporate the labeled nucleotide into their DNA. Traditionally, those assays usually involve the use of radiolabeled nucleosides, particularly tritiated thymidine ([$^3$H]-TdR). The amount of [$^3$H]-TdR incorporated into the cellular DNA is quantified by liquid scintillation counting.

Human heparinized peripheral blood was obtained from healthy volunteers by cubital vein punction. The blood was diluted in PBS (1:3) and mononuclear cells were separated by centrifugation in Ficoll-Hypaque density gradient (Pharmacia, 1.077 g/ml) at 2200 rpm for 30 minutes. Following centrifugation, lymphocytes were washed in PBS and resuspended in cell culture medium (RMPI 1640, 2 mM glutamine, 100 U/ml penicillin, 100 μg/ml streptomycin, 10% fetal calf serum and sodium bicarbonate).

The cells were diluted at target density of 1.100.000 cells/ml were added by pipette (180 μl) into 96/well microtiter plates. Four-fold dilutions of the intended test concentration were added at time zero in 20 μl aliquots to the microtiter plate wells. Usually, test compound was evaluated at six 4-fold dilutions. In routine testing, the highest well concentration was 266.7 μM. All drug concentrations were examined in duplicates. All wells with exception of unstimulated controls were activated with 50 μl of concanavalin A (25 μg/ml). Incubations of cells with test compounds lasted for 72 hours at 37° C., in 5% $CO_2$ atmosphere and 100% humidity. At the end of incubation period, the cells were assayed by using the [$^3$H]-TdR:

Cell cultures were incubated with 0.5 μCi (20 μl of stock solution 500 μCi/ml) per well for 6 hours at 37° C. and 5% $CO_2$. The automated cell harvester was used to lyse cells in water and adsorb the DNA onto glass-fiber filters in the format of microtiter plate. The DNA incorporated [$^3$H]-TdR was retained on the filter while unincorporated material passes through. The filters were dried at room temperature overnight, sealed into a sample bag with 10-12 ml of scintillant. The amount of [$^3$H]-TdR present in each filter (in cpm) was determined by scintillation counting in a Betaplate liquid scintillation counter. The effective dose of immunosuppressant (ED) was calculated using the following equation: ED= ($CCPM_{drug\ exposed\ well}$/mean $CCPM_{control\ wells}$)×100%. The $ED_{50}$ value, the drug concentration inhibiting proliferation of 50% of lymphocytes, was calculated from the obtained dose response curves.

To evaluate immunosuppressive activity of substituted 8-azapurines, their ability to inhibit polyclonal mitogen induced proliferation of normal human lymphocytes was analyzed (Table 9). Our data demonstrate that these compounds have only marginal activity on $^3$H-thymidine incorporation, nonetheless, they efficiently inhibit proliferation of activated lymphocytes. Effective immunosuppressive dose of new derivatives under in vitro conditions was close to 1-20 μM.

Example 28

Dry Capsules 5000 capsules, each of which contain 0.25 g of one of the compounds of the formula I mentioned in the preceding or following Examples as active ingredient, are prepared as follows:

Composition

| Active ingredient | 1250 g |
| Talc | 180 g |
| Wheat starch | 120 g |
| Magnesium stearate | 80 g |
| Lactose | 20 g |

Preparation process: The powdered substances mentioned are pressed through a sieve of mesh width 0.6 mm. Portions of 0.33 g of the mixture are transferred to gelatine capsules with the aid of a capsule-filling machine.

Example 29

Soft Capsules 5000 soft gelatine capsules, each of which contain 0.05 g of one of the compounds of the formula I mentioned in the preceding or following Examples as active ingredient, are prepared as follows:

Composition

| Active ingredient | 250 g |
| Lauroglycol | 2 liters |

Preparation process: The powdered active ingredient is suspended in Lauroglykol® (propylene glycol laurate, Gattefossé S. A., Saint Priest, France) and ground in a wet-pulveriser to a particle size of about 1 to 3 μm. Portions of in each case 0.419 g of the mixture are then transferred to soft gelatine capsules by means of a capsule-filling machine.

Example 30

Soft Capsules 5000 soft gelatine capsules, each of which contain 0.05 g of one of the compounds of the formula I mentioned in the preceding or following Examples as active ingredient, are prepared as follows:

Composition

| | |
|---|---|
| Active ingredient | 250 g |
| PEG 400 | 1 liter |
| Tween 80 | 1 liter |

Preparation process: The powdered active ingredient is suspended in PEG 400 (polyethylene glycol of Mr between 380 and about 420, Sigma, Fluka, Aldrich, USA) and Tween® (polyoxyethylene sorbitan monolaurate, Atlas Chem. Inc., Inc., USA, supplied by Sigma, Fluka, Aldrich, USA) and ground in a wet-pulveriser to a particle size of about 1 to 3 mm. Portions of in each case 0.43 g of the mixture are then transferred to soft gelatine capsules by means of a capsule-filling machine.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

Compounds Prepared by the Method of Examples 4–7

| 8-AZAPURINE SUBSTITUENT | | | ANALYSES | | |
|---|---|---|---|---|---|
| C2 | C6 | N9 | CHNO | MS [M − H]⁻ | MS [M + H]⁺ |
| Chloro | benzylamino | Isopropyl | C = 55.3%; H = 5.06%; N = 27.77%; Cl = 11.85% | 301.1 303.1 | |
| Chloro | 3,4-dihydroxybenzylamino | Isopropyl | C = 50.56%; H = 4.39%; N = 24.95%; Cl = 10.68% | 333.1 335.1 | |
| Chloro | 3-chloroanilino | Isopropyl | C = 48.09%; H = 3.85%; N = 26.01%; Cl = 22.05% | 321.0 323.0 | |
| Chloro | anilino | Isopropyl | C = 54.23%; H = 4.39%; N = 29.02%; Cl = 12.36% | 287.1 289.1 | |
| Chloro | 4-carboxy-3-chloroanilino | Isopropyl | C = 45.97%; H = 3.06%; N = 23.75%; Cl = 22.75% | 335.0 337.0 | |
| Chloro | 3-carboxy-4-chloroanilino | Isopropyl | C = 45.86%; H = 3.12%; N = 22.91%; Cl = 19.44% | 365.0 367.0 | |
| Chloro | 3-carboxy-4-hydroxyanilino | Isopropyl | C = 48.40%; H = 3.61%; N = 23.96%; Cl = 10.26% | 367.1 369.1 | |
| Chloro | 4-bromoanilino | Isopropyl | C = 42.66%; H = 3.33%; N = 22.98%; Cl = 9.38% | 365.0 367.0 | |
| Chloro | 4-chloroanilino | Isopropyl | C = 48.12%; H = 3.95%; N = 26.08%; Cl = 21.85% | 321.0 323.0 | |
| Chloro | 3-amino-4-chloroanilino | Isopropyl | C = 46.00%; H = 3.91%; N = 28.97%; Cl = 21.12% | 336.0 333.0 | |
| Chloro | 4-amino-3-chloroanilino | Isopropyl | C = 46.27; H = 3.62%; N = 29.05%; Cl = 21.06% | 336.0 338.0 | |
| Chloro | 5-amino-3-chloroanilino | Isopropyl | C = 46.41; H = 3.72%; N = 28.75%; Cl = 21.15% | 336.0 338.0 | |
| Chloro | 2-hydroxybenzylamino | Isopropyl | C = 52.49; H = 4.95%; N = 26.28%; Cl = 11.35% | 317.1 319.1 | |
| Chloro | 3-hydroxybenzylamino | Isopropyl | C = 52.81%; H = 4.88%; N = 26.14%; Cl = 11.26% | 317.1 319.1 | |
| Chloro | 2-acetoxybenzylamino | Isopropyl | C = 53.51; H = 4.60%; N = 23.15%; Cl = 9.96% | 359.1 361.1 | |
| Chloro | 3-acetoxybenzylamino | Isopropyl | C = 53.42; H = 4.66%; N = 23.35%; Cl = 9.75% | 359.1 361.1 | |
| Chloro | 2-acetylbenzylamino | Isopropyl | C = 55.81%; H = 4.85%; N = 24.29%; Cl = 10.44% | 343.1 345.1 | |
| Chloro | 3-acetylbenzylamino | Isopropyl | C = 55.95%; H = 4.72%; N = 24.31%; Cl = 10.39% | 343.1 345.1 | |
| Chloro | 2-hydroxy-3-methoxybenzylamino | Isopropyl | C = 51.45%; H = 4.81%; N = 24.15%; Cl = 10.35% | 347.1 349.1 | |
| Chloro | 2-hydroxy-3-methylbenzylamino | Isopropyl | C = 54.02%; H = 5.29%; N = 25.35%; Cl = 10.44% | 331.1 333.1 | |
| Chloro | 3-chloro-2-hydroxybenzylamino | Isopropyl | C = 47.88%; H = 4.15%; N = 23.61%; Cl = 19.85% | 351.1 353.1 | |
| Chloro | 4-chloro-2,6-dihydroxybenzylamino | Isopropyl | C = 45.47%; H = 3.66%; N = 22.58%; Cl = 19.56% | 367.0 369.0 | |
| Chloro | 2,3-dihydroxy-4-methoxybenzylamino | Isopropyl | C = 49.15%; H = 4.86%; N = 22.76%; Cl = 9.89% | 363.1 365.1 | |
| Chloro | 2,5-dihydroxy-4-methoxybenzylamino | Isopropyl | C = 49.26%; H = 4.82%; N = 22.90%; Cl = 9.91% | 363.1 365.1 | |
| Chloro | 2,6-dihydroxy-4-methoxybenzylamino | Isopropyl | C = 49.46%; H = 4.71%; N = 23.11%; Cl = 9.65% | 363.1 365.1 | |

TABLE 1-continued

Compounds Prepared by the Method of Examples 4–7

| 8-AZAPURINE SUBSTITUENT | | | ANALYSES | | |
|---|---|---|---|---|---|
| C2 | C6 | N9 | CHNO | MS [M − H]⁻ | MS [M + H]⁺ |
| Chloro | 2,3-dihydroxy-4-chlorobenzylamino | Isopropyl | C = 45.66%; H = 3.71%; N = 22.61%; Cl = 19.44% | 367.0 369.0 | |
| Chloro | 4-chloro-2,5-dihydroxybenzylamino | Isopropyl | C = 45.70%; H = 3.95%; N = 22.40%; Cl = 19.31% | 367.0 369.0 | |
| Chloro | 2-amino-6-chlorobenzylamine | Isopropyl | C = 47.95.3%; H = 4.12%; N = 27.83%; Cl = 20.05% | 350.1 352.0 | |
| Chloro | 3-amino-4-chlorobenzylamine | Isopropyl | C = 48.00%; H = 4.19%; N = 27.55%; Cl = 20.26% | 350.1 352.0 | |
| Chloro | 4-chloro-2,3-diaminobenzylamine | Isopropyl | C = 45.52%; H = 4.61%; N = 30.61%; Cl = 19.25% | 365.1 362.0 | |
| Chloro | [(R,S)-(2-hydroxy-1-phenylethyl)amino] | Isopropyl | C = 54.31%; H = 5.02%; N = 25.15%; Cl = 10.91% | 331.1 333.1 | |
| Chloro | [N-(3,4-dihydroxybenzyl-N-methyl]amino | Isopropyl | C = 51.94%; H = 4.76%; N = 24.11%; Cl = 10.00% | 347.1 349.1 | |

TABLE 2

Compounds Prepared by the Method of Examples 7–13

| 8-AZAPURINE SUBSTITUENT | | | ANALYSES | | |
|---|---|---|---|---|---|
| C2 | C6 | | CHNO | MS [M − H]⁺ | MS [M + H]⁻ |
| 2-hydroxyethylamino | benzylamino | Isopropyl | C = 58.95%; H = 6.21%; N = 29.99% | 326.2 | |
| 3-hydroxypropylamino | benzylamino | Isopropyl | C = 59.48%; H = 6.96%; N = 28.92% | 340.2 | |
| Bis-(2-hydroxyethyl)amino | benzylamino | Isopropyl | C = 58.44%; H = 6.61%; N = 26.38% | 370.2 | |
| 2-aminocyclohexylamino | benzylamino | Isopropyl | C = 63.29%; H = 7.31%; N = 29.40% | | 381.3 |
| 4-aminocyclohexylamino | benzylamino | Isopropyl | C = 63.36%; H = 7.25%; N = 29.39% | | 381.3 |
| R-(1-hydroxymethyl)propylamino | benzylamino | Isopropyl | C = 60.59%; H = 7.25%; N = 27.69% | 354.2 | |
| R-(1-hydroxymethyl-2-methyl)propylamino | benzylamino | Isopropyl | C = 61.99%; H = 7.14%; N = 26.51% | 368.2 | |
| 3-aminopropylamino | benzylamino | Isopropyl | C = 60.25%; H = 7.00%; N = 32.80% | | 341.2 |
| 2-aminoethylamino | benzylamino | Isopropyl | C = 58.61%; H = 6.92%; N = 34.47% | | 327.2 |
| 2-hydroxyethylamino | 3,4-dihydroxybenzylamino | Isopropyl | C = 53.26%; H = 5.94%; N = 27.35% | 358.2 | |
| 3-hydroxypropylamino | 3,4-dihydroxybenzylamino | Isopropyl | C = 54.75%; H = 6.15%; N = 26.23% | 372.2 | |
| Bis-(2-hydroxyethyl)amino | 3,4-dihydroxybenzylamino | Isopropyl | C = 55.31%; H = 6.03%; N = 22.75% | 402.2 | |
| 2-aminocyclohexylamino | 3,4-dihydroxybenzylamino | Isopropyl | C = 57.95%; H = 6.95%; N = 27.30% | | 413.2 |
| 4-aminocyclohexylamino | 3,4-dihydroxybenzylamino | Isopropyl | C = 58.00%; H = 6.65%; N = 27.36% | | 413.2 |
| R-(1-hydroxymethyl)propylamino | 3,4-dihydroxybenzylamino | Isopropyl | C = 55.65%; H = 6.61%; N = 25.34% | 386.2 | |
| R-(1-hydroxymethyl-2-methyl)propylamino | 3,4-dihydroxybenzylamino | Isopropyl | C = 56.71%; H = 6.86%; N = 24.41% | 400.2 | |
| 3-aminopropylamino | 3,4-dihydroxybenzylamino | Isopropyl | C = 54.98%; H = 6.35%; N = 30.15% | 371.2 | |
| 2-aminoethylamino | 3,4-dihydroxybenzylamino | Isopropyl | C = 53.90%; H = 6.04%; N = 31.10% | 357.2 | |
| 2-hydroxyethylamino | 3-chloroanilino | Isopropyl | C = 51.62%; H = 5.35%; N = 28.20%; Cl = 10.25% | 346.1 348.1 | |
| 3-hydroxypropylamino | 3-chloroanilino | Isopropyl | C = 52.90%; H = 5.64%; N = 27.15%; Cl = 9.95% | 360.1 362.1 | |
| Bis-(2-hydroxyethyl)amino | 3-chloroanilino | Isopropyl | C = 52.40%; H = 5.31%; N = 25.15%; Cl = 8.86% | 390.1 392.1 | |
| 2-aminocyclohexylamino | 3-chloroanilino | Isopropyl | C = 56.81%; H = 6.31%; N = 27.90%; Cl = 8.98% | 399.2 401.2 | |
| 4-aminocyclohexylamino | 3-chloroanilino | Isopropyl | C = 57.15%; H = 6.20%; N = 27.75%; Cl = 9.00% | 399.2 401.2 | |
| R-(1- | 3-chloroanilino | Isopropyl | C = 54.00%; H = 6.12%; | 374.1 | |

TABLE 2-continued

Compounds Prepared by the Method of Examples 7–13

| 8-AZAPURINE SUBSTITUENT | | | ANALYSES | | |
|---|---|---|---|---|---|
| C2 | C6 | | CHNO | MS [M − H]+ | MS [M + H]− |
| hydroxymethyl)propylamino | | | N = 26.25%; Cl = 9.31% | 376.1 | |
| R-(1-hydroxymethyl)propylamino | 3-chloroanilino | Isopropyl | C = 55.64%; H = 6.00%; N = 25.10%; Cl = 9.25% | 388.2 390.2 | |
| 3-aminopropylamino | 3-chloroanilino | Isopropyl | C = 53.59%; H = 5.65%; N = 31.15%; Cl = 9.61% | 359.2 361.2 | |
| 2-aminoethylamino | 3-chloroanilino | Isopropyl | C = 52.23%; H = 5.38%; N = 32.25%; Cl = 10.14% | 345.1 347.1 | |
| 2-hydroxyethylamino | oanilino | Isopropyl | C = 57.20%; H = 6.25%; N = 31.35% | 312.2 | |
| 3-hydroxypropylamino | anilino | Isopropyl | C = 58.96%; H = 6.29%; N = 29.90% | 326.2 | |
| Bis-(2-hydroxyethyl)amino | anilino | Isopropyl | C = 57.45%; H = 6.26%; N = 27.30% | 356.2 | |
| 2-aminocyclohexylamino | anilino | Isopropyl | C = 62.10%; H = 7.21%; N = 30.69% | | 367.2 |
| 4-aminocyclohexylamino | anilino | Isopropyl | C = 62.02%; H = 7.34%; N = 30.64% | | 367.2 |
| R-(1-hydroxymethyl)propylamino | anilino | Isopropyl | C = 59.56%; H = 6.88%; N = 28.86% | 340.2 | |
| R-(1-hydroxymethyl-2-methyl)propylamino | anilino | Isopropyl | C = 60.56%; H = 7.00%; N = 27.91% | 354.2 | |
| 3-aminopropylamino | anilino | Isopropyl | C = 58.65%; H = 6.88%; N = 34.47% | | 327.2 |
| 2-aminoethylamino | anilino | Isopropyl | C = 58.05%; H = 6.26%; N = 35.69% | | 313.2 |
| 2-hydroxyethylamino | 4-carboxy-3-chloroanilino | Isopropyl | C = 48.77%; H = 4.79%; N = 25.10%; Cl = 9.23% | 390.1 392.1 | |
| 3-hydroxypropylamino | 4-carboxy-3-chloroanilino | Isopropyl | C = 50.14%; H = 5.15%; N = 24.05%; Cl = 8.80% | 404.1 406.1 | |
| Bis-(2-hydroxyethyl)amino | 4-carboxy-3-chloroanilino | Isopropyl | C = 49.91%; H = 5.20%; N = 22.21%; Cl = 8.29% | 434.1 436.1 | |
| 2-aminocyclohexylamino | 4-carboxy-3-chloroanilino | Isopropyl | C = 53.58%; H = 5.82%; N = 25.27%; Cl = 8.05% | 443.2 445.2 | |
| 4-aminocyclohexylamino | 4-carboxy-3-chloroanilino | Isopropyl | C = 54.15%; H = 5.60%; N = 25.30%; Cl = 7.75% | 443.2 445.2 | |
| R-(1-hydroxymethyl)propylamino | 4-carboxy-3-chloroanilino | Isopropyl | C = 51.73%; H = 5.12%; N = 23.16%; Cl = 8.44% | 418.1 420.1 | |
| R-(1-hydroxymethyl-2-methyl)propylamino | 4-carboxy-3-chloroanilino | Isopropyl | C = 52.82%; H = 5.60%; N = 22.25%; Cl = 8.35% | 432.2 434.2 | |
| 3-aminopropylamino | 4-carboxy-3-chloroanilino | Isopropyl | C = 50.12%; H = 5.35%; N = 27.80%; Cl = 8.89% | 403.1 405.1 | |
| 2-aminoethylamino | 4-carboxy-3-chloroanilino | Isopropyl | C = 49.32%; H = 5.21%; N = 28.51%; Cl = 9.91% | 389.1 391.1 | |
| 2-hydroxyethylamino | 3-carboxy-4-chloroanilino | Isopropyl | C = 49.35%; H = 4.40%; N = 24.85%; Cl = 9.25% | 390.1 392.1 | |
| 3-hydroxypropylamino | 3-carboxy-4-chloroanilino | Isopropyl | C = 50.05%; H = 5.15%; N = 24.85%; Cl = 9.25% | 404.1 406.1 | |
| Bis-(2-hydroxyethyl)amino | 3-carboxy-4-chloroanilino | Isopropyl | C = 49.35%; H = 5.25%; N = 22.56%; Cl = 8.31% | 434.1 436.1 | |
| 2-aminocyclohexylamino | 3-carboxy-4-chloroanilino | Isopropyl | C = 54.26%; H = 5.31%; N = 25.01%; Cl = 8.15% | 443.2 445.2 | |
| 4-aminocyclohexylamino | 3-carboxy-4-chloroanilino | Isopropyl | C = 54.18%; H = 5.48%; N = 25.20%; Cl = 8.02% | 443.2 445.2 | |
| R-(1-hydroxymethyl)propylamino | 3-carboxy-4-chloroanilino | Isopropyl | C = 51.23%; H = 5.35%; N = 23.42%; Cl = 8.20% | 418.1 420.1 | |
| R-(1-hydroxymethyl-2-methyl)propylamino | 3-carboxy-4-chloroanilino | Isopropyl | C = 52.45%; H = 5.31%; N = 22.65%; Cl = 8.44% | 432.2 434.2 | |
| 3-aminopropylamino | 3-carboxy-4-chloroanilino | Isopropyl | C = 50.61%; H = 5.00%; N = 27.95%; Cl = 8.44% | 403.1 405.1 | |
| 2-aminoethylamino | 3-carboxy-4-chloroanilino | Isopropyl | C = 49.35%; H = 4.80%; N = 28.40%; Cl = 9.21% | 389.1 391.1 | |
| 2-hydroxyethylamino | 3-carboxy-4-hydroxyanilino | Isopropyl | C = 51.35%; H = 5.31%; N = 26.20% | 372.1 | |
| 3-hydroxypropylamino | 3-carboxy-4-hydroxyanilino | Isopropyl | C = 52.60%; H = 5.57%; N = 25.21% | 386.2 | |
| Bis-(2-hydroxyethyl)amino | 3-carboxy-4-hydroxyanilino | Isopropyl | C = 51.95%; H = 5.38%; N = 23.49% | 416.2 | |
| 2-aminocyclohexylamino | 3-carboxy-4-hydroxyanilino | Isopropyl | C = 56.44%; H = 6.02%; N = 26.30% | 425.2 | |
| 4-aminocyclohexylamino | 3-carboxy-4-hydroxyanilino | Isopropyl | C = 56.39%; H = 5.95%; N = 26.35% | 425.2 | |
| R-(1-hydroxymethyl)propylamino | 3-carboxy-4-hydroxyanilino | Isopropyl | C = 57.65%; H = 5.88%; N = 20.51% | 400.2 | |

TABLE 2-continued

Compounds Prepared by the Method of Examples 7–13

| 8-AZAPURINE SUBSTITUENT | | | ANALYSES | | |
|---|---|---|---|---|---|
| C2 | C6 | | CHNO | MS [M − H]+ | MS [M + H]− |
| R-(1-hydroxymethyl-2-methyl)propylamino | 3-carboxy-4-hydroxyanilino | Isopropyl | C = 54.77%; H = 6.19%; N = 23.68% | 414.2 | |
| 3-aminopropylamino | 3-carboxy-4-hydroxyanilino | Isopropyl | C = 52.71%; H = 5.81%; N = 20.15% | 385.2 | |
| 2-aminoethylamino | 3-carboxy-4-hydroxyanilino | Isopropyl | C = 51.49%; H = 5.65%; N = 29.85% | 371.2 | |
| 2-hydroxyethylamino | 4-bromoanilino | Isopropyl | C = 46.11%; H = 4.43%; N = 24.92%; Br = 20.55% | 390.1 392.1 | |
| 3-hydroxypropylamino | 4-bromoanilino | Isopropyl | C = 47.44%; H = 4.77%; N = 23.92%; Br = 20.01% | 404.1 406.1 | |
| Bis-(2-hydroxyethyl)amino | 4-bromoanilino | Isopropyl | C = 46.61%; H = 5.16%; N = 22.65%; Br = 18.15% | 434.1 436.1 | |
| 2-aminocyclohexylamino | 4-bromoanilino | Isopropyl | C = 51.36%; H = 5.25%; N = 25.27%; Br = 18.12% | | 445.1 447.1 |
| 4-aminocyclohexylamino | 4-bromoanilino | Isopropyl | C = 51.45%; H = 5.34%; N = 25.36%; Br = 17.85% | | 445.1 447.1 |
| R-(1-hydroxymethyl)propylamino | 4-bromoanilino | Isopropyl | C = 48.77%; H = 5.11%; N = 23.22%; Br = 19.15% | 418.1 420.1 | |
| R-(1-hydroxymethyl-2-methyl)propylamino | 4-bromoanilino | Isopropyl | C = 49.52%; H = 5.69%; N = 22.53%; Br = 18.55% | 432.1 434.1 | |
| 3-aminopropylamino | 4-bromoanilino | Isopropyl | C = 47.35%; H = 5.44%; N = 27.23%; Br = 19.98% | | 405.1 407.1 |
| 2-aminoethylamino | 4-bromoanilino | Isopropyl | C = 46.27%; H = 4.65%; N = 28.93%; Br = 20.15 | | 391.1 393.1 |
| 2-hydroxyethylamino | 4-chloroanilino | Isopropyl | C = 51.62%; H = 5.44%; N = 28.35%; Cl = 10.05% | 346.1 348.1 | |
| 3-hydroxypropylamino | 4-chloroanilino | Isopropyl | C = 53.46%; H = 5.31%; N = 26.94%; Cl = 9.96% | 360.1 362.1 | |
| Bis-(2-hydroxyethyl)amino | 4-chloroanilino | Isopropyl | C = 52.44%; H = 5.85%; N = 24.65%; Cl = 9.23% | 390.1 392.1 | |
| 2-aminocyclohexylamino | 4-chloroanilino | Isopropyl | C = 56.75%; H = 6.48%; N = 27.86%; Cl = 9.01% | 399.2 401.2 | |
| 4-aminocyclohexylamino | 4-chloroanilino | Isopropyl | C = 56.88%; H = 6.35%; N = 27.83%; Cl = 8.94% | 399.2 401.2 | |
| R-(1-hydroxymethyl)propylamino | 4-chloroanilino | Isopropyl | C = 54.51%; H = 5.75%; N = 26.15%; Cl = 19.27% | 374.1 376.1 | |
| R-(1-hydroxymethyl-2-methyl)propylamino | 4-chloroanilino | Isopropyl | C = 55.67%; H = 6.12%; N = 24.96%; Cl = 9.19% | 388.2 390.2 | |
| 3-aminopropylamino | 4-chloroanilino | Isopropyl | C = 53.39%; H = 5.95%; N = 31.01%; Cl = 19.65% | 359.2 361.2 | |
| 2-aminoethylamino | 4-chloroanilino | Isopropyl | C = 52.15%; H = 5.41%; N = 32.07%; Cl = 10.37% | 345.1 347.1 | |
| 2-hydroxyethylamino | 3-amino-4-chloroanilino | Isopropyl | C = 49.85%; H = 5.04%; N = 30.71%; Cl = 10.01% | 361.1 363.1 | |
| 3-hydroxypropylamino | 3-amino-4-chloroanilino | Isopropyl | C = 50.76%; H = 5.88%; N = 29.62%; Cl = 9.65% | 375.1 377.1 | |
| Bis-(2-hydroxyethyl)amino | 3-amino-4-chloroanilino | Isopropyl | C = 50.37%; H = 5.49%; N = 27.49%; Cl = 8.85% | 405.2 407.2 | |
| 2-aminocyclohexylamino | 3-amino-4-chloroanilino | Isopropyl | C = 54.61%; H = 6.48%; N = 30.16%; Cl = 8.75% | | 416.2 418.2 |
| 4-aminocyclohexylamino | 3-amino-4-chloroanilino | Isopropyl | C = 54.74%; H = 6.51%; N = 29.93%; Cl = 8.81% | | 416.2 418.2 |
| R-(1-hydroxymethyl)propylamino | 3-amino-4-chloroanilino | Isopropyl | C = 52.52%; H = 5.71%; N = 28.70%; Cl = 8.92% | 389.2 391.2 | |
| R-(1-hydroxymethyl-2-methyl)propylamino | 3-amino-4-chloroanilino | Isopropyl | C = 55.25%; H = 6.45%; N = 27.51%; Cl = 8.95% | 403.2 405.2 | |
| 3-aminopropylamino | 3-amino-4-chloroanilino | Isopropyl | C = 51.38%; H = 5.60%; N = 33.33%; Cl = 9.69% | | 376.2 378.2 |
| 2-aminoethylamino | 3-amino-4-chloroanilino | Isopropyl | C = 49.50%; H = 5.85%; N = 34.97%; Cl = 9.68% | | 362.2 364.4 |
| 2-hydroxyethylamino | 4-amino-3-chloroanilino | Isopropyl | C = 49.88%; H = 5.12%; N = 30.66%; Cl = 10.01% | 342.2 | |
| 3-hydroxypropylamino | 4-amino-3-chloroanilino | Isopropyl | C = 51.29%; H = 5.38%; N = 29.49%; Cl = 9.70% | 356.2 | |
| Bis-(2-hydroxyethyl)amino | 4-amino-3-chloroanilino | Isopropyl | C = 49.95%; H = 5.81%; N = 27.50%; Cl = 8.90% | 386.2 | |
| 2-aminocyclohexylamino | 4-amino-3-chloroanilino | Isopropyl | C = 54.99%; H = 6.18%; N = 30.17%; Cl = 8.66% | | 397.2 |
| 4-aminocyclohexylamino | 4-amino-3-chloroanilino | Isopropyl | C = 55.05%; H = 6.21%; N = 30.30%; Cl = 8.44% | | 397.2 |
| R-(1-hydroxymethyl)propylamino | 4-amino-3-chloroanilino | Isopropyl | C = 52.42%; H = 5.98%; N = 28.42%; Cl = 9.07% | 389.2 391.2 | |
| R-(1-hydroxymethyl-2- | 4-amino-3- | Isopropyl | C = 53.58%; H = 6.04%; | 403.2 | |

TABLE 2-continued

Compounds Prepared by the Method of Examples 7–13

| 8-AZAPURINE SUBSTITUENT | | | ANALYSES | | |
|---|---|---|---|---|---|
| C2 | C6 | | CHNO | MS [M − H]+ | MS [M + H]− |
| methyl)propylamino | chloroanilino | | N = 27.70%; Cl = 8.65% | 405.2 | |
| 3-aminopropylamino | 4-amino-3-chloroanilino | Isopropyl | C = 51.32%; H = 5.68%; N = 33.34%; Cl = 9.66% | | 376.2 378.2 |
| 2-aminoethylamino | 4-amino-3-chloroanilino | Isopropyl | C = 49.92%; H = 5.36%; N = 34.94%; Cl = 9.78% | | 362.2 364.2 |
| 2-hydroxyethylamino | 2-hydroxybenzylamino | Isopropyl | C = 56.15%; H = 6.38%; N = 28.29% | 344.2 | |
| 3-hydroxypropylamino | 2-hydroxybenzylamino | Isopropyl | C = 56.89%; H = 6.75%; N = 27.42% | 358.2 | |
| Bis-(2-hydroxyethyl)amino | 2-hydroxybenzylamino | Isopropyl | C = 55.71%; H = 6.80%; N = 25.15% | 388.2 | |
| 2-aminocyclohexylamino | 2-hydroxybenzylamino | Isopropyl | C = 60.81%; H = 7.05%; N = 28.15% | | 397.2 |
| 4-aminocyclohexylamino | 2-hydroxybenzylamino | Isopropyl | C = 60.45%; H = 7.28%; N = 28.20% | | 397.2 |
| R-(1-hydroxymethyl)propylamino | 2-hydroxybenzylamino | Isopropyl | C = 58.35%; H = 6.93%; N = 26.25% | 372.2 | |
| R-(1-hydroxymethyl-2-methyl)propylamino | 2-hydroxybenzylamino | Isopropyl | C = 59.31%; H = 7.15%; N = 25.24% | 386.2 | |
| 3-aminopropylamino | 2-hydroxybenzylamino | Isopropyl | C = 57.14%; H = 6.85%; N = 31.50% | | 355.2 |
| 2-aminoethylamino | 2-hydroxybenzylamino | Isopropyl | C = 56.22%; H = 6.57%; N = 32.61% | | 341.2 |
| 2-hydroxyethylamino | 3-hydroxybenzylamino | Isopropyl | C = 55.81%; H = 6.29%; N = 28.59% | 344.2 | |
| 3-hydroxypropylamino | 3-hydroxybenzylamino | Isopropyl | C = 56.91%; H = 6.55%; N = 27.50% | 358.2 | |
| Bis-(2-hydroxyethyl)amino | 3-hydroxybenzylamino | Isopropyl | C = 55.69%; H = 6.41%; N = 25.48% | 388.2 | |
| 2-aminocyclohexylamino | 3-hydroxybenzylamino | Isopropyl | C = 60.44%; H = 7.21%; N = 28.29% | | 395.2 |
| 4-aminocyclohexylamino | 3-hydroxybenzylamino | Isopropyl | C = 60.72%; H = 7.08%; N = 28.21% | | 395.2 |
| R-(1-hydroxymethyl)propylamino | 3-hydroxybenzylamino | Isopropyl | C = 58.08%; H = 6.61%; N = 26.65% | 372.2 | |
| R-(1-hydroxymethyl-2-methyl)propylamino | 3-hydroxybenzylamino | Isopropyl | C = 59.38%; H = 7.23%; N = 25.21% | 386.2 | |
| 3-aminopropylamino | 3-hydroxybenzylamino | Isopropyl | C = 56.95%; H = 6.84%; N = 31.70% | | 355.2 |
| 2-aminoethylamino | 3-hydroxybenzylamino | Isopropyl | C = 56.30%; H = 6.35%; N = 32.71% | | 341.2 |
| 2-hydroxyethylamino | 2-acetoxybenzylamino | Isopropyl | C = 56.13%; H = 6.25%; N = 25.25% | 384.2 | |
| 3-hydroxypropylamino | 2-acetoxybenzylamino | Isopropyl | C = 57.36%; H = 6.21%; N = 24.40% | 398.2 | |
| Bis-(2-hydroxyethyl)amino | 2-acetoxybenzylamino | Isopropyl | C = 55.72%; H = 6.95%; N = 22.95% | 428.2 | |
| 2-aminocyclohexylamino | 2-acetoxybenzylamino | Isopropyl | C = 60.15%; H = 6.82%; N = 25.70% | | 439.3 |
| 4-aminocyclohexylamino | 2-acetoxybenzylamino | Isopropyl | C = 60.15%; H = 6.82%; N = 25.70%; | | 439.3 |
| R-(1-hydroxyethyl)propylamino | 2-acetoxybenzylamino | Isopropyl | C = 58.41%; H = 6.32%; N = 23.69% | 412.2 | |
| R-(1-hydroxymethyl-2-methyl)propylamino | 2-acetoxybenzylamino | Isopropyl | C = 59.25%; H = 6.95%; N = 22.68% | 426.2 | |
| 3-aminopropylamino | 2-acetoxybenzylamino | Isopropyl | C = 57.02%; H = 6.68%; N = 28.20% | | 399.2 |
| 2-aminoethylamino | 2-acetoxybenzylamino | Isopropyl | C = 56.50%; H = 6.10%; N = 29.12% | | 385.2 |
| 2-hydroxyethylamino | 3-acetoxybenzylamino | Isopropyl | C = 56.23%; H = 6.12%; N = 25.29% | 384.2 | |
| 3-hydroxypropylamino | 3-acetoxybenzylamino | Isopropyl | C = 56.95%; H = 6.39%; N = 24.60% | 398.2 | |
| Bis-(2-hydroxyethyl)amino | 3-acetoxybenzylamino | Isopropyl | C = 55.81%; H = 6.50%; N = 22.63% | 428.2 | |
| 2-aminocyclohexylamino | 3-acetoxybenzylamino | Isopropyl | C = 60.44%; H = 7.06%; N = 25.34% | | 439.3 |
| 4-aminocyclohexylamino | 3-acetoxybenzylamino | Isopropyl | C = 60.36%; H = 6.81%; N = 25.50% | | 439.3 |
| R-(1-hydroxymethyl)propylamino | 3-acetoxybenzylamino | Isopropyl | C = 58.44%; H = 6.41%; N = 23.59% | 412.2 | |
| R-(1-hydroxymethyl-2-methyl)propylamino | 3-acetoxybenzylamino | Isopropyl | C = 59.15%; H = 6.96%; N = 22.78% | 426.2 | |

TABLE 2-continued

Compounds Prepared by the Method of Examples 7–13

| 8-AZAPURINE SUBSTITUENT | | | ANALYSES | | |
|---|---|---|---|---|---|
| C2 | C6 | | CHNO | MS [M − H]+ | MS [M + H]− |
| 3-aminopropylamino | 3-acetoxybenzylamino | Isopropyl | C = 57.49%; H = 6.44%; N = 28.10% | | 399.2 |
| 2-aminoethylamino | 3-acetoxybenzylamino | Isopropyl | C = 56.09%; H = 6.38%; N = 29.20% | | 385.2 |
| 2-hydroxyethylamino | 2-acetylbenzylamino | Isopropyl | C = 58.32%; H = 6.39%; N = 26.69% | 368.2 | |
| 3-hydroxypropylamino | 2-acetylbenzylamino | Isopropyl | C = 59.41%; H = 6.41%; N = 25.70% | 382.2 | |
| Bis-(2-hydroxyethyl)amino | 2-acetylbenzylamino | Isopropyl | C = 58.44%; H = 6.69%; N = 23.40% | 412.2 | |
| 2-aminocyclohexylamino | 2-acetylbenzylamino | Isopropyl | C = 62.39%; H = 7.28%; N = 26.59% | | 423.3 |
| 4-aminocyclohexylamino | 2-acetylbenzylamino | Isopropyl | C = 62.31%; H = 7.05%; N = 26.71% | | 423.3 |
| R-(1-hydroxymethyl)propylamino | 2-acetylbenzylamino | Isopropyl | C = 60.32%; H = 6.62%; N = 24.95% | 396.2 | |
| R-(1-hydroxymethyl-2-methyl)propylamino | 2-acetylbenzylamino | Isopropyl | C = 61.06%; H = 7.31%; N = 23.80% | 410.2 | |
| 3-aminopropylamino | 2-acetylbenzylamino | Isopropyl | C = 59.88%; H = 6.71%; N = 29.29% | | 383.2 |
| 2-aminoethylamino | 2-acetylbenzylamino | Isopropyl | C = 58.71%; H = 6.78%; N = 30.31% | | 369.2 |
| 2-hydroxyethylamino | 3-acetylbenzylamino | Isopropyl | C = 58.66%; H = 6.02%; N = 26.20% | 368.2 | |
| 3-hydroxypropylamino | 3-acetylbenzylamino | Isopropyl | C = 59.35%; H = 6.44%; N = 25.75% | 382.2 | |
| Bis-(2-hydroxyethyl)amino | 3-acetylbenzylamino | Isopropyl | C = 58.22%; H = 6.43%; N = 23.65% | 412.2 | |
| 2-aminocyclohexylamino | 3-acetylbenzylamino | Isopropyl | C = 62.31%; H = 7.29%; N = 26.58% | | 423.3 |
| 4-aminocyclohexylamino | 3-acetylbenzylamino | Isopropyl | C = 62.25%; H = 7.33%; N = 26.70% | | 423.3 |
| R-(1-hydroxymethyl)propylamino | 3-acetylbenzylamino | Isopropyl | C = 60.15%; H = 6.75%; N = 24.91% | 396.2 | |
| R-(1-hydroxymethyl-2-methyl)propylamino | 3-acetylbenzylamino | Isopropyl | C = 61.05%; H = 7.22%; N = 23.98% | 410.2 | |
| 3-aminopropylamino | 3-acetylbenzylamino | Isopropyl | C = 59.91%; H = 6.74%; N = 29.25% | | 383.2 |
| 2-aminoethylamino | 3-acetylbenzylamino | Isopropyl | C = 58.90%; H = 6.45%; N = 30.35% | | 369.2 |
| 2-hydroxyethylamino | 2-hydroxy-3-methoxybenzylamino | Isopropyl | C = 54.33%; H = 6.41%; N = 26.45% | 372.2 | |
| 3-hydroxypropylamino | 2-hydroxy-3-methoxybenzylamino | Isopropyl | C = 55.96%; H = 6.77%; N = 25.10% | 386.2 | |
| Bis-(2-hydroxyethyl)amino | 2-hydroxy-3-methoxybenzylamino | Isopropyl | C = 54.81%; H = 6.35%; N = 23.57% | 416.2 | |
| 2-aminocyclohexylamino | 2-hydroxy-3-methoxybenzylamino | Isopropyl | C = 59.35%; H = 7.01%; N = 26.21% | | 427.3 |
| 4-aminocyclohexylamino | 2-hydroxy-3-methoxybenzylamino | Isopropyl | C = 59.02%; H = 7.14%; N = 26.30% | | 427.3 |
| R-(1-hydroxymethyl)propylamino | 2-hydroxy-3-methoxybenzylamino | Isopropyl | C = 56.65%; H = 6.91%; N = 24.51% | 400.2 | |
| R-(1-hydroxymethyl-2-methyl)propylamino | 2-hydroxy-3-methoxybenzylamino | Isopropyl | C = 57.94%; H = 6.85%; N = 23.70% | 414.2 | |
| 3-aminopropylamino | 2-hydroxy-3-methoxybenzylamino | Isopropyl | C = 55.69%; H = 6.98%; N = 29.08% | | 387.2 |
| 2-aminoethylamino | 2-hydroxy-3-methoxybenzylamino | Isopropyl | C = 54.98%; H = 6.35%; N = 30.14% | | 373.2 |
| 2-hydroxyethylamino | 2-hydroxy-3-methoxybenzylamino | Isopropyl | C = 57.33%; H = 6.24%; N = 27.52% | 356.2 | |
| 3-hydroxypropylamino | 2-hydroxy-3-methylbenzylamino | Isopropyl | C = 58.41%; H = 6.62%; N = 26.31% | 370.2 | |
| Bis-(2-hydroxyethyl)amino | 2-hydroxy-3-methylbenzylamino | Isopropyl | C = 56.69%; H = 6.95%; N = 24.35% | 400.2 | |
| 2-aminocyclohexylamino | 2-hydroxy-3-methylbenzylamino | Isopropyl | C = 61.70%; H = 7.15%; N = 27.21% | | 411.3 |
| 4-aminocyclohexylamino | 2-hydroxy-3-methylbenzylamino | Isopropyl | C = 61.54%; H = 7.29%; N = 27.25% | | 411.3 |
| R-(1-hydroxymethyl)propylamino | 2-hydroxy-3-methylbenzylamino | Isopropyl | C = 59.39%; H = 7.25%; N = 25.21% | 384.2 | |
| R-(1-hydroxymethyl-2-methyl)propylamino | 2-hydroxy-3-methylbenzylamino | Isopropyl | C = 60.35%; H = 7.44%; N = 24.32% | 398.2 | |
| 3-aminopropylamino | 2-hydroxy-3- | Isopropyl | C = 58.21%; H = 7.14%; | | 371.2 |

TABLE 2-continued

Compounds Prepared by the Method of Examples 7–13

| 8-AZAPURINE SUBSTITUENT | | | ANALYSES | | |
|---|---|---|---|---|---|
| C2 | C6 | | CHNO | MS [M – H]+ | MS [M + H]− |
| 2-aminoethylamino | methylbenzylamino 2-hydroxy-3-methylbenzylamino | Isopropyl | N = 30.30% C = 57.48%; H = 6.95%; N = 31.25% | | 357.2 |
| 2-hydroxyethylamino | 3-chloro-2-hydroxybenzylamino | Isopropyl | C = 50.76%; H = 5.49%; N = 25.78%; Cl = 9.65% | 376.1 378.1 | |
| 3-hydroxypropylamino | 3-chloro-2-hydroxybenzylamino | Isopropyl | C = 52.43%; H = 5.49%; N = 24.80%; Cl = 9.15% | 390.1 392.1 | |
| Bis-(2-hydroxyethyl)amino | 3-chloro-2-hydroxybenzylamino | Isopropyl | C = 51.06%; H = 5.91%; N = 23.16%; Cl = 8.56% | 420.2 422.2 | |
| 2-aminocyclohexylamino | 3-chloro-2-hydroxybenzylamino | Isopropyl | C = 55.86%; H = 6.15%; N = 25.91%; Cl = 8.39% | 429.2 431.2 | |
| 4-aminocyclohexylamino | 3-chloro-2-hydroxybenzylamino | Isopropyl | C = 55.81%; H = 6.42%; N = 25.80%; Cl = 8.19% | 429.2 431.2 | |
| R-(1-hydroxymethyl)propylamino | 3-chloro-2-hydroxybenzylamino | Isopropyl | C = 53.41%; H = 6.05%; N = 23.95%; Cl = 8.86% | 404.2 406.2 | |
| R-(1-hydroxymethyl-2-methyl)propylamino | 3-chloro-2-hydroxybenzylamino | Isopropyl | C = 54.12%; H = 6.38%; N = 23.31%; Cl = 8.59% | 418.2 420.2 | |
| 3-aminopropylamino | 3-chloro-2-hydroxybenzylamino | Isopropyl | C = 52.40%; H = 5.86%; N = 28.75%; Cl = 8.95% | 389.2 391.2 | |
| 2-aminoethylamino | 3-chloro-2-hydroxybenzylamino | Isopropyl | C = 50.84%; H = 5.77%; N = 26.80%; Cl = 9.28% | 375.1 377.1 | |
| 2-hydroxyethylamino | 2,6-dihydroxy-4-chlorobenzylamino | Isopropyl | C = 49.05%; H = 5.02%; N = 24.48%; Cl = 9.12% | 392.1 394.1 | |
| 3-hydroxypropylamino | 2,6-dihydroxy-4-chlorobenzylamino | Isopropyl | C = 49.85%; H = 5.69%; N = 23.85%; Cl = 8.76% | 406.6 408.1 | |
| Bis-(2-hydroxyethyl)amino | 2,6-dihydroxy-4-chlorobenzylamino | Isopropyl | C = 49.55%; H = 5.68%; N = 22.18%; Cl = 8.20% | 436.2 438.2 | |
| 2-aminocyclohexylamino | 2,6-dihydroxy-4-chlorobenzylamino | Isopropyl | C = 53.64%; H = 6.15%; N = 25.12%; Cl = 8.00% | 445.2 447.2 | |
| 4-aminocyclohexylamino | 2,6-dihydroxy-4-chlorobenzylamino | Isopropyl | C = 53.80%; H = 6.20%; N = 24.85%; Cl = 8.05% | 445.2 447.2 | |
| R-(1-hydroxymethyl)propylamino | 2,6-dihydroxy-4-chlorobenzylamino | Isopropyl | C = 51.47%; H = 5.81%; N = 23.15%; Cl = 8.31% | 420.2 422.2 | |
| R-(1-hydroxymethyl-2-methyl)propylamino | 2,6-dihydroxy-4-chlorobenzylamino | Isopropyl | C = 52.21%; H = 6.16%; N = 22.40%; Cl = 8.25% | 434.2 436.2 | |
| 3-aminopropylamino | 2,6-dihydroxy-4-chlorobenzylamino | Isopropyl | C = 50.06%; H = 5.90%; N = 27.59%; Cl = 8.62% | 405.2 407.2 | |
| 2-aminoethylamino | 2,6-dihydroxy-4-chlorobenzylamino | Isopropyl | C = 49.15%; H = 5.15%; N = 28.60%; Cl = 8.86% | 391.1 393.1 | |
| 2-hydroxyethylamino | 2,3-dihydroxy-4-methoxybenzylamino | Isopropyl | C = 52.19%; H = 6.14%; N = 25.27% | 388.2 | |
| 3-hydroxypropylamino | 2,3-dihydroxy-4-methoxybenzylamino | Isopropyl | C = 53.40%; H = 6.39%; N = 24.39% | 402.2 | |
| Bis-(2-hydroxyethyl)amino | 2,3-dihydroxy-4-methoxybenzylamino | Isopropyl | C = 52.49%; H = 6.45%; N = 22.57% | 432.2 | |
| 2-aminocyclohexylamino | 2,3-dihydroxy-4-methoxybenzylamino | Isopropyl | C = 57.25%; H = 6.71%; N = 25.26% | 441.2 | |
| 4-aminocyclohexylamino | 2,3-dihydroxy-4-methoxybenzylamino | Isopropyl | C = 57.19%; H = 5.19%; N = 25.21% | 44 1.2 | |
| R-(1-hydroxymethyl)propylamino | 2,3-dihydroxy-4-methoxybenzylamino | Isopropyl | C = 54.82%; H = 6.41%; N = 23.40% | 416.2 | |
| R-(1-hydroxymethyl-2-methyl)propylamino | 2,3-dihydroxy-4-methoxybenzylamino | Isopropyl | C = 55.39%; H = 6.90%; N = 22.85% | 430.2 | |
| 3-aminopropylamino | 2,3-dihydroxy-4-methoxybenzylamino | Isopropyl | C = 53.95%; H = 6.38%; N = 27.69% | 401.2 | |
| 2-aminoethylamino | 2,3-dihydroxy-4-methoxybenzylamino | Isopropyl | C = 52.42%; H = 6.14%; N = 28.81% | 387.2 | |
| 2-hydroxyethylamino | 2,5-dihydroxy-4-methoxybenzylamino | Isopropyl | C = 52.61%; H = 5.80%; N = 25.09% | 388.2 | |
| 3-hydroxypropylamino | 2,5-dihydroxy-4-methoxybenzylamino | Isopropyl | C = 53.31%; H = 6.45%; N = 24.42% | 402.2 | |
| Bis-(2-hydroxyethyl)amino | 2,5-dihydroxy-4-methoxybenzylamino | Isopropyl | C = 52.79%; H = 6.06%; N = 22.75% | 432.2 | |
| 2-aminocyclohexylamino | 2,5--dihydroxy-4-methoxybenzylamino | Isopropyl | C = 56.85%; H = 6.98%; N = 25.45% | 441.2 | |
| 4-aminocyclohexylamino | 2,5-dihydroxy-4-methoxybenzylamino | Isopropyl | C = 57.15%; H = 6.77%; N = 25.20% | 441.2 | |
| R-(1-hydroxymethyl)propylamino | 2,5-dihydroxy-4-methoxybenzylamino | Isopropyl | C = 54.46%; H = 6.79%; N = 23.40% | 416.2 | |
| R-(1-hydroxymethyl-2-methyl)propylamino | 2,5-dihydroxy-4-methoxybenzylamino | Isopropyl | C = 55.54%; H = 6.85%; N = 28.79% | 430.2 | |
| 3-aminopropylamino | 2,5-dihydroxy-4-methoxybenzylamino | Isopropyl | C = 53.48%; H = 6.70%; N = 27.92% | 401.2 | |

TABLE 2-continued

Compounds Prepared by the Method of Examples 7–13

| 8-AZAPURINE SUBSTITUENT | | | ANALYSES | | |
|---|---|---|---|---|---|
| C2 | C6 | | CHNO | MS [M − H]+ | MS [M + H]− |
| 2-aminoethylamino | 2,5-dihydroxy-4-methoxybenzylamino | Isopropyl | C = 52.81%; H = 6.08%; N = 28.72% | 387.2 | |
| 2-hydroxyethylamino | 2,6-dihydroxy-4-methoxybenzylamino | Isopropyl | C = 52.39%; H = 6.06%; N = 25.10% | 388.2 | |
| 3-hydroxypropylamino | 2,6-dihydroxy-4-methoxybenzylamino | Isopropyl | C = 53.72%; H = 6.12%; N = 24.35% | 402.2 | |
| Bis-(2-hydroxyethyl)amino | 2,6-dihydroxy-4-methoxybenzylamino | Isopropyl | C = 52.81%; H = 6.12%; N = 22.75% | 432.2 | |
| 2-aminocyclohexylamino | 2,6-dihydroxy-4-methoxybenzylamino | Isopropyl | C = 57.24%; H = 6.71%; N = 25.25% | 441.2 | |
| 4-aminocyclohexylamino | 2,6-dihydroxy-4-methoxybenzylamino | Isopropyl | C = 57.16%; H = 6.77%; N = 25.20% | 441.2 | |
| R-(1-hydroxymethyl)propylamino | 2,6-dihydroxy-4-methoxybenzylamino | Isopropyl | C = 54.42%; H = 6.68%; N = 23.50% | 416.2 | |
| R-(1-hydroxymethyl-2-methyl)propylamino | 2,6-dihydroxy-4-methoxybenzylamino | Isopropyl | C = 55.50%; H = 6.82%; N = 22.80% | 430.2 | |
| 3-aminopropylamino | 2,6-dihydroxy-4-methoxybenzylamino | Isopropyl | C = 53.99%; H = 6.42%; N = 27.71% | 401.2 | |
| 2-aminoethylamino | 2,6-dihydroxy-4-methoxybenzylamino | Isopropyl | C = 52.30%; H = 6.55%; N = 28.75% | 387.2 | |
| 2-hydroxyethylamino | 4-chloro-2,3-dihydroxybenzylamino | Isopropyl | C = 48.61%; H = 5.35%; N = 25.00%; Cl = 8.77% | 392.1 394.2 | |
| 3-hydroxypropylamino | 4-chloro-2,3-dihydroxybenzylamino | Isopropyl | C = 50.31%; H = 5.26%; N = 23.91%; Cl = 8.76% | 406.1 408.2 | |
| Bis-(2-hydroxyethyl)amino | 4-chloro-2,3-dihydroxybenzylamino | Isopropyl | C = 49.49%; H = 5.33%; N = 22.29%; Cl = 8.25% | 436.2 438.2 | |
| 2-aminocyclohexylamino | 4-chloro-2,3-dihydroxybenzylamino | Isopropyl | C = 53.47%; H = 6.25%; N = 24.95%; Cl = 8.20% | 445.2 447.2 | |
| 4-aminocyclohexylamino | 4-chloro-2,3-dihydroxybenzylamino | Isopropyl | C = 53.66%; H = 6.19%; N = 24.90%; Cl = 8.15% | 445.2 447.2 | |
| R-(1-hydroxymethyl)propylamino | 4-chloro-2,3-dihydroxybenzylamino | Isopropyl | C = 51.42%; H = 5.66%; N = 23.10%; Cl = 8.55% | 420.2 422.2 | |
| R-(1-hydroxymethyl-2-methyl)propylamino | 4-chloro-2,3-dihydroxybenzylamino | Isopropyl | C = 52.76%; H = 5.92%; N = 22.35%; Cl = 8.25% | 434.2 436.2 | |
| 3-aminopropylamino | 4-chloro-2,3-dihydroxybenzylamino | Isopropyl | C = 50.32%; H = 5.61%; N = 27.65%; Cl = 8.60% | 405.2 407.2 | |
| 2-aminoethylamino | 4-chloro-2,3-dihydroxybenzylamino | Isopropyl | C = 48.70%; H = 5.52%; N = 28.41%; Cl = 9.17% | 391.1 393.1 | |
| 2-hydroxyethylamino | 4-chloro-2,5-dihydroxybenzylamino | Isopropyl | C = 48.96%; H = 5.02%; N = 25.12%; Cl = 8.81% | 392.1 394.1 | |
| 3-hydroxypropylamino | 4-chloro-2,5-dihydroxybenzylamino | Isopropyl | C = 50.24%; H = 5.13%; N = 24.31%; Cl = 8.52% | 406.1 408.1 | |
| Bis-(2-hydroxyethyl)amino | 4-chloro-2,5-dihydroxybenzylamino | Isopropyl | C = 49.66%; H = 5.34%; N = 22.69%; Cl = 7.82% | 436.2 438.2 | |
| 2-aminocyclohexylamino | 4-chloro-2,5-dihydroxybenzylamino | Isopropyl | C = 53.46%; H = 6.26%; N = 25.21%; Cl = 7.85% | 445.2 447.2 | |
| 4-aminocyclohexylamino | 4-chloro-2,5-dihydroxybenzylamino | Isopropyl | C = 53.52%; H = 6.31%; N = 25.30%; Cl = 7.73% | 445.2 447.2 | |
| R-(1-hydroxymethyl)propylamino | 4-chloro-2,5-dihydroxybenzylamino | Isopropyl | C = 51.39%; H = 5.84%; N = 23.52%; Cl = 8.15% | 420.2 422.2 | |
| R-(1-hydroxymethyl-2-methyl)propylamino | 4-chloro-2,5-dihydroxybenzylamino | Isopropyl | C = 52.35%; H = 6.29%; N = 22.12%; Cl = 8.26% | 434.2 436.2 | |
| 3-aminopropylamino | 4-chloro-2,5-dihydroxybenzylamino | Isopropyl | C = 50.02%; H = 5.84%; N = 27.71%; Cl = 8.62% | 405.2 407.2 | |
| 2-aminoethylamino | 4-chloro-2,5-dihydroxybenzylamino | Isopropyl | C = 49.21%; H = 5.12%; N = 28.46%; Cl = 9.15% | 391.1 393.1 | |
| 2-hydroxyethylamino | 2-amino-6-chlorobenzylamine | Isopropyl | C = 51.25%; H = 5.48%; N = 29.60%; Cl = 9.35% | 375.1 377.1 | |
| 3-hydroxypropylamino | 2-amino-6-chlorobenzylamine | Isopropyl | C = 52.35%; H = 5.72%; N = 28.70%; Cl = 9.16% | 389.2 391.2 | |
| Bis-(2-hydroxyethyl)amino | 2-amino-6-chlorobenzylamine | Isopropyl | C = 51.21%; H = 6.03%; N = 26.50%; Cl = 8.57% | 419.2 421.2 | |
| 2-aminocyclohexylamino | 2-amino-6-chlorobenzylamine | Isopropyl | C = 55.98%; H = 6.42%; N = 29.46%; Cl = 8.14% | | 430.2 432.2 |
| 4-aminocyclohexylamino | 2-amino-6-chlorobenzylamine | Isopropyl | C = 55.92%; H = 6.48%; N = 29.40%; Cl = 8.20% | | 430.2 432.2 |
| R-(1-hydroxymethyl)propylamino | 2-amino-6-chlorobenzylamine | Isopropyl | C = 53.52%; H = 6.14%; N = 27.59%; Cl = 8.90% | 403.2 405.2 | |
| R-(1-hydroxymethyl-2-methyl)propylamino | 2-amino-6-chlorobenzylamine | Isopropyl | C = 54.32%; H = 6.66%; N = 26.63%; Cl = 8.59% | 417.2 419.2 | |
| 3-aminopropylamino | 2-amino-6-chlorobenzylamine | Isopropyl | C = 52.46%; H = 6.36%; N = 32.03%; Cl = 9.15% | | 390.2 392.2 |

TABLE 2-continued

Compounds Prepared by the Method of Examples 7–13

| 8-AZAPURINE SUBSTITUENT | | | ANALYSES | | |
| --- | --- | --- | --- | --- | --- |
| C2 | C6 | | CHNO | MS [M − H]⁺ | MS [M + H]⁻ |
| 2-aminoethylamino | 2-amino-6-chlorobenzylamine | Isopropyl | C = 52.27%; H = 5.84%; N = 33.62%; Cl = 9.27% | | 376.2 378.2 |
| 2-hydroxyethylamino | 3-amino-4-chlorobenzylamine | Isopropyl | C = 51.15%; H = 5.52%; N = 29.63%; Cl = 9.56% | 375.1 377.1 | |
| 3-hydroxypropylamino | 3-amino-4-chlorobenzylamine | Isopropyl | C = 52.09%; H = 6.05%; N = 28.60%; Cl = 9.24% | 389.2 391.2 | |
| Bis-(2-hydroxyethyl)amino | 3-amino-4-chlorobenzylamine | Isopropyl | C = 51.48%; H = 5.72%; N = 26.59%; Cl = 8.66% | 419.2 421.2 | |
| 2-aminocyclohexylamino | 3-amino-4-chlorobenzylamine | Isopropyl | C = 55.98%; H = 6.42%; N = 29.48%; Cl = 8.12% | | 430.2 432.2 |
| 4-aminocyclohexylamino | 3-amino-4-chlorobenzylamine | Isopropyl | C = 55.65%; H = 6.70%; N = 29.45%; Cl = 8.20% | | 430.2 432.2 |
| R-(1-hydroxymethyl)propylamino | 3-amino-4-chlorobenzylamine | Isopropyl | C = 53.21%; H = 6.35%; N = 27.59%; Cl = 8.88% | | 405.2 407.2 |
| R-(1-hydroxymethyl-2-methyl)propylamino | 3-amino-4-chlorobenzylamine | Isopropyl | C = 54.59%; H = 6.62%; N = 26.55%; Cl = 8.62% | | 419.2 421.2 |
| 3-aminopropylamino | 3-amino-4-chlorobenzylamine | Isopropyl | C = 52.44%; H = 6.06%; N = 32.29%; Cl = 9.21% | | 390.2 392.2 |
| 2-aminoethylamino | 3-amino-4-chlorobenzylamine | Isopropyl | C = 51.34%; H = 5.82%; N = 33.29%; Cl = 9.54% | | 376.2 378.2 |
| 2-hydroxyethylamino | 4-chloro-2,3-diaminobenzylamine | Isopropyl | C = 49.16%; H = 5.48%; N = 31.95%; Cl = 9.16% | | 392.2 394.2 |
| 3-hydroxypropylamino | 4-chloro-2,3-diaminobenzylamine | Isopropyl | C = 50.21%; H = 6.05%; N = 30.89%; Cl = 8.89% | | 406.2 408.2 |
| Bis-(2-hydroxyethyl)amino | 4-chloro-2,3-diaminobenzylamine | Isopropyl | C = 49.87%; H = 5.88%; N = 28.74%; Cl = 8.14% | | 436.2 438.2 |
| 2-aminocyclohexylamino | 4-chloro-2,3-diaminobenzylamine | Isopropyl | C = 54.15%; H = 6.41%; N = 31.66%; Cl = 7.78% | | 445.2 447.2 |
| 4-aminocyclohexylamino | 4-chloro-2,3-diaminobenzylamine | Isopropyl | C = 54.24%; H = 6.46%; N = 31.54%; Cl = 7.76% | | 445.2 447.2 |
| R-(1-hydroxymethyl)propylamino | 4-chloro-2,3-diaminobenzylamine | Isopropyl | C = 51.30%; H = 6.33%; N = 30.10%; Cl = 8.41% | 418.2 420.2 | |
| R-(1-hydroxymethyl-2-methyl)propylamino | 4-chloro-2,3-diaminobenzylamine | Isopropyl | C = 52.71%; H = 6.38%; N = 28.92%; Cl = 8.25% | 432.2 434.2 | |
| 3-aminopropylamino | 4-chloro-2,3-diaminobenzylamine | Isopropyl | C = 50.21%; H = 6.19%; N = 34.66%; Cl = 8.94% | | 405.2 407.2 |
| 2-aminoethylamino | 4-chloro-2,3-diaminobenzylamine | Isopropyl | C = 49.02%; H = 6.11%; N = 35.75%; Cl = 9.12% | | 391.2 |
| 2-hydroxyethylamino | [(R,S)-(2-hydroxy-1-phenyl-ethyl)amino] | Isopropyl | C = 57.32%; H = 6.29%; N = 27.39% | 356.2 | |
| 3-hydroxypropylamino | [(R,S)-(2-hydroxy-1-phenyl-ethyl)amino] | Isopropyl | C = 58.49%; H = 6.65%; N = 26.31% | 370.2 | |
| Bis-(2-hydroxyethyl)amino | [(R,S)-(2-hydroxy-1-phenyl-ethyl)amino] | Isopropyl | C = 56.71%; H = 6.89%; N = 24.46% | 400.2 | |
| 2-aminocyclohexylamino | [(R,S)-(2-hydroxy-1-phenyl-ethyl)amino] | Isopropyl | C = 61.29%; H = 7.51%; N = 27.33% | | 411.3 |
| 4-aminocyclohexylamino | [(R,S)-(2-hydroxy-1-phenyl-ethyl)amino] | Isopropyl | C = 61.34%; H = 7.48%; N = 27.26% | | 411.3 |
| R-(1-hydroxymethyl)propylamino | [(R,S)-(2-hydroxy-1-phenyl-ethyl)amino] | Isopropyl | C = 59.36%; H = 6.95%; N = 25.37% | 384.2 | |
| R-(1-hydroxymethyl-2-methyl)propylamino | [(R,S)-(2-hydroxy-1-phenyl-ethyl)amino] | Isopropyl | C = 60.25%; H = 7.12%; N = 24.58% | 398.2 | |
| 3-aminopropylamino | [(R,S)-(2-hydroxy-1-phenyl-ethyl)amino] | Isopropyl | C = 58.61%; H = 6.85%; N = 30.20% | | 371.2 |
| 2-aminoethylamino | [(R,S)-(2-hydroxy-1-phenyl-ethyl)amino] | Isopropyl | C = 57.05%; H = 6.91%; N = 31.50% | | 357.2 |
| 2-hydroxyethylamino | [N-(3,4-dihydroxybenzyl-N-methyl]amino | Isopropyl | C = 54.91%; H = 6.04%; N = 26.19% | 372.2 | |
| 3-hydroxypropylamino | [N-(3,4-dihydroxybenzyl-N-methyl]amino | Isopropyl | C = 55.98%; H = 6.39%; N = 25.21% | 386.2 | |
| Bis-(2-hydroxyethyl)amino | [N-(3,4-dihydroxybenzyl-N-methyl]amino | Isopropyl | C = 54.91%; H = 6.32%; N = 23.40% | 416.2 | |
| 2-aminocyclohexylamino | [N-(3,4-dihydroxybenzyl-N-methyl]amino | Isopropyl | C = 59.36%; H = 6.91%; N = 26.21% | 425.2 | |
| 4-aminocyclohexylamino | [N-(3,4-dihydroxybenzyl-N-methyl]amino | Isopropyl | C = 59.41%; H = 6.86%; N = 26.20% | 425.2 | |

TABLE 2-continued

Compounds Prepared by the Method of Examples 7–13

| 8-AZAPURINE SUBSTITUENT | | | ANALYSES | | |
|---|---|---|---|---|---|
| C2 | C6 | | CHNO | MS [M − H]+ | MS [M + H]− |
| R-(1-hydroxymethyl)propylamino | [N-(3,4-dihydroxybenzyl-N-methyl]amino | Isopropyl | C = 56.57%; H = 6.94%; N = 24.51% | 400.2 | |
| R-(1-hydroxymethyl-2-methyl)propylamino | [N-(3,4-dihydroxybenzyl-N-methyl]amino | Isopropyl | C = 57.73%; H = 7.15%; N = 23.54% | 414.2 | |
| 3-aminopropylamino | [N-(3,4-dihydroxybenzyl-N-methyl]amino | Isopropyl | C = 55.69%; H = 6.91%; N = 29.05% | 385.2 | |
| 2-aminoethylamino | [N-(3,4-dihydroxybenzyl-N-methyl]amino | Isopropyl | C = 54.98%; H = 6.41%; N = 30.01% | 371.2 | |

TABLE 3

Compounds Prepared by the Method of Example 14 and 15

| 8-AZAPURINE SUBSTITUENT | | | ANALYSES | | |
|---|---|---|---|---|---|
| C2 | C6 | N9 | CHNO | MS [M − H]+ | MS [M + H]+ |
| Methyl | Beozylamino | Isopropyl | C = 63.41%; H = 6.59%; N = 30.00% | 281.2 | |
| Methyl | 3,4-dihydroxybenzylamino | Isopropyl | C = 57.55%; H = 5.62%; N = 26.66% | 313.1 | |
| Methyl | 3-chloroanilino | Isopropyl | C = 55.80%; H = 4.75%; N = 27.63%; Cl = 11.82% | 301.1 303.1 | |
| Methyl | anilino | Isopropyl | C = 62.41%; H = 6.20%; N = 31.39% | 267.1 | |
| Methyl | 4-carboxy-3-chloroanilino | Isopropyl | C = 51.74%; H = 4.52%; N = 24.31%; Cl = 10.10% | 345.1 347.1 | |
| Methyl | 3-carboxy-4-chloroanilino | Isopropyl | C = 51.85%; H = 4.48%; N = 24.35%; Cl = 10.15% | 345.1 347.1 | |
| Methyl | 3-carboxy-4-hydroxyanilino | Isopropyl | C = 54.59%; H = 5.04%; N = 25.70% | 327.1 | |
| Methyl | 4-bromoanilino | Isopropyl | C = 48.19%; H = 4.47%; N = 24.19%; Br = 23.15% | 345.0 347.0 | |
| Methyl | 4-chloroanilino | Isopropyl | C = 55.75%; H = 4.81%; N = 27.80%; Cl = 11.64% | 301.0 303.0 | |
| Methyl | 3-amino-4-chloroanilino | Isopropyl | C = 52.81%; H = 5.25%; N = 30.89%; Cl = 11.05% | 316.1 318.1 | |
| Methyl | 4-amino-3-chloroanilino | Isopropyl | C = 52.77%; H = 5.02%; N = 31.00%; Cl = 11.21% | 316.1 318.1 | |
| Methyl | 5-amino-3-chloroanilino | Isopropyl | C = 53.12%; H = 4.85%; N = 30.77%; Cl = 11.26% | 316.1 318.1 | |
| Methyl | 2-hydroxybenzylamino | Isopropyl | C = 59.35%; H = 5.51%; N = 29.50% | 283.1 | |
| Methyl | 3-hydroxybenzylamino | Isopropyl | C = 59.26%; H = 5.48%; N = 29.65% | 283.1 | |
| Methyl | 2-acetoxybenzylamino | Isopropyl | C = 58.98%; H = 5.41%; N = 25.78% | 325.1 | |
| Methyl | 3-acetoxybenzylamino | Isopropyl | C = 58.71%; H = 5.62%; N = 25.89% | 325.1 | |
| Methyl | 2-acetylbenzylamino | Isopropyl | C = 61.66%; H = 6.04%; N = 27.12% | 309.1 | |
| Methyl | 3-acetylbenzylamino | Isopropyl | C = 61.75%; H = 5.98%; N = 27.16% | 309.1 | |
| Methyl | 2-hydroxy-3-methoxybenzylamino | Isopropyl | C = 58.79%; H = 6.02%; N = 25.49% | 327.1 | |
| Methyl | 2-hydroxy-3-methylbenzylamino | Isopropyl | C = 61.35%; H = 6.61%; N = 26.95% | 311.2 | |
| Methyl | 3-chloro-2-hydroxybenzylamino | Isopropyl | C = 54.33%; H = 5.23%; N = 25.35%; Cl = 10.31% | 331.1 333.1 | |
| Methyl | 2,3-dihydroxy-4-methoxybenzylamino | Isopropyl | C = 55.54%; H = 6.06%; N = 24.49% | 343.2 | |
| Methyl | 2,5-dihydroxy-4-methoxybenzylamino | Isopropyl | C = 55.71%; H = 5.99%; N = 24.30% | 343.2 | |
| Methyl | 2,6-dihydroxy-4-methoxybenzylamino | Isopropyl | C = 55.92%; H = 5.70%; N = 24.46% | 343.2 | |

TABLE 3-continued

Compounds Prepared by the Method of Example 14 and 15

| 8-AZAPURINE SUBSTITUENT | | | ANALYSES | | |
|---|---|---|---|---|---|
| C2 | C6 | N9 | CHNO | MS [M − H]+ | MS [M + H]+ |
| Methyl | 2,3-dihydroxy-4-chlorobenzylamino | Isopropyl | C = 51.84%; H = 4.75%; N = 24.21%; Cl = 10.05% | 347.1 349.1 | |
| Methyl | 4-chloro-2,5-dihydroxybenzylamino | Isopropyl | C = 51.92%; H = 4.79%; N = 23.95%; Cl = 10.11% | 347.1 349.1 | |
| Methyl | 4-chloro-2,6-dihydroxybenzylamino | Isopropyl | C = 51.85%; H = 4.77%; N = 24.15%; Cl = 10.10% | 347.1 349.1 | |
| Methyl | 2-amino-6-chlorobenzylamine | Isopropyl | C = 54.55%; H = 5.21%; N = 29.69%; Cl = 10.55% | 330.1 332.1 | |
| Methyl | 3-amino-4-chlorobenzylamine | Isopropyl | C = 54.49%; H = 5.23%; N = 29.75%; Cl = 10.49% | 330.1 332.1 | |
| Methyl | 4-chloro-2,3-diaminobenzylamine | Isopropyl | C = 52.16%; H = 5.33%; N = 32.35%; Cl = 10.16% | | 347.1 349.1 |
| Methyl | [(R,S)-(2-hydroxy-1-phenylethyl)amino] | Isopropyl | C = 61.29%; H = 6.62%; N = 26.99% | 311.2 | |
| Methyl | [N-(3,4-dihydroxybenzyl-N-methyl]amino | Isopropyl | C = 58.35%; H = 5.07%; N = 25.73% | 327.2 | |

TABLE 4

Compounds Prepared by the Method of Examples 14–21

| 8-AZAPURINE SUBSTITUENT | | ANALYSES | | |
|---|---|---|---|---|
| C2 | C6 | CHNO | MS [M − H]+ | MS [M + H]+ |
| 2-hydroxyethylamino | benzylamino | C = 54.38%; H = 5.39%; N = 34.51% | 284.1 | |
| 3-hydroxypropylamino | benzylamino | C = 56.02%; H = 5.69%, N = 32.88% | 298.1 | |
| 2-aminocyclohexylamino | benzylamino | C = 60.51%; H = 6.29%; N = 33.20% | | 339.3 |
| 4-aminocyclohexylamino | benzylamino | C = 60.65%; H = 6.19%; N = 33.16% | | 339.3 |
| R-(1-hydroxymethyl)propylamino | benzylamino | C = 57.61% H = 6.24%; N = 31.02% | 312.1 | |
| R-(1-hydroxymethyl-2-methyl)propylamino | benzylamino | C = 58.55%; H = 6.25%; N = 30.24% | 326.1 | |
| 3-aminopropylamino | benzylamino | C = 56.65%; H = 5.85%; N = 37.50% | | 299.2 |
| 2-hydroxyethylamino | 3-chloroanilino | C = 47.42%; H = 3.85%; N = 32.15%; Cl = 11.42% | 304.1 306.1 | |
| 3-hydroxypropylamino | 3-chloroanilino | C = 48.95%; H = 4.68%; N = 30.55%; Cl = 10.95% | 318.1 320.1 | |
| 2-aminocyclohexylamino | 3-chloroanilino | C = 53.91%, H = 5.15%; N = 31.02%; Cl = 9.92% | 357.2 359.2 | |
| 4-aminocyclohexylamino | 3-chloroanilino | C = 53.81%; H = 5.20%; N = 31.43%; Cl = 9.56% | 357.2 359.2 | |
| R-(1-hydroxymethyl)propylamino | 3-chloroanilino | C = 50.15%; H = 4.71%; N = 29.65%; Cl = 10.51% | 332.1 334.1 | |
| R-(1-hydroxymethyl-2-methyl)propylamino | 3-chloroanilino | C = 51.66%; H = 5.00%; N = 28.54%; Cl = 10.25% | 346.1 348.1 | |
| 3-aminopropylamino | 3-chloroanilino | C = 49.35%; H = 4.38%; N = 35.26%; Cl = 11.01% | 317.2 319.2 | |
| 2-aminoethylamino | 3-chloroanilino | C = 47.49%; H = 4.44%; N = 36.54%; Cl = 11.53% | 303.1 305.1 | |
| 3-hydroxypropylamino | 4-carboxy-3-chloroanilino | C = 46.56%; H = 3.75%; N = 29.74%; Cl = 9.83 | 362.2 364.2 | |
| 2-aminocyclohexylamino | 4-carboxy-3-chloroanilino | C = 50.27%; H = 4.94%; N = 27.66%; Cl = 8.99% | 401.2 403.2 | |
| 4-aminocyclohexylamino | 4-carboxy-3-chloroanilino | C = 50.45%; H = 4.89%; N = 27.46%; Cl = 8.95% | 401.2 403.2 | |
| R-(1-hydroxymethyl)propylamino | 4-carboxy-3-chloroanilino | C = 47.79%; H = 4.45%; N = 25.74%; Cl = 9.15% | 376.1 378.1 | |
| R-(1-hydroxymethyl-2-methyl)propylamino | 4-carboxy-3-chloroanilino | C = 49.33%; H = 4.64%; N = 25.27%; Cl = 8.95% | 390.1 392.1 | |
| 3-aminopropylamino | 4-carboxy-3-chloroanilino | C = 46.12%; H = 4.00%; N = 31.15%; Cl = 9.96% | 361.0 363.0 | |

TABLE 4-continued

Compounds Prepared by the Method of Examples 14–21

| 8-AZAPURINE SUBSTITUENT | | ANALYSES | | |
|---|---|---|---|---|
| C2 | C6 | CHNO | MS [M − H]+ | MS [M + H]+ |
| 3-hydroxypropylamino | 3-carboxy-4-chloroanilino | C = 46.53%; H = 3.65%; N = 29.70%; Cl = 9.94% | 362.2 364.2 | |
| 2-aminocyclohexylamino | 3-carboxy-4-chloroanilino | C = 50.49%; H = 4.60%; N = 27.94%; Cl = 8.99% | 401.2 403.2 | |
| 4-aminocyclohexylamino | 3-carboxy-4-chloroanilino | C = 50.36%; H = 4.70%; N = 28.05%; Cl = 8.02% | 401.2 403.2 | |
| R-(1-hydroxymethyl)propylamino | 3-Carbox-4-chloroanilino | C = 47.85%; H = 4.15%; N = 25.84%; Cl = 9.25% | 376.0 378.0 | |
| R-(1-hydroxymethyl-2-methyl)propylamino | 3-carboxy-4-chloroanilino | C = 49.45% H = 4.49%; N = 25.19%; Cl = 8.84% | 390.2 392.2 | |
| 3-aminopropylamino | 3-carboxy-4-chloroanilino | C = 46.60%; H = 4.09%; N = 30.94%; Cl = 9.44% | 361.0 363.0 | |
| 4-aminocyclohexylamino | 4-bromoanilino | C = 47.44%; H = 4.89%; N = 27.51%; Br = 20.16% | | 403.1 405.1 |
| R-(1-hydroxymethyl)propylamino | 4-bromoanilino | C = 44.59%; H = 4.02%; N = 25.80%; Br = 21.15% | 376.1 378.1 | |
| R-(1-hydroxymethyl-2-methyl)propylamino | 4-bromoanilino | C = 45.59%; H = 4.81%; N = 25.14%; Br = 20.49% | 390.1 392.1 | |
| 3-aminopropylamino | 4-bromoanilino | C = 42.79%; H = 4.09%; N = 31.19%; Br = 21.93% | | 363.1 365.1 |
| 2-aminocyclohexylamino | 4-chloroanilino | C = 53.44%; H = 5.49%; N = 31.00%; Cl = 10.07% | 357.2 359.2 | |
| R-(1-hydroxymethyl)propylamino | 4-chloroanilino | C = 50.65%; H = 4.70%; N = 29.44%; Cl = 10.27% | 332.1 334.1 | |
| R-(1-hydroxymethyl-2-methyl)propylamino | 4-chloroanilino | C = 51.99%; H = 5.40%; N = 27.99%; Cl = 9.99% | 346.1 348.1 | |
| 2-aminocyclohexylamino | 2-hydroxybenzylamino | C = 57.45%; H = 6.09%; N = 31.88% | | 355.2 |
| 4-aminocyclohexylamino | 2-hydroxybenzylamino | C = 57.75%; H = 6.39%; N = 31.43% | | 355.2 |
| R-(1-hydroxymethyl)propylamino | 2-hydroxybenzylamino | C = 54.95%; H = 5.71%; N = 29.70% | 330.1 | |
| R-(1-hydroxymethyl-2-methyl)propylamino | 2-hydroxybenzylamino | C = 55.80%; H = 6.25%; N = 28.70% | 342.2 | |
| 3-aminopropylamino | 2-hydroxybenzylamino | C = 53.71%; H = 5.62%; N = 35.44% | | 313.1 |
| 2-aminocyclohexylamino | 2-hydroxy-3-methoxybenzylamino | C = 56.60%; H = 6.10%; N = 29.00% | | 385.2 |
| 4-aminocyclohexylamino | 2-hydroxy-3-methoxybenzylamino | C = 56.39%; H = 6.14%; N = 28.99% | | 385.2 |
| R-(1-hydroxymethyl)propylamino | 2-hydroxy-3-methoxybenzylamino | C = 53.71%; H = 5.78%; N = 27.44% | 358.2 | |
| R-(1-hydroxymethyl-2-methyl)propylamino | 2-hydroxy-3-methoxybenzylamino | C = 54.41%; H = 6.46%; N = 26.30% | 372.2 | |
| 2-aminocyclohexylamino | 2-amino-6-chlorobenzylamine | C = 52.44%; H = 5.91%; N = 32.40%; Cl = 9.25% | | 388.2 390.2 |
| 4-aminocyclohexylamino | 2-amino-6-chlorobenzylamine | C = 52.77%; H = 5.51%; N = 32.46%; Cl = 9.26% | | 388.2 390.2 |
| R-(1-hydroxymethyl)propylamino | 2-amino-6-chlorobenzylamine | C = 49.80%; H = 5.41%; N = 30.65%; Cl = 9.41% | 361.1 363.1 | |
| R-(1-hydroxymethyl-2-methyl)propylamino | 2-amino-6-chlorobenzylamine | C = 50.85%; H = 5.79%; N = 29.39%; Cl = 9.41% | 375.2 377.2 | |
| 3-aminopropylamino | 2-amino-6-chlorobenzylamine | C = 48.61%; H = 5.00%; N = 36.39%; Cl = 10.00% | | 348.2 350.2 |
| 3-nitrobenzylamino | benzylamino | C = 57.66%; H = 4.28%; N = 29.55% | 375.2 | 377.3 |
| 4-nitrobenzylamino | benzylamino | C = 57.40%; H = 4.32%; N = 29.72% | 375.2 | 377.3 |
| 3-aminobenzylamino | benzylamino | C = 62.31%; H = 5.44%; N = 32.25% | 345.1 | 347.3 |
| 4-aminobenzylamino | benzylamino | C = 62.29%; H = 5.46%; N = 32.25% | 345.1 | 347.3 |
| 3-sulfamoylfenylamino | benzylamino | C = 51.31%; H = 4.11%; N = 28.19% | 395.2 | 397.3 |
| 4-sulfamoylfenylamino | benzylamino | C = 51.52%; H = 4.32%; N = 28.20% | 395.2 | 397.3 |
| 3-sulfamoylbenzylamino | benzylamino | C = 52.69%; H = 4.40%; N = 27.33% | 409.1 | 411.4 |
| 4-sulamoylbenzylamino | benzylamino | C = 52.56%; H = 4.69%; N = 27.42% | 409.1 | 411.4 |

TABLE 4-continued

Compounds Prepared by the Method of Examples 14–21

| 8-AZAPURINE SUBSTITUENT | | ANALYSES | | |
|---|---|---|---|---|
| | | | MS | MS |
| C2 | C6 | CHNO | [M − H]⁺ | [M + H]⁺ |
| 3-ureidopropylamino | benzylamino | C = 52.83%; H = 5.74%; N = 36.71% | 340.2 | 342.4 |
| 2-ureidoethylamino | benzylamino | C = 51.07%; H = 5.33%; N = 38.48% | 326.0 | 328.0 |
| 3-guanidinopropylamino | benzylamino | C = 52.72%; H = 6.13%; N = 41.15% | 339.0 | 341.0 |
| 2-guanidinoethylamino | benzylamino | C = 51.50%; H = 5.78%; N = 42.72% | 325.0 | 327.1 |
| benzylamino | 3-nitrobenzylamino | C = 57.06%; H = 4.43%; N = 29.60% | 375.0 | 377.0 |
| benzylamino | 4-nitrobenzylamino | C = 57.11%; H = 4.31%; N = 29.58% | 375.0 | 377.0 |
| benzylamino | 3-aminobenzylamino | C = 62.11%; H = 5.54%; N = 32.35% | 345.1 | 347.3 |
| benzylamino | 4-aminobenzylamino | C = 62.22%; H = 5.52%; N = 32.26% | 345.1 | 347.3 |
| benzylamino | 3-sulfamoylfenylamino | C = 51.63%, H = 4.40%, N = 28.00% | 395.1 | 397.2 |
| benzylamino | 4-sulfamoylfenylamino | C = 51.40%, H = 4.10% N = 28.00% | 395.1 | 397.2 |
| benzylamino | 3-sulfamoylbenzylamino | C = 52.57%, H = 4.62% N = 27.11% | 409.1 | 411.1 |
| benzylamino | 4-sulfamoylbenzylamino | C = 52.44%, H = 4.67%, N = 27.23% | 409.2 | 411.3 |
| benzylamino | 3-ureidopropylamino | C = 52.70%, H = 5.68%, N = 36.63% | 340.0 | 342.2 |
| benzylamino | 2-ureidoethylamino | C = 51.30%, H = 5.23%, N = 38.41% | 326.1 | 328.1 |
| benzylamino | 3-guanidinopropylamino | C = 52.80%, H = 6.02%, N = 41.18% | 339.2 | 341.4 |
| benzylamino | 2-guanidinoethylamino | C = 51.44%; H = 5.86%; N = 42.80% | 325.3 | 327.3 |

TABLE 5

Kinase Inhibitory Activity of Selected 2,6,9-Trisubstituted 8-Azapurine Derivatives

| SUBSTITUENT | | | CDC2 | IκB-α |
|---|---|---|---|---|
| C2 | C6 | N9 | IC₅₀ (μM) | IC₅₀ (μM) |
| 2-hydroxyethylamino | benzylamino | methyl | >100 | >100 |
| 3-hydroxypropylamino | benzylamino | methyl | >100 | >100 |
| Bis-(2-hydroxyethyl)amino | benzylamino | methyl | 100 | >100 |
| 2-aminocyclohexylamino | benzylamino | methyl | 25 | 70 |
| 4-aminocyclohexylamino | benzylamino | methyl | 16 | 40 |
| R-(1-hydroxymethyl)propylamino | benzylamino | methyl | 100 | >100 |
| R-(1-hydroxymethyl-2-methyl)propylamino | benzylamino | methyl | 50 | >100 |
| 3-aminopropylamino | benzylamino | methyl | 90 | >100 |
| 2-aminoethylamino | benzylamino | methyl | 90 | >100 |
| 2-hydroxyethylamino | 3,4-dihydroxybenzylamino | methyl | 100 | >100 |
| 2-hydroxyethylamino | 3-chloroanilino | methyl | 100 | >100 |
| 2-hydroxyethylamino | anilino | methyl | 42 | >100 |
| 2-hydroxyethylamino | 3-chloro-5-aminoanilino | methyl | 50 | >100 |
| 2-hydroxyethylamino | 3-chloro-4-carboxyanilino | methyl | 52 | >100 |
| 2-hydroxyethylamino | 3-carboxy-4-chloroanilino | methyl | 43 | >100 |
| 2-hydroxyethylamino | 3-carboxy-4-hydroxyanilino | methyl | 58 | >100 |
| 2-hydroxyethylamino | 4-bromoanilino | methyl | >100 | >100 |
| 2-hydroxyethylamino | 4-chloroanilino | methyl | >100 | >100 |
| 2-hydroxyethylamino | 3-amino-4-chloroanilino | methyl | >100 | >100 |
| 2-hydroxyethylamino | 3-chloro-4-aminoanilino | methyl | 100 | >100 |
| 2-hydroxyethylamino | 2-hydroxybenzylamino | methyl | 23 | 45 |
| 2-hydroxyethylamino | 3-hydroxybenzylamino | methyl | 17 | 40 |
| 2-hydroxyethylamino | 2-acetoxybenzylamino | methyl | 36 | 40 |
| 2-hydroxyethylamino | 3-acetoxybenzylamino | methyl | 48 | 50 |
| 2-hydroxyethylamino | 2-acetylbenzylamino | methyl | 70 | >100 |
| 2-hydroxyethylamino | 3-acetylbenzylamino | methyl | 80 | >100 |

TABLE 5-continued

Kinase Inhibitory Activity of Selected 2,6,9-Trisubstituted 8-Azapurine Derivatives

| SUBSTITUENT | | | CDC2 | IκB-α |
|---|---|---|---|---|
| C2 | C6 | N9 | $IC_{50}$ (μM) | $IC_{50}$ (μM) |
| 2-hydroxyethylamino | 2-hydroxy-3-methoxybenzylamino | methyl | 43 | >100 |
| 2-hydroxyethylamino | 2-hydroxy-3-methylbenzylamino | methyl | 85 | >100 |
| 2-hydroxyethylamino | 2-hydroxy-3-chlorobenzylamino | methyl | 70 | >100 |
| 2-hydroxyethylamino | 2,6-dihydroxy-4-chlorobenzylamino | methyl | 22 | >100 |
| 2-hydroxyethylamino | 2,3-dihydroxy-4-methoxybenzylamino | methyl | 20 | 90 |
| 2-hydroxyethylamino | 2,5-dihydroxy-4-methoxybenzylamino | methyl | 22 | 100 |
| 2-hydroxyethylamino | 2,6-dihydroxy-4-methoxybenzylamino | methyl | 18.2 | 100 |
| 2-hydroxyethylamino | 2,3-dihydroxy-4-chlorobenzylamino | methyl | 18.0 | 80 |
| 2-hydroxyethylamino | 2,5-dihydroxy-4-chlorobenzylamino | methyl | 31 | 75 |
| 2-hydroxyethylamino | 2-amino-6-chlorobenzylamine | methyl | 52 | 68 |
| 2-hydroxyethylamino | 3-amino-4-chlorobenzylamino | methyl | 50 | 100 |
| 2-hydroxyethylamino | 2,3-diamino-4-chlorobenzylamine | methyl | 68 | >100 |
| 2-hydroxyethylamino | [(R,S)-(1-phenyl-2-hydroxyethyl)amino] | methyl | 80 | >100 |
| 2-hydroxyethylamino | [N-(3,4-dihydroxybenzyl-N-methyl]amino | methyl | 100 | >100 |
| 2-hydroxyethylamino | benzylamino | isopropyl | >100 | >100 |
| 3-hydroxypropylamino | benzylamino | isopropyl | >100 | >100 |
| Bis-(2-hydroxyethyl)amino | benzylamino | isopropyl | 95 | >100 |
| 2-aminocyclohexylamino | benzylamino | isopropyl | 7.2 | >100 |
| 4-aminocyclohexylamino | benzylamino | isopropyl | 3.7 | 48 |
| R-(1-hydroxymethyl)propylamino | benzylamino | isopropyl | 100 | >100 |
| R-(1-hydroxymethyl-2-methyl)propylamino | benzylamino | isopropyl | 15 | 50 |
| 3-aminopropylamino | benzylamino | isopropyl | >100 | >100 |
| 2-aminoethylamino | Benzylamino | isopropyl | >100 | >100 |
| R-(1-hydroxymethyl)propylamino | 3,4-dihydroxybenzylamino | isopropyl | 40 | >100 |
| R-(1-hydroxymethyl)propylamino | 3-chloroanilino | isopropyl | 35 | 80 |
| R-(1-hydroxymethyl)propylamino | anilino | isopropyl | 29 | 70 |
| R-(1-hydroxymethyl)propylamino | 3-chloro-5-aminoanilino | isopropyl | 28 | 75 |
| R-(1-hydroxymethyl)propylamino | 3-chloro-4-carboxyanilino | isopropyl | 35 | 70 |
| R-(1-hydroxymethyl)propylamino | 3-carboxy-4-chloroanilino | isopropyl | 40 | >100 |
| R-(1-hydroxymethyl)propylamino | 3-carboxy-4-hydroxyanilino | isopropyl | 40 | >100 |
| R-(1-hydroxymethyl)propylamino | 4-bromoanilino | isopropyl | 26 | 90 |
| R-(1-hydroxymethyl)propylamino | 4-chloroanilino | isopropyl | 27 | 100 |
| R-(1-hydroxymethyl)propylamino | 3-amino-4-chloroanilino | isopropyl | 45 | >100 |
| R-(1-hydroxymethyl)propylamino | 3-chloro-4-aminoanilino | isopropyl | 50 | >100 |
| R-(1-hydroxymethyl)propylamino | 2-hydroxybenzylamino | isopropyl | 14 | 80 |
| R-(1-hydroxymethyl)propylamino | 3-hydroxybenzylamino | isopropyl | 10 | 85 |
| R-(1-hydroxymethyl)propylamino | 2-acetoxybenzylamino | isopropyl | 19 | >100 |
| R-(1-hydroxymethyl)propylamino | 3-acetoxybenzylamino | isopropyl | 24 | >100 |
| R-(1-hydroxymethyl)propylamino | 2-acetylbenzylamino | isopropyl | 37 | >100 |
| R-(1-hydroxymethyl)propylamino | 3-acetylbenzylamino | isopropyl | 58 | >100 |
| R-(1-hydroxymethyl)propylamino | 2-hydroxy-3-methoxybenzylamino | isopropyl | 15 | 75 |
| R-(1-hydroxymethyl)propylamino | 2-hydroxy-3-methylbenzylamino | isopropyl | 34 | 80 |
| R-(1-hydroxymethyl)propylamino | 2-hydroxy-3-chlorobenzylamino | isopropyl | 16 | 100 |
| R-(1-hydroxymethyl)propylamino | 2,6-dihydroxy-4-chlorobenzylamino | isopropyl | 12 | 100 |
| R-(1-hydroxymethyl)propylamino | 2,3-dihydroxy-4-methoxybenzylamino | isopropyl | 14 | >100 |
| R-(1-hydroxymethyl)propylamino | 2,5-dihydroxy-4-methoxybenzylamino | isopropyl | 12 | >100 |
| R-(1-hydroxymethyl)propylamino | 2,6-dihydroxy-4-methoxybenzylamino | isopropyl | 17 | >100 |
| R-(1-hydroxymethyl)propylamino | 2,3-dihydroxy-4-chlorobenzylamino | isopropyl | 11 | >100 |
| R-(1-hydroxymethyl)propylamino | 2,5-dihydroxy-4-chlorobenzylamino | isopropyl | 16 | >100 |
| R-(1-hydroxymethyl)propylamino | 2-amino-6-chlorobenzylamine | isopropyl | 31 | >100 |
| R-(1-hydroxymethyl)propylamino | 3-amino-4-chlorobenzylamine | isopropyl | 29 | >100 |
| R-(1-hydroxymethyl)propylamino | 2,3-diamino-4-chlorobenzylamine | isopropyl | 45 | >100 |
| R-(1-hydroxymethyl)propylamino | [(R,S)-(1-phenyl-2-hydroxyethyl)amino] | isopropyl | 100 | >100 |
| R-(1-hydroxymethyl)propylamino | [N-(3,4-dihydroxybenzyl-N-methyl]amino | isopropyl | 100 | >100 |
| R-(1-hydroxymethyl)propylamino | [N-(2-(3,4-dihydroxyfenyl)ethyl)-N-methyl]amino | isopropyl | >100 | >100 |

TABLE 5-continued

Kinase Inhibitory Activity of Selected 2,6,9-Trisubstituted 8-Azapurine Derivatives

| SUBSTITUENT | | | CDC2 | IκB-α |
|---|---|---|---|---|
| C2 | C6 | N9 | IC$_{50}$ (μM) | IC$_{50}$ (μM) |
| 2-hydroxyethylamino | 3-chloroanilino | isopropyl | 100 | >100 |
| 3-hydroxypropylamino | 3-chloroanilino | isopropyl | 100 | >100 |
| Bis-(2-hydroxyethyl)amino | 3-chloroanilino | isopropyl | 35 | >100 |
| 2-aminocyclohexylamino | 3-chloroanilino | isopropyl | 7.0 | >100 |
| 4-aminocyclohexylamino | 3-chloroanilino | isopropyl | 6.3 | 60 |
| R-(1-hydroxymethyl)propylamino | 3-chloroanilino | isopropyl | 100 | >100 |
| R-(1-hydroxymethyl-2-methyl)propylamino | 3-chloroanilino | isopropyl | 20 | 80 |
| 3-aminopropylamino | 3-chloroanilino | isopropyl | >100 | >100 |
| 2-aminoethylamino | 3-chloroanilino | isopropyl | >100 | >100 |
| R-(1-hydroxymethyl-2-methyl)propylamino | 3,4-dihydroxybenzylamino | isopropyl | 20 | >100 |
| R-(1-hydroxymethyl-2-methyl)propylamino | anilino | isopropyl | 40 | 100 |
| R-(1-hydroxymethyl-2-methyl)propylamino | 3-chloro-5-aminoanilino | isopropyl | 27 | 80 |
| R-(1-hydroxymethyl-2-methyl)propylamino | 3-chloro-4-carboxyanilino | isopropyl | 25 | 100 |
| R-(1-hydroxymethyl-2-methyl)propylamino | 3-carboxy-4-chloroanilino | isopropyl | 30 | 80 |
| R-(1-hydroxymethyl-2-methyl)propylamino | 3-carboxy-4-hydroxyanilino | isopropyl | 34 | >100 |
| R-(1-hydroxymethyl-2-methyl)propylamino | 4-bromoanilino | isopropyl | 35 | >100 |
| R-(1-hydroxymethyl-2-methyl)propylamino | 4-chloroanilino | isopropyl | 35 | 90 |
| R-(1-hydroxymethyl-2-methyl)propylamino | 3-amino-4-chloroanilino | isopropyl | 24 | 100 |
| R-(1-hydroxymethyl-2-methyl)propylamino | 3-chloro-4-aminoanilino | isopropyl | 40 | >100 |
| R-(1-hydroxymethyl-2-methyl)propylamino | 2-hydroxybenzylamino | isopropyl | 7 | >100 |
| R-(1-hydroxymethyl-2-methyl)propylamino | 3-hydroxybenzylamino | isopropyl | 8 | 80 |
| R-(1-hydroxymethyl-2-methyl)propylamino | 2-acetoxybenzylamino | isopropyl | 10 | 85 |
| R-(1-hydroxymethyl-2-methyl)propylamino | 3-acetoxybenzylamino | isopropyl | 20 | >100 |
| R-(1-hydroxymethyl-2-methyl)propylamino | 2-acetylbenzylamino | isopropyl | 25 | >100 |
| R-(1-hydroxymethyl-2-methyl)propylamino | 3-acetylbenzylamino | isopropyl | 40 | >100 |
| R-(1-hydroxymethyl-2-methyl)propylamino | 2-hydroxy-3-methoxybenzylamino | isopropyl | 55 | >100 |
| R-(1-hydroxymethyl-2-methyl)propylamino | 2-hydroxy-3-methylbenzylamino | isopropyl | 18 | 55 |
| R-(1-hydroxymethyl-2-methyl)propylamino | 2-hydroxy-3-chlorobenzylamino | isopropyl | 32 | 60 |
| R-(1-hydroxymethyl-2-methyl)propylamino | 2,6-dihydroxy-4-chlorobenzylamino | isopropyl | 18 | 100 |
| R-(1-hydroxymethyl-2-methyl)propylamino | 2,3-dihydroxy-4-methoxybenzylamino | isopropyl | 10 | 100 |
| R-(1-hydroxymethyl-2-methyl)propylamino | 2,5-dihydroxy-4-methoxybenzylamino | isopropyl | 12 | >100 |
| R-(1-hydroxymethyl-2-methyl)propylamino | 2,6-dihydroxy-4-methoxybenzylamino | isopropyl | 10 | >100 |
| R-(1-hydroxymethyl-2-methyl)propylamino | 2,3-dihydroxy-4-chlorobenzylamino | isopropyl | 11 | >100 |
| R-(1-hydroxymethyl-2-methyl)propylamino | 2,5-dihydroxy-4-chlorobenzylamino | isopropyl | 8 | >100 |
| R-(1-hydroxymethyl-2-methyl)propylamino | 2-amino-6-chlorobenzylamine | isopropyl | 10 | >100 |
| R-(1-hydroxymethyl-2-methyl)propylamino | 3-amino-4-chlorobenzylamine | isopropyl | 30 | >100 |
| R-(1-hydroxymethyl-2-methyl)propylamino | 2,3-diamino-4-chlorobenzylamine | isopropyl | 34 | >100 |
| R-(1-hydroxymethyl-2-methyl)propylamino | [(R,S)-(1-phenyl-2-hydroxyethyl)amino] | isopropyl | 50 | >100 |
| R-(1-hydroxymethyl-2-methyl)propylamino | [N-(3,4-dihydroxybenzyl-N-methyl]amino | isopropyl | 100 | >100 |
| R-(1-hydroxymethyl-2-methyl)propylamino | [N-(2-(3,4-dihydroxyfenyl)ethyl)-N-methyl]amino | isopropyl | 100 | >100 |
| | | | >100 | >100 |

TABLE 6

Kinase Inhibitory Activity of Selected 2,6,9-Trisubstituted Derivatives

| SUBSTITUENT | | | Cdc2a | MMK1 |
|---|---|---|---|---|
| C2 | C6 | C9 | IC$_{50}$ (μM) | IC$_{50}$ (μM) |
| 2-aminocyclohexylamino | 3-chloroanilino | isopropyl | 7.5 | 30 |
| 4-aminocyclohexylamino | 3-chloroanilino | isopropyl | 3.7 | 25 |
| R-(1-hydroxymethyl)propylamino | 3-chloroanilino | isopropyl | 28 | 60 |
| R-(1-hydroxymethyl-2-methyl)propylamino | 3-chloroanilino | isopropyl | 18 | 80 |
| 3-aminopropylamino | 3-chloroanilino | isopropyl | 100 | >100 |
| 2-aminoethylamino | 3-chloroanilino | isopropyl | 100 | >100 |
| R-(1-hydroxymethyl-2-methyl)propylamino | anilino | isopropyl | >100 | >100 |
| R-(1-hydroxymethyl-2-methyl)propylamino | 3-chloro-4-carboxyanilino | isopropyl | 22 | >100 |
| R-(1-hydroxymethyl-2-methyl)propylamino | 3-carboxy-4-chloroanilino | isopropyl | 26 | >100 |
| R-(1-hydroxymethyl-2-methyl)propylamino | 3-carboxy-4-hydroxyanilino | isopropyl | 30 | 100 |

TABLE 6-continued

Kinase Inhibitory Activity of Selected 2,6,9-Trisubstituted Derivatives

| SUBSTITUENT | | | Cdc2a | MMK1 |
|---|---|---|---|---|
| C2 | C6 | C9 | IC$_{50}$ (µM) | IC$_{50}$ (µM) |
| R-(1-hydroxymethyl-2-methyl)propylamino | 4-bromoanilino | isopropyl | 30 | 100 |
| R-(1-hydroxymethyl-2-methyl)propylamino | 4-chloroanilino | isopropyl | 25 | 100 |
| R-(1-hydroxymethyl-2-methyl)propylamino | 3-amino-4-chloroanilino | isopropyl | 28 | >100 |
| R-(1-hydroxymethyl-2-methyl)propylamino | 3-chloro-4-aminoanilino | isopropyl | 20 | >100 |
| R-(1-hydroxymethyl-2-methyl)propylamino | 2-acetoxybenzylamino | isopropyl | 18 | >100 |
| R-(1-hydroxymethyl-2-methyl)propylamino | 3-acetoxybenzylamino | isopropyl | 18 | >100 |
| R-(1-hydroxymethyl-2-methyl)propylamino | 3-amino-4-chlorobenzylamine | isopropyl | 25 | >100 |

TABLE 7

Modulation of the Activity of β-Adrenergic Receptors by 2,6,9-Trisubstituted 8-Azapurines

| C2 | C6 | N9 | Effect | I$_{50}$(µM) |
|---|---|---|---|---|
| Hexylamino | (R,S)-(1-phenyl-2-hydroxyethyl)amino | Isopropyl | inhibition | 12 ± 1 |
| 3-aminopropylamino | Benzylamino | Isopropyl | inhibition | 31 ± 2 |
| (1-hydroxymethyl-2-methyl)propylamino | Benzylamino | Isopropyl | inhibition | 32 ± 2 |
| (R)-(1-hydroxymethyl)propylamino | 4-hydroxybenzyl amino | Isopropyl | 1.2-fold activation | |
| (R)-(1-hydroxymethyl)propylamino | 3-hydroxybenzyl amino | Isopropyl | 1.3-fold activation | |
| 2-aminoethylamino | Benzylamino | Isopropyl | 1.1-fold activation | |
| (S)-(1-hydroxymethyl)propylamino | (R)-hydroxy-1-phenylethylamino | Isopropyl | inactive | |
| 2-hydroxypropylamino | (R)-hydroxy-1-phenylethylamino | Isopropyl | inactive | |

TABLE 8

Cytotoxicity of Novel Compounds for Different Cancer Cell Lines.

| SUBSTITUENT | | | MCF7 | K-562 |
|---|---|---|---|---|
| C2 | C6 | N9 | IC$_{50}$ (µM) | IC$_{50}$ (µM) |
| 2-hydroxyethylamino | 3-chloroanilino | isopropyl | >100 | >100 |
| 3-hydroxypropylamino | 3-chloroanilino | isopropyl | >100 | >100 |
| Bis-(2-hydroxyethyl)amino | 3-chloroanilino | isopropyl | 100 | >100 |
| 2-aminocyclohexylamino | 3-chloroanilino | isopropyl | 8.9 | 12.2 |
| 4-aminocyclohexylamino | 3-chloroanilino | isopropyl | 6.1 | 7.4 |
| R-(1-hydroxymethyl)propylamino | 3-chloroanilino | isopropyl | >100 | >100 |
| R-(1-hydroxymethyl-2-methyl)propylamino | 3-chloroanilino | isopropyl | 80 | 96 |
| 3-aminopropylamino | 3-chloroanilino | isopropyl | 100 | >100 |
| 2-aminoethylamino | 3-chloroanilino | isopropyl | 100 | >100 |
| R-(1-hydroxymethyl-2-methyl)propylamino | anilino | isopropyl | 80 | 100 |
| R-(1-hydroxymethyl-2-methyl)propylamino | 3-carboxy-4-chloroanilino | isopropyl | 21 | 42 |
| R-(1-hydroxymethyl-2-methyl)propylamino | 3-carboxy-4-hydroxyanilino | isopropyl | 24 | 28 |
| R-(1-hydroxymethyl-2-methyl)propylamino | 4-bromoanilino | isopropyl | 64 | 75 |
| R-(1-hydroxymethyl-2-methyl)propylamino | 4-chloroanilino | isopropyl | 17.6 | 19.4 |
| R-(1-hydroxymethyl-2-methyl)propylamino | 3-amino-4-chloroanilino | isopropyl | 16.4 | 18.8 |
| R-(1-hydroxymethyl-2-methyl)propylamino | 3-chloro-4-aminoanilino | isopropyl | 22.5 | 28.9 |
| R-(1-hydroxymethyl-2-methyl)propylamino | 2-hydroxybenzylamino | isopropyl | 24 | 25 |
| R-(1-hydroxymethyl-2-methyl)propylamino | 3-hydroxybenzylamino | isopropyl | 18 | 17.5 |
| R-(1-hydroxymethyl-2-methyl)propylamino | 2-acetoxybenzylamino | isopropyl | 24.1 | 24.0 |
| R-(1-hydroxymethyl-2-methyl)propylamino | 3-acetoxybenzylamino | isopropyl | 28.2 | 31.7 |
| R-(1-hydroxymethyl-2-methyl)propylamino | 2-acetylbenzylamino | isopropyl | 40.8 | 34.9 |
| R-(1-hydroxymethyl-2-methyl)propylamino | 3-acetylbenzylamino | isopropyl | 47.6 | 50.6 |

TABLE 9

Immunosupressive activity of novel derivatives

| SUBSTITUENT | | | Human lymphocytes |
|---|---|---|---|
| C2 | C6 | N9 | $ED_{50}$ (µM) |
| 2-hydroxyethylamino | benzylamino | isopropyl | 27 |
| 2-aminocyclohexylamino | benzylamino | isopropyl | 0.8 |
| 4-aminocyclohexylamino | benzylamino | isopropyl | 1.1 |
| R-(1-hydroxymethyl)propylamino | benzylamino | isopropyl | 4.5 |
| R-(1-hydroxymethyl-2-methyl)propylamino | benzylamino | isopropyl | 6.5 |
| 3-aminopropylamino | benzylamino | isopropyl | 9.8 |
| 2-aminoethylamino | benzylamino | isopropyl | 11.5 |
| 2-hydroxyethylamino | 3-chloroanilino | isopropyl | 17 |
| 3-hydroxypropylamino | 3-chloroanilino | isopropyl | 12 |
| Bis-(2-hydroxyethyl)amino | 3-chloroanilino | isopropyl | 7 |
| 2-aminocyclohexylamino | 3-chloroanilino | isopropyl | 0.2 |
| 4-aminocyclohexylamino | 3-chloroanilino | isopropyl | 0.5 |
| R-(1-hydroxymethyl)propylamino | 3-chloroanilino | isopropyl | 1.8 |
| R-(1-hydroxymethyl-2-methyl)propylamino | 3-chloroanilino | isopropyl | 3.2 |
| 3-aminopropylamino | 3-chloroanilino | isopropyl | 4.5 |
| 2-aminoethylamino | 3-chloroanilino | isopropyl | 6.7 |

TABLE 10

Cyclin-Dependent Kinase (CDK) Inhibitory Activity of Selected 2,6,9-Trisubstituted Derivatives

| Substituent | | | $IC_{50}$ (µM) | |
|---|---|---|---|---|
| C2 | C6 | N9 | CDK2 - cyclin E | CDK9 - cyclin T1 |
| (3-hydroxypropyl)amino | benzylamino | isopropyl | 54.6 | 29.2 |
| [(R)-1-(hydroxymethyl)propyl]amino | benzylamino | isopropyl | 23.2 | 11.5 |
| (4-aminocyclohexyl)amino | 3-chloroanilino | isopropyl | 3.1 | 1.1 |
| (4-aminocyclohexyl)amino | (2-hydroxybenzyl)amino | isopropyl | 27.7 | 14.7 |
| (4-hydroxycyclohexyl)amino | 3-chloroanilino | H | 0.1 | 8.0 |
| (4-aminocyclohexyl)amino | (3-hydroxybenzyl)amino | isopropyl | >10 | 1.7 |
| [(R)-1-(hydroxymethyl)propyl]amino | (3-hydroxy-4-methoxybenzyl)amino | isopropyl | 6.4 | 2.0 |
| cis-(2-aminocyclohexyl)amino | (3-hydroxy-4-methoxybenzyl)amino | isopropyl | 7.0 | 1.7 |
| (4-hydroxycyclohexyl)amino | (2-hydroxybenzyl)amino | isopropyl | >10 | 9.9 |
| [1-(hydroxymethyl)-2-methylpropyl]amino | (2-hydroxybenzyl)amino | isopropyl | 6.9 | 2.5 |
| (4-aminocyclohexyl)amino | (4-hydroxybenzyl)amino | isopropyl | >10 | 1.4 |

The invention claimed is:

1. A compound of formula I, or a pharmaceutically acceptable salt thereof,

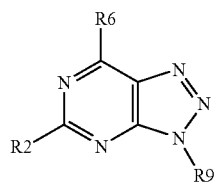

wherein
R6 is R6'-X,
wherein X is —NH—, —O—, or —S—, and R6' is an aryl group optionally substituted by one or more substituents selected from chloro, fluoro, hydroxyl, amino, acylamino, acyloxy, carboxyl and amido;
or
X is —N-(substituted arylalkyl), wherein said substituted arylalkyl is benzylamine substituted by one or more substituents selected from halogen, amino, hydroxy, cyano, nitro, mercapto, alkoxy, alkylamino, dialkylamino, acylamino, carbamoylamino, acyloxy, alkylmercapto, carboxyl, amido, sulfo, sulfamido, sulfamoyl, ureido, guanadino or α-(aminomethyl)-mono-, di- or tri-substituted benzyl alcohol and R6' is H;

R2 is

R2'-X, wherein X is —NH—;

R2' is independently

Substituted alkyl, acyl, cycloalkyl, substituted cycloalkyl, cycloheteroalkyl, substituted cycloheteroalkyl, cycloalkyl alkyl, aryl, substituted aryl, arylalkyl, heterocyclyl, heteroaryl, substituted heteroaryl, heteroalkyl or heteroarylalkyl, wherein said substituted groups are substituted by one or more substituents selected from halogen, amino, acylamino, acyloxy, hydroxy, mercapto, alkoxy, alkylamino, dialkylamino, alkylmercapto, carboxyl, amido, sulfo, sulfamido, carbamoylamino, nitro and cyano;

R9 is alkyl.

2. A compound according to claim 1 wherein
said heterocyclyl is selected from thienyl, furyl, pyranyl, pyrrolyl, imidazolyl, pyrazolyl, pyridyl, pyrazinyl, pyrimidinyl, pyridazinyl, isothiazolyl, and isoxazyl;
said aryl is selected from phenyl, biphenyl, naphthyl, tetrahydronaphthyl, fluorenyl, indenyl and phenanthrenyl;
said cycloheteroalkyl is selected from piperidinyl, piperazinyl, morpholinyl, pyrrolidinyl, imidazolidinyl;
said heteroaryl (HetAr) is selected from benzothienyl, naphthothienyl, benzofuranyl, chromenyl, indolyl, isoindolyl, indazolyl, quinolinyl, isoquinolinyl, phthalazinyl, cinnolinyl, quinazoliny, quinoxalinyl, carbazolyl, acridinyl.

3. A compound selected from
2-(4-aminocyclohexylamino)-6-benzylamino-9-isopropyl-8-azapurine,
2-[1-(hydroxymethyl)propylamino]-6-benzylamino-9-isopropyl-8-azapurine,
2-[1-(hydroxymethyl)propylamino]-6-benzylamino-9-methyl-8-azapurine,
2-[1-(hydroxymethyl)propylamino]-6-benzylamino-9-ethyl-8-azapurine,
2-(2-aminopropylamino)-6-benzylamino-9-isopropyl-8-azapurine,
2-(2-aminopropylamino)-6-benzylamino-9-methyl-8-azapurine,
2-(2-aminopropylamino)-6-benzylamino-9-ethyl-8-azapurine,
2-(2-hydroxypropylamino)-6-benzylamino-9-isopropyl-8-azapurine,
2-(2-hydroxypropylamino)-6-benzylamino-9-methyl-8-azapurine,
2-(2-hydroxypropylamino)-6-benzylamino-9-ethyl-8-azapurine,
2-(1(R)-isopropyl-2-hydroxyethylamino)-6-benzylamino-9-isopropyl-8-azapurine,
2-(1(R)-isopropyl-2-hydroxyethylamino)-6-benzylamino-9-methyl-8-azapurine,
2-(1(R)-isopropyl-2-hydroxyethylamino)-6-benzylamino-9-ethyl-8-azapurine,
2-(4-aminocyclohexylamino)-6-benzylamino-9-methyl-8-azapurine,
2-(4-aminocyclohexylamino)-6-benzylamino-9-ethyl-8-azapurine,
2-(2-aminocyclohexylamino)-6-benzylamino-9-isopropyl-8-azapurine,
2-(2-aminocyclohexylamino)-6-benzylamino-9-methyl-8-azapurine,
2-(2-aminocyclohexylamino)-6-benzylamino-9-ethyl-8-azapurine,
2-[1-(hydroxymethyl)propylamino]-6-(3-acetoxybenzylamino)-9-isopropyl-8-azapurine,
2-[1-(hydroxymethyl)propylamino]-6-(3-acetoxybenzylamino)-9-methyl-8-azapurine,
2-[1-(hydroxymethyl)propylamino]-6-(3-acetoxybenzylamino)-9-ethyl-8-azapurine,
2-(2-aminopropylamino)-6-(3-acetoxybenzylamino)-9-isopropyl-8-azapurine,
2-(2-aminopropylamino)-6-(3-acetoxybenzylamino)-9-methyl-8-azapurine,
2-(2-aminopropylamino)-6-(3-acetoxybenzylamino)-9-ethyl-8-azapurine,
2-(2-hydroxypropylamino)-6-(3-acetoxybenzylamino)-9-isopropyl-8-azapurine,
2-(2-hydroxypropylamino)-6-(3-acetoxybenzylamino)-9-methyl-8-azapurine,
2-(2-hydroxypropylamino)-6-(3-acetoxybenzylamino)-9-ethyl-8-azapurine,
2-(1(R)-isopropyl-2-hydroxyethylamino)-6-(3-acetoxybenzylamino)-9-isopropyl-8-azapurine,
2-(1(R)-isopropyl-2-hydroxyethylamino)-6-(3-acetoxybenzylamino)-9-methyl-8-azapurine,
2-(1(R)-isopropyl-2-hydroxyethylamino)-6-(3-acetoxybenzylamino)-9-ethyl-8-azapurine,
2-(4-aminocyclohexylamino)-6-(3-acetoxybenzylamino)-9-isopropyl-8-azapurine,
2-(4-aminocyclohexylamino)-6-(3-acetoxybenzylamino)-9-methyl-8-azapurine,
2-(4-aminocyclohexylamino)-6-(3-acetoxybenzylamino)-9-ethyl-8-azapurine,
2-(2-aminocyclohexylamino)-6-(3-acetoxybenzylamino)-9-isopropyl-8-azapurine,
2-(2-aminocyclohexylamino)-6-(3-acetoxybenzylamino)-9-methyl-8-azapurine,
2-(2-aminocyclohexylamino)-6-(3-acetoxybenzylamino)-9-ethyl-8-azapurine,
2-[1-(hydroxymethyl)propylamino]-6-(2-hydroxy-3-methoxybenzylamino)-9-isopropyl-8-azapurine,
2-[1-(hydroxymethyl)propylamino]-6-(2-hydroxy-3-methoxybenzylamino)-9-methyl-8-azapurine,
2-[1-(hydroxymethyl)propylamino]-6-(2-hydroxy-3-methoxybenzylamino)-9-ethyl-8-azapurine,
2-(2-aminopropylamino)-6-(2-hydroxy-3-methoxybenzylamino)-9-isopropyl-8-azapurine,
2-(2-aminopropylamino)-6-(2-hydroxy-3-methoxybenzylamino)-9-methyl-8-azapurine,
2-(2-aminopropylamino)-6-(2-hydroxy-3-methoxybenzylamino)-9-ethyl-8-azapurine,
2-(2-hydroxypropylamino)-6-(2-hydroxy-3-methoxybenzylamino)-9-isopropyl-8-azapurine,
2-(2-hydroxypropylamino)-6-(2-hydroxy-3-methoxybenzylamino)-9-methyl-8-azapurine,
2-(2-hydroxypropylamino)-6-(2-hydroxy-3-methoxybenzylamino)-9-ethyl-8-azapurine,
2-(1(R)-isopropyl-2-hydroxyethylamino)-6-(2-hydroxy-3-methoxybenzylamino)-9-isopropyl-8-azapurine,
2-(1(R)-isopropyl-2-hydroxyethylamino)-6-(2-hydroxy-3-methoxybenzylamino)-9-methyl-8-azapurine,
2-(1(R)-isopropyl-2-hydroxyethylamino)-6-(2-hydroxy-3-methoxybenzylamino)-9-ethyl-8-azapurine,
2-(4-aminocyclohexylamino)-6-(2-hydroxy-3-methoxybenzylamino)-9-isopropyl-8-azapurine,
2-(4-aminocyclohexylamino)-6-(2-hydroxy-3-methoxybenzylamino)-9-methyl-8-azapurine,
2-(4-aminocyclohexylamino)-6-(2-hydroxy-3-methoxybenzylamino)-9-ethyl-8-azapurine,
2-(2-aminocyclohexylamino)-6-(2-hydroxy-3-methoxybenzylamino)-9-isopropyl-8-azapurine,
2-(2-aminocyclohexylamino)-6-(2-hydroxy-3-methoxybenzylamino)-9-methyl-8-azapurine,
2-(2-aminocyclohexylamino)-6-(2-hydroxy-3-methoxybenzylamino)-9-ethyl-8-azapurine,
2-[1-(hydroxymethyl)propylamino]-6-(2,3-dihydroxy-4-methoxybenzylamino)-9-isopropyl-8-azapurine,
2-[1-(hydroxymethyl)propylamino]-6-(2,3-dihydroxy-4-methoxybenzylamino)-9-methyl-8-azapurine,
2-[1-(hydroxymethyl)propylamino]-6-(2,3-dihydroxy-4-methoxybenzylamino)-9-ethyl-8-azapurine,
2-(2-aminopropylamino)-6-(2,3-dihydroxy-4-methoxybenzylamino)-9-isopropyl-8-azapurine,
2-(2-aminopropylamino)-6-(2,3-dihydroxy-4-methoxybenzylamino)-9-methyl-8-azapurine, 2-(2-aminopropylamino)-6-(2,3-dihydroxy-4-methoxy-benzylamino)-9-ethyl-8-azapurine,
2-(2-hydroxypropylamino)-6-(2,3-dihydroxy-4-methoxy-benzylamino)-9-isopropyl-8-azapurine,
2-(2-hydroxypropylamino)-6-(2,3-dihydroxy-4-methoxy-benzylamino)-9-methyl-8-azapurine,
2-(2-hydroxypropylamino)-6-(2,3-dihydroxy-4-methoxy-benzylamino)-9-ethyl-8-azapurine,
2-(1(R)-isopropyl-2-hydroxyethylamino)-6-(2,3-dihydroxy-4-methoxybenzylamino)-9-isopropyl-8-azapurine,
2-(1(R)-isopropyl-2-hydroxyethylamino)-6-(2,3-dihydroxy-4-methoxybenzylamino)-9-methyl-8-azapurine,
2-(1(R)-isopropyl-2-hydroxyethylamino)-6-(2,3-dihydroxy-4-methoxybenzylamino)-9-ethyl-8-azapurine,
2-(4-aminocyclohexylamino)-6-(2,3-dihydroxy-4-methoxybenzylamino)-9-isopropyl-8-azapurine,
2-(4-aminocyclohexylamino)-6-(2,3-dihydroxy-4-methoxybenzylamino)-9-methyl-8-azapurine,
2-(4-aminocyclohexylamino)-6-(2,3-dihydroxy-4-methoxybenzylamino)-9-ethyl-8-azapurine,
2-(2-aminocyclohexylamino)-6-(2,3-dihydroxy-4-methoxybenzylamino)-9-isopropyl-8-azapurine,
2-(2-aminocyclohexylamino)-6-(2,3-dihydroxy-4-methoxybenzylamino)-9-methyl-8-azapurine,
2-(2-aminocyclohexylamino)-6-(2,3-dihydroxy-4-methoxybenzylamino)-9-ethyl-8-azapurine,
2-[1-(hydroxymethyl)propylamino]-6-(2,5-dihydroxy-4-methoxybenzylamino)-9-isopropyl-8-azapurine,
2-[1-(hydroxymethyl)propylamino]-6-(2,5-dihydroxy-4-methoxybenzylamino)-9-methyl-8-azapurine,
2-[1-(hydroxymethyl)propylamino]-6-(2,5-dihydroxy-4-methoxybenzylamino)-9-ethyl-8-azapurine,
2-(2-aminopropylamino)-6-(2,5-dihydroxy-4-methoxy-benzylamino)-9-isopropyl-8-azapurine,
2-(2-aminopropylamino)-6-(2,5-dihydroxy-4-methoxy-benzylamino)-9-methyl-8-azapurine,
2-(2-aminopropylamino)-6-(2,5-dihydroxy-4-methoxy-benzylamino)-9-ethyl-8-azapurine,
2-(2-hydroxypropylamino)-6-(2,5-dihydroxy-4-methoxy-benzylamino)-9-isopropyl-8-azapurine,
2-(2-hydroxypropylamino)-6-(2,5-dihydroxy-4-methoxy-benzylamino)-9-methyl-8-azapurine,
2-(2-hydroxypropylamino)-6-(2,5-dihydroxy-4-methoxy-benzylamino)-9-ethyl-8-azapurine,
2-(1(R)-isopropyl-2-hydroxyethylamino)-6-(2,5-dihydroxy-4-methoxybenzylamino)-9-isopropyl-8-azapurine,
2-(1(R)-isopropyl-2-hydroxyethylamino)-6-(2,5-dihydroxy-4-methoxybenzylamino)-9-methyl-8-azapurine,
2-(1(R)-isopropyl-2-hydroxyethylamino)-6-(2,5-dihydroxy-4-methoxybenzylamino)-9-ethyl-8-azapurine,
2-(4-aminocyclohexylamino)-6-(2,5-dihydroxy-4-methoxybenzylamino)-9-isopropyl-8-azapurine,
2-(4-aminocyclohexylamino)-6-(2,5-dihydroxy-4-methoxybenzylamino)-9-methyl-8-azapurine,
2-(4-aminocyclohexylamino)-6-(2,5-dihydroxy-4-methoxybenzylamino)-9-ethyl-8-azapurine,
2-(2-aminocyclohexylamino)-6-(2,5-dihydroxy-4-methoxybenzylamino)-9-isopropyl-8-azapurine,
2-(2-aminocyclohexylamino)-6-(2,5-dihydroxy-4-methoxybenzylamino)-9-methyl-8-azapurine,
2-(2-aminocyclohexylamino)-6-(2,5-dihydroxy-4-methoxybenzylamino)-9-ethyl-8-azapurine,
2-[1-(hydroxymethyl)propylamino]-6-(2,6-dihydroxy-4-methoxybenzylamino)-9-isopropyl-8-azapurine,
2-[1-(hydroxymethyl)propylamino]-6-(2,6-dihydroxy-4-methoxybenzylamino)-9-methyl-8-azapurine,
2-[1-(hydroxymethyl)propylamino]-6-(2,6-dihydroxy-4-methoxybenzylamino)-9-ethyl-8-azapurine,
2-(2-aminopropylamino)-6-(2,6-dihydroxy-4-methoxy-benzylamino)-9-isopropyl-8-azapurine,
2-(2-aminopropylamino)-6-(2,6-dihydroxy-4-methoxy-benzylamino)-9-methyl-8-azapurine,
2-(2-aminopropylamino)-6-(2,6-dihydroxy-4-methoxy-benzylamino)-9-ethyl-8-azapurine,
2-(2-hydroxypropylamino)-6-(2,6-dihydroxy-4-methoxy-benzylamino)-9-isopropyl-8-azapurine,
2-(2-hydroxypropylamino)-6-(2,6-dihydroxy-4-methoxy-benzylamino)-9-methyl-8-azapurine,
2-(2-hydroxypropylamino)-6-(2,6-dihydroxy-4-methoxy-benzylamino)-9-ethyl-8-azapurine,
2-(1(R)-isopropyl-2-hydroxyethylamino)-6-(2,6-dihydroxy-4-methoxybenzylamino)-9-isopropyl-8-azapurine,
2-(1(R)-isopropyl-2-hydroxyethylamino)-6-(2,6-dihydroxy-4-methoxybenzylamino)-9-methyl-8-azapurine,
2-(1(R)-isopropyl-2-hydroxyethylamino)-6-(2,6-dihydroxy-4-methoxybenzylamino)-9-ethyl-8-azapurine,
2-(4-aminocyclohexylamino)-6-(2,6-dihydroxy-4-methoxybenzylamino)-9-isopropyl-8-azapurine,
2-(4-aminocyclohexylamino)-6-(2,6-dihydroxy-4-methoxybenzylamino)-9-methyl-8-azapurine,
2-(4-aminocyclohexylamino)-6-(2,6-dihydroxy-4-methoxybenzylamino)-9-ethyl-8-azapurine,
2-(2-aminocyclohexylamino)-6-(2,6-dihydroxy-4-methoxybenzylamino)-9-isopropyl-8-azapurine,
2-(2-aminocyclohexylamino)-6-(2,6-dihydroxy-4-methoxybenzylamino)-9-methyl-8-azapurine,
2-(2-aminocyclohexylamino)-6-(2,6-dihydroxy-4-methoxybenzylamino)-9-ethyl-8-azapurine,
2-[1-(hydroxymethyl)propylamino]-6-(2,3-dihydroxy-4-chlorobenzylamino)-9-isopropyl-8-azapurine,
2-[1-(hydroxymethyl)propylamino]-6-(2,3-dihydroxy-4-chlorobenzylamino)-9-methyl-8-azapurine,
2-[1-(hydroxymethyl)propylamino]-6-(2,3-dihydroxy-4-chlorobenzylamino)-9-ethyl-8-azapurine,
2-(2-aminopropylamino)-6-(2,3-dihydroxy-4-chlorobenzylamino)-9-isopropyl-8-azapurine,
2-(2-aminopropylamino)-6-(2,3-dihydroxy-4-chlorobenzylamino)-9-methyl-8-azapurine,
2-(2-aminopropylamino)-6-(2,3-dihydroxy-4-chlorobenzylamino)-9-ethyl-8-azapurine,
2-(2-hydroxypropylamino)-6-(2,3-dihydroxy-4-chlorobenzylamino)-9-isopropyl-8-azapurine,
2-(2-hydroxypropylamino)-6-(2,3-dihydroxy-4-chlorobenzylamino)-9-methyl-8-azapurine,
2-(2-hydroxypropylamino)-6-(2,3-dihydroxy-4-chlorobenzylamino)-9-ethyl-8-azapurine,
2-(1(R)-isopropyl-2-hydroxyethylamino)-6-(2,3-dihydroxy-4-chlorobenzylamino)-9-isopropyl-8-azapurine,
2-(1(R)-isopropyl-2-hydroxyethylamino)-6-(2,3-dihydroxy-4-chlorobenzylamino)-9-methyl-8-azapurine,
2-(1(R)-isopropyl-2-hydroxyethylamino)-6-(2,3-dihydroxy-4-chlorobenzylamino)-9-ethyl-8-azapurine,
2-(4-aminocyclohexylamino)-6-(2,3-dihydroxy-4-chlorobenzylamino)-9-isopropyl-8-azapurine,
2-(4-aminocyclohexylamino)-6-(2,3-dihydroxy-4-chlorobenzylamino)-9-methyl-8-azapurine,
2-(4-aminocyclohexylamino)-6-(2,3-dihydroxy-4-chlorobenzylamino)-9-ethyl-8-azapurine,
2-(2-aminocyclohexylamino)-6-(2,3-dihydroxy-4-chlorobenzylamino)-9-isopropyl-8-azapurine, 2-(2-aminocyclohexylamino)-6-(2,3-dihydroxy-4-chlorobenzylamino)-9-methyl-8-azapurine,
2-(2-aminocyclohexylamino)-6-(2,3-dihydroxy-4-chlorobenzylamino)-9-ethyl-8-azapurine,
2-[1-(hydroxymethyl)propylamino]-6-(2,5-dihydroxy-4-chlorobenzylamino)-9-isopropyl-8-azapurine,
2-[1-(hydroxymethyl)propylamino]-6-(2,5-dihydroxy-4-chlorobenzylamino)-9-methyl-8-azapurine,
2-[1-(hydroxymethyl)propylamino]-6-(2,5-dihydroxy-4-chlorobenzylamino)-9-ethyl-8-azapurine,
2-(2-aminopropylamino)-6-(2,5-dihydroxy-4-chlorobenzylamino)-9-isopropyl-8-azapurine,
2-(2-aminopropylamino)-6-(2,5-dihydroxy-4-chlorobenzylamino)-9-methyl-8-azapurine,
2-(2-aminopropylamino)-6-(2,5-dihydroxy-4-chlorobenzylamino)-9-ethyl-8-azapurine,
2-(2-hydroxypropylamino)-6-(2,5-dihydroxy-4-chlorobenzylamino)-9-isopropyl-8-azapurine,
2-(2-hydroxypropylamino)-6-(2,5-dihydroxy-4-chlorobenzylamino)-9-methyl-8-azapurine,
2-(2-hydroxypropylamino)-6-(2,5-dihydroxy-4-chlorobenzylamino)-9-ethyl-8-azapurine,
2-(1(R)-isopropyl-2-hydroxyethylamino)-6-(2,5-dihydroxy-4-chlorobenzylamino)-9-isopropyl-8-azapurine,
2-(1(R)-isopropyl-2-hydroxyethylamino)-6-(2,5-dihydroxy-4-chlorobenzylamino)-9-methyl-8-azapurine,
2-(1(R)-isopropyl-2-hydroxyethylamino)-6-(2,5-dihydroxy-4-chlorobenzylamino)-9-ethyl-8-azapurine,
2-(4-aminocyclohexylamino)-6-(2,5-dihydroxy-4-chlorobenzylamino)-9-isopropyl-8-azapurine,
2-(4-aminocyclohexylamino)-6-(2,5-dihydroxy-4-chlorobenzylamino)-9-methyl-8-azapurine,
2-(4-aminocyclohexylamino)-6-(2,5-dihydroxy-4-chlorobenzylamino)-9-ethyl-8-azapurine,
2-[1-(hydroxymethyl)propylamino]-6-(2,6-dihydroxy-4-chlorobenzylamino)-9-isopropyl-8-azapurine,
2-[1-(hydroxymethyl)propylamino]-6-(2,6-dihydroxy-4-chlorobenzylamino)-9-methyl-8-azapurine,
2-[1-(hydroxymethyl)propylamino]-6-(2,6-dihydroxy-4-chlorobenzylamino)-9-ethyl-8-azapurine,
2-(2-aminopropylamino)-6-(2,6-dihydroxy-4-chlorobenzylamino)-9-isopropyl-8-azapurine,
2-(2-aminopropylamino)-6-(2,6-dihydroxy-4-chlorobenzylamino)-9-methyl-8-azapurine,
2-(2-aminopropylamino)-6-(2,6-dihydroxy-4-chlorobenzylamino)-9-ethyl-8-azapurine,
2-(2-hydroxypropylamino)-6-(2,6-dihydroxy-4-chlorobenzylamino)-9-isopropyl-8-azapurine,
2-(2-hydroxypropylamino)-6-(2,6-dihydroxy-4-chlorobenzylamino)-9-methyl-8-azapurine,
2-(2-hydroxypropylamino)-6-(2,6-dihydroxy-4-chlorobenzylamino)-9-ethyl-8-azapurine,
2-(1(R)-isopropyl-2-hydroxyethylamino)-6-(2,6-dihydroxy-4-chlorobenzylamino)-9-isopropyl-8-azapurine,
2-(1(R)-isopropyl-2-hydroxyethylamino)-6-(2,6-dihydroxy-4-chlorobenzylamino)-9-methyl-8-azapurine,
2-(1(R)-isopropyl-2-hydroxyethylamino)-6-(2,6-dihydroxy-4-chlorobenzylamino)-9-ethyl-8-azapurine,
2-(4-aminocyclohexylamino)-6-(2,6-dihydroxy-4-chlorobenzylamino)-9-isopropyl-8-azapurine,
2-(4-aminocyclohexylamino)-6-(2,6-dihydroxy-4-chlorobenzylamino)-9-methyl-8-azapurine,
2-(4-aminocyclohexylamino)-6-(2,6-dihydroxy-4-chlorobenzylamino)-9-ethyl-8-azapurine,
2-(2-aminocyclohexylamino)-6-(2,6-dihydroxy-4-chlorobenzylamino)-9-isopropyl-8-azapurine,
2-(2-aminocyclohexylamino)-6-(2,6-dihydroxy-4-chlorobenzylamino)-9-methyl-8-azapurine,
2-(2-aminocyclohexylamino)-6-(2,6-dihydroxy-4-chlorobenzylamino)-9-ethyl-8-azapurine,
2-[1-(hydroxymethyl)propylamino]-6-(2-acetoxybenzylamino)-9-isopropyl-8-azapurine,
2-[1-(hydroxymethyl)propylamino]-6-(2-acetoxybenzylamino)-9-methyl-8-azapurine,
2-[1-(hydroxymethyl)propylamino]-6-(2-acetoxybenzylamino)-9-ethyl-8-azapurine,
2-(2-aminopropylamino)-6-(2-acetoxybenzylamino)-9-isopropyl-8-azapurine,
2-(2-aminopropylamino)-6-(2-acetoxybenzylamino)-9-methyl-8-azapurine,
2-(2-aminopropylamino)-6-(2-acetoxybenzylamino)-9-ethyl-8-azapurine,
2-(2-hydroxypropylamino)-6-(2-acetoxybenzylamino)-9-isopropyl-8-azapurine,
2-(2-hydroxypropylamino)-6-(2-acetoxybenzylamino)-9-methyl-8-azapurine,
2-(2-hydroxypropylamino)-6-(2-acetoxybenzylamino)-9-ethyl-8-azapurine,
2-(1(R)-isopropyl-2-hydroxyethylamino)-6-(2-acetoxybenzylamino)-9-isopropyl-8-azapurine,
2-(1(R)-isopropyl-2-hydroxyethylamino)-6-(2-acetoxybenzylamino)-9-methyl-8-azapurine,
2-(1(R)-isopropyl-2-hydroxyethylamino)-6-(2-acetoxybenzylamino)-9-ethyl-8-azapurine,
2-(4-aminocyclohexylamino)-6-(2-acetoxybenzylamino)-9-isopropyl-8-azapurine,
2-(4-aminocyclohexylamino)-6-(2-acetoxybenzylamino)-9-methyl-8-azapurine,
2-(4-aminocyclohexylamino)-6-(2-acetoxybenzylamino)-9-ethyl-8-azapurine,
2-(2-aminocyclohexylamino)-6-(2-acetoxybenzylamino)-9-isopropyl-8-azapurine,
2-(2-aminocyclohexylamino)-6-(2-acetoxybenzylamino)-9-methyl-8-azapurine,
2-(2-aminocyclohexylamino)-6-(2-acetoxybenzylamino)-9-ethyl-8-azapurine,
2-[1-(hydroxymethyl)propylamino]-6-(2-aminobenzylamino)-9-isopropyl-8-azapurine,
2-[1-(hydroxymethyl)propylamino]-6-(2-aminobenzylamino)-9-methyl-8-azapurine,
2-[1-(hydroxymethyl)propylamino]-6-(2-aminobenzylamino)-9-ethyl-8-azapurine,
2-(2-aminopropylamino)-6-(2-aminobenzylamino)-9-isopropyl-8-azapurine,
2-(2-aminopropylamino)-6-(2-aminobenzylamino)-9-methyl-8-azapurine,
2-(2-aminopropylamino)-6-(2-aminobenzylamino)-9-ethyl-8-azapurine,
2-(2-hydroxypropylamino)-6-(2-aminobenzylamino)-9-isopropyl-8-azapurine,
2-(2-hydroxypropylamino)-6-(2-aminobenzylamino)-9-methyl-8-azapurine,
2-(2-hydroxypropylamino)-6-(2-aminobenzylamino)-9-ethyl-8-azapurine,
2-(1(R)-isopropyl-2-hydroxyethylamino)-6-(2-aminobenzylamino)-9-isopropyl-8-azapurine,
2-(1(R)-isopropyl-2-hydroxyethylamino)-6-(2-aminobenzylamino)-9-methyl-8-azapurine,
2-(1(R)-isopropyl-2-hydroxyethylamino)-6-(2-aminobenzylamino)-9-ethyl-8-azapurine,
2-(4-aminocyclohexylamino)-6-(2-aminobenzylamino)-9-isopropyl-8-azapurine, 2-(4-aminocyclohexylamino)-6-(2-aminobenzylamino)-9-methyl-8-azapurine,
2-(4-aminocyclohexylamino)-6-(2-aminobenzylamino)-9-ethyl-8-azapurine,
2-(2-aminocyclohexylamino)-6-(2-aminobenzylamino)-9-isopropyl-8-azapurine,
2-(2-aminocyclohexylamino)-6-(2-aminobenzylamino)-9-methyl-8-azapurine,
2-(2-aminocyclohexylamino)-6-(2-aminobenzylamino)-9-ethyl-8-azapurine,
2-[1-(hydroxymethyl)propylamino]-6-(2-amino-6-chlorobenzylamino)-9-isopropyl-8-azapurine,
2-[1-(hydroxymethyl)propylamino]-6-(2-amino-6-chlorobenzylamino)-9-methyl-8-azapurine,
2-[1-(hydroxymethyl)propylamino]-6-(2-amino-6-chlorobenzylamino)-9-ethyl-8-azapurine,
2-(2-aminopropylamino)-6-(2-amino-6-chlorobenzylamino)-9-isopropyl-8-azapurine,
2-(2-aminopropylamino)-6-(2-amino-6-chlorobenzylamino)-9-methyl-8-azapurine,
2-(2-aminopropylamino)-6-(2-amino-6-chlorobenzylamino)-9-ethyl-8-azapurine,
2-(2-hydroxypropylamino)-6-(2-amino-6-chlorobenzylamino)-9-isopropyl-8-azapurine,
2-(2-hydroxypropylamino)-6-(2-amino-6-chlorobenzylamino)-9-methyl-8-azapurine,
2-(2-hydroxypropylamino)-6-(2-amino-6-chlorobenzylamino)-9-ethyl-8-azapurine,
2-(1(R)-isopropyl-2-hydroxyethylamino)-6-(2-amino-6-chlorobenzylamino)-9-isopropyl-8-azapurine,
2-(1(R)-isopropyl-2-hydroxyethylamino)-6-(2-amino-6-chlorobenzylamino)-9-methyl-8-azapurine,
2-(1(R)-isopropyl-2-hydroxyethylamino)-6-(2-amino-6-chlorobenzylamino)-9-ethyl-8-azapurine,
2-(4-aminocyclohexylamino)-6-(2-amino-6-chlorobenzylamino)-9-isopropyl-8-azapurine,
2-(4-aminocyclohexylamino)-6-(2-amino-6-chlorobenzylamino)-9-methyl-8-azapurine,
2-(4-aminocyclohexylamino)-6-(2-amino-6-chlorobenzylamino)-9-ethyl-8-azapurine,
2-(2-aminocyclohexylamino)-6-(2-amino-6-chlorobenzylamino)-9-isopropyl-8-azapurine,
2-(2-aminocyclohexylamino)-6-(2-amino-6-chlorobenzylamino)-9-methyl-8-azapurine,
2-(2-aminocyclohexylamino)-6-(2-amino-6-chlorobenzylamino)-9-ethyl-8-azapurine,
2-[1-(hydroxymethyl)propylamino]-6-(3-amino-4-chlorobenzylamino)-9-isopropyl-8-azapurine,
2-[1-(hydroxymethyl)propylamino]-6-(3-amino-4-chlorobenzylamino)-9-methyl-8-azapurine,
2-[1-(hydroxymethyl)propylamino]-6-(3-amino-4-chlorobenzylamino)-9-ethyl-8-azapurine,
2-(2-aminopropylamino)-6-(3-amino-4-chlorobenzylamino)-9-isopropyl-8-azapurine,
2-(2-aminopropylamino)-6-(3-amino-4-chlorobenzylamino)-9-methyl-8-azapurine,
2-(2-aminopropylamino)-6-(3-amino-4-chlorobenzylamino)-9-ethyl-8-azapurine,
2-(2-hydroxypropylamino)-6-(3-amino-4-chlorobenzylamino)-9-isopropyl-8-azapurine,
2-(2-hydroxypropylamino)-6-(3-amino-4-chlorobenzylamino)-9-methyl-8-azapurine,
2-(2-hydroxypropylamino)-6-(3-amino-4-chlorobenzylamino)-9-ethyl-8-azapurine,
2-(1(R)-isopropyl-2-hydroxyethylamino)-6-(3-amino-4-chlorobenzylamino)-9-isopropyl-8-azapurine,
2-(1(R)-isopropyl-2-hydroxyethylamino)-6-(3-amino-4-chlorobenzylamino)-9-methyl-8-azapurine,
2-(1(R)-isopropyl-2-hydroxyethylamino)-6-(3-amino-4-chlorobenzylamino)-9-ethyl-8-azapurine,
2-(4-aminocyclohexylamino)-6-(3-amino-4-chlorobenzylamino)-9-isopropyl-8-azapurine,
2-(4-aminocyclohexylamino)-6-(3-amino-4-chlorobenzylamino)-9-methyl-8-azapurine,
2-(4-aminocyclohexylamino)-6-(3-amino-4-chlorobenzylamino)-9-ethyl-8-azapurine,
2-(2-aminocyclohexylamino)-6-(3-amino-4-chlorobenzylamino)-9-isopropyl-8-azapurine,
2-(2-aminocyclohexylamino)-6-(3-amino-4-chlorobenzylamino)-9-methyl-8-azapurine,
2-(2-aminocyclohexylamino)-6-(3-amino-4-chlorobenzylamino)-9-ethyl-8-azapurine,
2-[1-(hydroxymethyl)propylamino]-6-anilino-9-isopropyl-8-azapurine,
2-[1-(hydroxymethyl)propylamino]-6-anilino-9-methyl-8-azapurine,
2-[1-(hydroxymethyl)propylamino]-6-anilino-9-ethyl-8-azapurine,
2-(2-aminopropylamino)-6-anilino-9-isopropyl-8-azapurine,
2-(2-aminopropylamino)-6-anilino-9-methyl-8-azapurine,
2-(2-aminopropylamino)-6-anilino-9-ethyl-8-azapurine,
2-(2-hydroxypropylamino)-6-anilino-9-isopropyl-8-azapurine,
2-(2-hydroxypropylamino)-6-anilino-9-methyl-8-azapurine,
2-(2-hydroxypropylamino)-6-anilino-9-ethyl-8-azapurine,
2-(1(R)-isopropyl-2-hydroxyethylamino)-6-anilino-9-isopropyl-8-azapurine,
2-(1(R)-isopropyl-2-hydroxyethylamino)-6-anilino-9-methyl-8-azapurine,
2-(1(R)-isopropyl-2-hydroxyethylamino)-6-anilino-9-ethyl-8-azapurine,
2-(4-aminocyclohexylamino)-6-anilino-9-isopropyl-8-azapurine,
2-(4-aminocyclohexylamino)-6-anilino-9-methyl-8-azapurine,
2-(4-aminocyclohexylamino)-6-anilino-9-ethyl-8-azapurine,
2-(2-aminocyclohexylamino)-6-anilino-9-isopropyl-8-azapurine,
2-(2-aminocyclohexylamino)-6-anilino-9-methyl-8-azapurine,
2-(2-aminocyclohexylamino)-6-anilino-9-ethyl-8-azapurine,
2-[1-(hydroxymethyl)propylamino]-6-(3-chloroanilino)-9-isopropyl-8-azapurine,
2-[1-(hydroxymethyl)propylamino]-6-(3-chloroanilino)-9-methyl-8-azapurine,
2-[1-(hydroxymethyl)propylamino]-6-(3-chloroanilino)-9-ethyl-8-azapurine,
2-(2-aminopropylamino)-6-(3-chloroanilino)-9-isopropyl-8-azapurine,
2-(2-aminopropylamino)-6-(3-chloroanilino)-9-methyl-8-azapurine,
2-(2-aminopropylamino)-6-(3-chloroanilino)-9-ethyl-8-azapurine,
2-(2-hydroxypropylamino)-6-(3-chloroanilino)-9-isopropyl-8-azapurine,
2-(2-hydroxypropylamino)-6-(3-chloroanilino)-9-methyl-8-azapurine, 2-(2-hydroxypropylamino)-6-(3-chloroanilino)-9-ethyl-8-azapurine,
2-(1(R)-isopropyl-2-hydroxyethylamino)-6-(3-chloroanilino)-9-isopropyl-8-azapurine,
2-(1(R)-isopropyl-2-hydroxyethylamino)-6-(3-chloroanilino)-9-methyl-8-azapurine,
2-(1(R)-isopropyl-2-hydroxyethylamino)-6-(3-chloroanilino)-9-ethyl-8-azapurine,
2-(4-aminocyclohexylamino)-6-(3-chloroanilino)-9-isopropyl-8-azapurine,
2-(4-aminocyclohexylamino)-6-(3-chloroanilino)-9-methyl-8-azapurine,
2-(4-aminocyclohexylamino)-6-(3-chloroanilino)-9-ethyl-8-azapurine,
2-(2-aminocyclohexylamino)-6-(3-chloroanilino)-9-isopropyl-8-azapurine,
2-(2-aminocyclohexylamino)-6-(3-chloroanilino)-9-methyl-8-azapurine,
2-(2-aminocyclohexylamino)-6-(3-chloroanilino)-9-ethyl-8-azapurine,
2-[1-(hydroxymethyl)propylamino]-6-(4-chloroanilino)-9-isopropyl-8-azapurine,
2-[1-(hydroxymethyl)propylamino]-6-(4-chloroanilino)-9-methyl-8-azapurine,
2-[1-(hydroxymethyl)propylamino]-6-(4-chloroanilino)-9-ethyl-8-azapurine,
2-(2-aminopropylamino)-6-(4-chloroanilino)-9-isopropyl-8-azapurine,
2-(2-aminopropylamino)-6-(4-chloroanilino)-9-methyl-8-azapurine,
2-(2-aminopropylamino)-6-(4-chloroanilino)-9-ethyl-8-azapurine,
2-(2-hydroxypropylamino)-6-(4-chloroanilino)-9-isopropyl-8-azapurine,
2-(2-hydroxypropylamino)-6-(4-chloroanilino)-9-methyl-8-azapurine,
2-(2-hydroxypropylamino)-6-(4-chloroanilino)-9-ethyl-8-azapurine,
2-(1(R)-isopropyl-2-hydroxyethylamino)-6-(4-chloroanilino)-9-isopropyl-8-azapurine,
2-(1(R)-isopropyl-2-hydroxyethylamino)-6-(4-chloroanilino)-9-methyl-8-azapurine,
2-(1(R)-isopropyl-2-hydroxyethylamino)-6-(4-chloroanilino)-9-ethyl-8-azapurine,
2-(4-aminocyclohexylamino)-6-(4-chloroanilino)-9-isopropyl-8-azapurine,
2-(4-aminocyclohexylamino)-6-(4-chloroanilino)-9-methyl-8-azapurine,
2-(4-aminocyclohexylamino)-6-(4-chloroanilino)-9-ethyl-8-azapurine,
2-(2-aminocyclohexylamino)-6-(4-chloroanilino)-9-isopropyl-8-azapurine,
2-(2-aminocyclohexylamino)-6-(4-chloroanilino)-9-methyl-8-azapurine,
2-(2-aminocyclohexylamino)-6-(4-chloroanilino)-9-ethyl-8-azapurine,
2-[1-(hydroxymethyl)propylamino]-6-(4-bromoanilino)-9-isopropyl-8-azapurine,
2-[1-(hydroxymethyl)propylamino]-6-(4-bromoanilino)-9-methyl-8-azapurine,
2-[1-(hydroxymethyl)propylamino]-6-(4-bromoanilino)-9-ethyl-8-azapurine,
2-(2-aminopropylamino)-6-(4-bromoanilino)-9-isopropyl-8-azapurine,
2-(2-aminopropylamino)-6-(4-bromoanilino)-9-methyl-8-azapurine,
2-(2-aminopropylamino)-6-(4-bromoanilino)-9-ethyl-8-azapurine,
2-(2-hydroxypropylamino)-6-(4-bromoanilino)-9-isopropyl-8-azapurine,
2-(2-hydroxypropylamino)-6-(4-bromoanilino)-9-methyl-8-azapurine,
2-(2-hydroxypropylamino)-6-(4-bromoanilino)-9-ethyl-8-azapurine,
2-(1(R)-isopropyl-2-hydroxyethylamino)-6-(4-bromoanilino)-9-isopropyl-8-azapurine,
2-(1(R)-isopropyl-2-hydroxyethylamino)-6-(4-bromoanilino)-9-methyl-8-azapurine,
2-(1(R)-isopropyl-2-hydroxyethylamino)-6-(4-bromoanilino)-9-ethyl-8-azapurine,
2-(4-aminocyclohexylamino)-6-(4-bromoanilino)-9-isopropyl-8-azapurine,
2-(4-aminocyclohexylamino)-6-(4-bromoanilino)-9-methyl-8-azapurine,
2-(4-aminocyclohexylamino)-6-(4-bromoanilino)-9-ethyl-8-azapurine,
2-(2-aminocyclohexylamino)-6-(4-bromoanilino)-9-isopropyl-8-azapurine,
2-(2-aminocyclohexylamino)-6-(4-bromoanilino)-9-methyl-8-azapurine,
2-(2-aminocyclohexylamino)-6-(4-bromoanilino)-9-ethyl-8-azapurine,
2-[1-(hydroxymethyl)propylamino]-6-(3-chloro-5-aminoanilino)-9-isopropyl-8-azapurine,
2-[1-(hydroxymethyl)propylamino]-6-(3-chloro-5-aminoanilino)-9-methyl-8-azapurine,
2-[1-(hydroxymethyl)propylamino]-6-(3-chloro-5-aminoanilino)-9-ethyl-8-azapurine,
2-(2-aminopropylamino)-6-(3-chloro-5-aminoanilino)-9-isopropyl-8-azapurine,
2-(2-aminopropylamino)-6-(3-chloro-5-aminoanilino)-9-methyl-8-azapurine,
2-(2-aminopropylamino)-6-(3-chloro-5-aminoanilino)-9-ethyl-8-azapurine,
2-(2-hydroxypropylamino)-6-(3-chloro-5-aminoanilino)-9-isopropyl-8-azapurine,
2-(2-hydroxypropylamino)-6-(3-chloro-5-aminoanilino)-9-methyl-8-azapurine,
2-(2-hydroxypropylamino)-6-(3-chloro-5-aminoanilino)-9-ethyl-8-azapurine,
2-(1(R)-isopropyl-2-hydroxyethylamino)-6-(3-chloro-5-aminoanilino)-9-isopropyl-8-azapurine,
2-(1(R)-isopropyl-2-hydroxyethylamino)-6-(3-chloro-5-aminoanilino)-9-methyl-8-azapurine,
2-(1(R)-isopropyl-2-hydroxyethylamino)-6-(3-chloro-5-aminoanilino)-9-ethyl-8-azapurine,
2-(4-aminocyclohexylamino)-6-(3-chloro-5-aminoanilino)-9-isopropyl-8-azapurine,
2-(4-aminocyclohexylamino)-6-(3-chloro-5-aminoanilino)-9-methyl-8-azapurine,
2-(4-aminocyclohexylamino)-6-(3-chloro-5-aminoanilino)-9-ethyl-8-azapurine,
2-(2-aminocyclohexylamino)-6-(3-chloro-5-aminoanilino)-9-isopropyl-8-azapurine,
2-(2-aminocyclohexylamino)-6-(3-chloro-5-aminoanilino)-9-methyl-8-azapurine,
2-(2-aminocyclohexylamino)-6-(3-chloro-5-aminoanilino)-9-ethyl-8-azapurine,
2-[1-(hydroxymethyl)propylamino]-6-(3-chloro-4-carboxyanilino)-9-isopropyl-8-azapurine,
2-[1-(hydroxymethyl)propylamino]-6-(3-chloro-4-carboxyanilino)-9-methyl-8-azapurine, 2-[1-(hydroxymethyl)propylamino]-6-(3-chloro-4-carboxyanilino)-9-ethyl-8-azapurine,
2-(2-aminopropylamino)-6-(3-chloro-4-carboxyanilino)-9-isopropyl-8-azapurine,
2-(2-aminopropylamino)-6-(3-chloro-4-carboxyanilino)-9-methyl-8-azapurine,
2-(2-aminopropylamino)-6-(3-chloro-4-carboxyanilino)-9-ethyl-8-azapurine,
2-(2-hydroxypropylamino)-6-(3-chloro-4-carboxyanilino)-9-isopropyl-8-azapurine,
2-(2-hydroxypropylamino)-6-(3-chloro-4-carboxyanilino)-9-methyl-8-azapurine,
2-(2-hydroxypropylamino)-6-(3-chloro-4-carboxyanilino)-9-ethyl-8-azapurine,
2-(1(R)-isopropyl-2-hydroxyethylamino)-6-(3-chloro-4-carboxyanilino)-9-isopropyl-8-azapurine,
2-(1(R)-isopropyl-2-hydroxyethylamino)-6-(3-chloro-4-carboxyanilino)-9-methyl-8-azapurine,
2-(1(R)-isopropyl-2-hydroxyethylamino)-6-(3-chloro-4-carboxyanilino)-9-ethyl-8-azapurine,
2-(4-aminocyclohexylamino)-6-(3-chloro-4-carboxyanilino)-9-isopropyl-8-azapurine,
2-(4-aminocyclohexylamino)-6-(3-chloro-4-carboxyanilino)-9-methyl-8-azapurine,
2-(4-aminocyclohexylamino)-6-(3-chloro-4-carboxyanilino)-9-ethyl-8-azapurine,
2-(2-aminocyclohexylamino)-6-(3-chloro-4-carboxyanilino)-9-isopropyl-8-azapurine,
2-(2-aminocyclohexylamino)-6-(3-chloro-4-carboxyanilino)-9-methyl-8-azapurine,
2-(2-aminocyclohexylamino)-6-(3-chloro-4-carboxyanilino)-9-ethyl-8-azapurine,
2-[1-(hydroxymethyl)propylamino]-2-(3-carboxy-4-chloroanilino)-9-isopropyl-8-azapurine,
2-[1-(hydroxymethyl)propylamino]-2-(3-carboxy-4-chloroanilino)-9-methyl-8-azapurine,
2-[1-(hydroxymethyl)propylamino]-2-(3-carboxy-4-chloroanilino)-9-ethyl-8-azapurine,
2-(2-aminopropylamino)-6-(3-carboxy-4-chloroanilino)-9-isopropyl-8-azapurine,
2-(2-aminopropylamino)-6-(3-carboxy-4-chloroanilino)-9-methyl-8-azapurine,
2-(2-aminopropylamino)-6-(3-carboxy-4-chloroanilino)-9-ethyl-8-azapurine,
2-(2-hydroxypropylamino)-6-(3-carboxy-4-chloroanilino)-9-isopropyl-8-azapurine,
2-(2-hydroxypropylamino)-6-(3-carboxy-4-chloroanilino)-9-methyl-8-azapurine,
2-(2-hydroxypropylamino)-6-(3-carboxy-4-chloroanilino)-9-ethyl-8-azapurine,
2-(1(R)-isopropyl-2-hydroxyethylamino)-6-(3-carboxy-4-chloroanilino)-9-isopropyl-8-azapurine,
2-(1(R)-isopropyl-2-hydroxyethylamino)-6-(3-carboxy-4-chloroanilino)-9-methyl-8-azapurine,
2-(1(R)-isopropyl-2-hydroxyethylamino)-6-(3-carboxy-4-chloroanilino)-9-ethyl-8-azapurine,
2-(4-aminocyclohexylamino)-6-(3-carboxy-4-chloroanilino)-9-isopropyl-8-azapurine,
2-(4-aminocyclohexylamino)-6-(3-carboxy-4-chloroanilino)-9-methyl-8-azapurine,
2-(4-aminocyclohexylamino)-6-(3-carboxy-4-chloroanilino)-9-ethyl-8-azapurine,
2-(2-aminocyclohexylamino)-6-(3-carboxy-4-chloroanilino)-9-isopropyl-8-azapurine,
2-(2-aminocyclohexylamino)-6-(3-carboxy-4-chloroanilino)-9-methyl-8-azapurine,
2-(2-aminocyclohexylamino)-6-(3-carboxy-4-chloroanilino)-9-ethyl-8-azapurine,
2-[1-(hydroxymethyl)propylamino]-6-(3-amino-4-chloroanilino)-9-isopropyl-8-azapurine,
2-[1-(hydroxymethyl)propylamino]-6-(3-amino-4-chloroanilino)-9-methyl-8-azapurine,
2-[1-(hydroxymethyl)propylamino]-6-(3-amino-4-chloroanilino)-9-ethyl-8-azapurine,
2-(2-aminopropylamino)-6-(3-amino-4-chloroanilino)-9-isopropyl-8-azapurine,
2-(2-aminopropylamino)-6-(3-amino-4-chloroanilino)-9-methyl-8-azapurine,
2-(2-aminopropylamino)-6-(3-amino-4-chloroanilino)-9-ethyl-8-azapurine,
2-(2-hydroxypropylamino)-6-(3-amino-4-chloroanilino)-9-isopropyl-8-azapurine,
2-(2-hydroxypropylamino)-6-(3-amino-4-chloroanilino)-9-methyl-8-azapurine,
2-(2-hydroxypropylamino)-6-(3-amino-4-chloroanilino)-9-ethyl-8-azapurine,
2-(1(R)-isopropyl-2-hydroxyethylamino)-6-(3-amino-4-chloroanilino)-9-isopropyl-8-azapurine,
2-(1(R)-isopropyl-2-hydroxyethylamino)-6-(3-amino-4-chloroanilino)-9-methyl-8-azapurine,
2-(1(R)-isopropyl-2-hydroxyethylamino)-6-(3-amino-4-chloroanilino)-9-ethyl-8-azapurine,
2-(4-aminocyclohexylamino)-6-(3-amino-4-chloroanilino)-9-isopropyl-8-azapurine,
2-(4-aminocyclohexylamino)-6-(3-amino-4-chloroanilino)-9-methyl-8-azapurine,
2-(4-aminocyclohexylamino)-6-(3-amino-4-chloroanilino)-9-ethyl-8-azapurine,
2-(2-aminocyclohexylamino)-6-(3-amino-4-chloroanilino)-9-isopropyl-8-azapurine,
2-(2-aminocyclohexylamino)-6-(3-amino-4-chloroanilino)-9-methyl-8-azapurine,
2-(2-aminocyclohexylamino)-6-(3-amino-4-chloroanilino)-9-ethyl-8-azapurine,
2-[1-(hydroxymethyl)propylamino]-6-(3-chloro-4-aminoanilino)-9-isopropyl-8-azapurine,
2-[1-(hydroxymethyl)propylamino]-6-(3-chloro-4-aminoanilino)-9-methyl-8-azapurine,
2-[1-(hydroxymethyl)propylamino]-6-(3-chloro-4-aminoanilino)-9-ethyl-8-azapurine,
2-(2-aminopropylamino)-6-(3-chloro-4-aminoanilino)-9-isopropyl-8-azapurine,
2-(2-aminopropylamino)-6-(3-chloro-4-aminoanilino)-9-methyl-8-azapurine,
2-(2-aminopropylamino)-6-(3-chloro-4-aminoanilino)-9-ethyl-8-azapurine,
2-(2-hydroxypropylamino)-6-(3-chloro-4-aminoanilino)-9-isopropyl-8-azapurine,
2-(2-hydroxypropylamino)-6-(3-chloro-4-aminoanilino)-9-methyl-8-azapurine,
2-(2-hydroxypropylamino)-6-(3-chloro-4-aminoanilino)-9-ethyl-8-azapurine,
2-(1(R)-isopropyl-2-hydroxyethylamino)-6-(3-chloro-4-aminoanilino)-9-isopropyl-8-azapurine,
2-(1(R)-isopropyl-2-hydroxyethylamino)-6-(3-chloro-4-aminoanilino)-9-methyl-8-azapurine,
2-(1(R)-isopropyl-2-hydroxyethylamino)-6-(3-chloro-4-aminoanilino)-9-ethyl-8-azapurine,
2-(4-aminocyclohexylamino)-6-(3-chloro-4-aminoanilino)-9-isopropyl-8-azapurine,
2-(4-aminocyclohexylamino)-6-(3-chloro-4-aminoanilino)-9-methyl-8-azapurine, 2-(4-aminocyclohexylamino)-6-(3-chloro-4-aminoanilino)-9-ethyl-8-azapurine,
2-(2-aminocyclohexylamino)-6-(3-chloro-4-aminoanilino)-9-isopropyl-8-azapurine,
2-(2-aminocyclohexylamino)-6-(3-chloro-4-aminoanilino)-9-methyl-8-azapurine,
2-(2-aminocyclohexylamino)-6-(3-chloro-4-aminoanilino)-9-ethyl-8-azapurine,
2-[1-(hydroxymethyl)propylamino]-6-(3-carboxy-4-hydroxyanilino)-9-isopropyl-8-azapurine,
2-[1-(hydroxymethyl)propylamino]-6-(3-carboxy-4-hydroxyanilino)-9-methyl-8-azapurine,
2-[1-(hydroxymethyl)propylamino]-6-(3-carboxy-4-hydroxyanilino)-9-ethyl-8-azapurine,
2-(2-aminopropylamino)-6-(3-carboxy-4-hydroxyanilino)-9-isopropyl-8-azapurine,
2-(2-aminopropylamino)-6-(3-carboxy-4-hydroxyanilino)-9-methyl-8-azapurine,
2-(2-aminopropylamino)-6-(3-carboxy-4-hydroxyanilino)-9-ethyl-8-azapurine,
2-(2-hydroxypropylamino)-6-(3-carboxy-4-hydroxyanilino)-9-isopropyl-8-azapurine,
2-(2-hydroxypropylamino)-6-(3-carboxy-4-hydroxyanilino)-9-methyl-8-azapurine,
2-(2-hydroxypropylamino)-6-(3-carboxy-4-hydroxyanilino)-9-ethyl-8-azapurine,
2-(1(R)-isopropyl-2-hydroxyethylamino)-6-(3-carboxy-4-hydroxyanilino)-9-isopropyl-8-azapurine,
2-(1(R)-isopropyl-2-hydroxyethylamino)-6-(3-carboxy-4-hydroxyanilino)-9-methyl-8-azapurine,
2-(1(R)-isopropyl-2-hydroxyethylamino)-6-(3-carboxy-4-hydroxyanilino)-9-ethyl-8-azapurine,
2-(4-aminocyclohexylamino)-6-(3-carboxy-4-hydroxyanilino)-9-isopropyl-8-azapurine,
2-(4-aminocyclohexylamino)-6-(3-carboxy-4-hydroxyanilino)-9-methyl-8-azapurine,
2-(4-aminocyclohexylamino)-6-(3-carboxy-4-hydroxyanilino)-9-ethyl-8-azapurine,
2-(2-aminocyclohexylamino)-6-(3-carboxy-4-hydroxyanilino)-9-isopropyl-8-azapurine,
2-(2-aminocyclohexylamino)-6-(3-carboxy-4-hydroxyanilino)-9-methyl-8-azapurine,
2-(2-aminocyclohexylamino)-6-(3-carboxy-4-hydroxyanilino)-9-ethyl-8-azapurine,
2-(2-hydroxypropylamino)-6-[N-(3,4-dihydroxybenzyl)-N-methyl]amino-9-isopropyl-8-azapurine,
2-(2-hydroxypropylamino)-6-[N-(3,4-dihydroxybenzyl)-N-methyl]amino-9-methyl-8-azapurine,
2-(2-hydroxypropylamino)-6-[N-(3,4-dihydroxybenzyl)-N-methyl]amino-9-ethyl-8-azapurine,
2-(1(R)-isopropyl-2-hydroxyethylamino)-6-[N-(3,4-dihydroxybenzyl)-N-methyl]amino-9-isopropyl-8-azapurine,
2-(1(R)-isopropyl-2-hydroxyethylamino)-6-[N-(3,4-dihydroxybenzyl)-N-methyl]amino-9-methyl-8-azapurine,
2-(1(R)-isopropyl-2-hydroxyethylamino)-6-[N-(3,4-dihydroxybenzyl)-N-methyl]amino-9-ethyl-8-azapurine,
2-(2-hydroxypropylamino)-6-[1-(3,4-dihydroxyphenyl)ethyl]amino-9-isopropyl-8-azapurine,
2-(2-hydroxypropylamino)-6-[1-(3,4-dihydroxyphenyl)ethyl]amino-9-methyl-8-azapurine,
2-(2-hydroxypropylamino)-6-[1-(3,4-dihydroxyphenyl)ethyl]amino-9-ethyl-8-azapurine,
2-(1(R)-isopropyl-2-hydroxyethylamino)-6-[1-(3,4-dihydroxyphenyl)ethyl]amino-9-isopropyl-8-azapurine,
2-(1(R)-isopropyl-2-hydroxyethylamino)-6-[1-(3,4-dihydroxyphenyl)ethyl]amino-9-methyl-8-azapurine,
2-(1(R)-isopropyl-2-hydroxyethylamino)-6-[1-(3,4-dihydroxyphenyl)ethyl]amino-9-ethyl-8-azapurine,
2-(1(R)-isopropyl-2-hydroxyethylamino)-6-[N-(2-(3,4-dihydroxyphenyl)ethyl)-N-methyl]amino-9-isopropyl-8-azapurine,
2-(1(R)-isopropyl-2-hydroxyethylamino)-6-[N-(2-(3,4-dihydroxyphenyl)ethyl)-N-methyl]amino-9-methyl-8-azapurine,
2-(1(R)-isopropyl-2-hydroxyethylamino)-6-[N-(2-(3,4-dihydroxyphenyl)ethyl)-N-methyl]amino-9-ethyl-8-azapurine,
2-(1(R)-isopropyl-2-hydroxyethylamino)-6-[(R)-(1-phenyl-2-hydroxyethyl)amino]-9-isopropyl-8-azapurine,
2-(1(R)-isopropyl-2-hydroxyethylamino)-6-[(R)-(1-phenyl-2-hydroxyethyl)amino]-9-methyl-8-azapurine,
2-(1(R)-isopropyl-2-hydroxyethylamino)-6-[(R)-(1-phenyl-2-hydroxyethyl)amino]-9-ethyl-8-azapurine,
2-(1(R)-isopropyl-2-hydroxyethylamino)-6-[(R,S)-(1-phenyl-2-hydroxyethyl)amino]-9-isopropyl-8-azapurine,
2-(1(R)-isopropyl-2-hydroxyethylamino)-6-[(R,S)-(1-phenyl-2-hydroxyethyl)amino]-9-methyl-8-azapurine,
2-(1(R)-isopropyl-2-hydroxyethylamino)-6-[(R,S)-(1-phenyl-2-hydroxyethyl)amino]-9-ethyl-8-azapurine,
2-chloro-6-[(R,S)-(1-phenyl-2-hydroxyethyl)amino]-9-isopropyl-8-azapurine,
2-chloro-6-[(R,S)-(1-phenyl-2-hydroxyethyl)amino]-9-methyl-8-azapurine,
2-chloro-6-[(R,S)-(1-phenyl-2-hydroxyethyl)amino]-9-ethyl-8-azapurine,
2-[1-(hydroxymethyl)propylamino]-6-benzylamino-9-isopropyl-8-azapurine,
2-[1-(hydroxymethyl)propylamino]-6-benzylamino-9-methyl-8-azapurine,
2-[1-(hydroxymethyl)propylamino]-6-benzylamino-9-ethyl-8-azapurine,
2-(2-aminopropylamino)-6-benzylamino-9-isopropyl-8-azapurine,
2-(2-aminopropylamino)-6-benzylamino-9-methyl-8-azapurine,
2-(2-aminopropylamino)-6-benzylamino-9-ethyl-8-azapurine,
2-(2-hydroxypropylamino)-6-benzylamino-9-isopropyl-8-azapurine,
2-(2-hydroxypropylamino)-6-benzylamino-9-methyl-8-azapurine,
2-(2-hydroxypropylamino)-6-benzylamino-9-ethyl-8-azapurine,
2-(2-diethylamino)-6-(4-methoxybenzylamino)-9-isopropyl-8-azapurine,
2-(2-diethylamino)-6-(4-methoxybenzylamino)-9-methyl-8-azapurine,
2-(2-diethylamino)-6-(4-methoxybenzylamino)-9-ethyl-8-azapurine,
2-(1(R)-isopropyl-2-hydroxyethylamino)-6-(3-chloro-4-carboxyanilino)-9-isopropyl-8-azapurine,
2-(1(R)-isopropyl-2-hydroxyethylamino)-6-(3-chloro-4-carboxyanilino)-9-methyl-8-azapurine,
2-(1(R)-isopropyl-2-hydroxyethylamino)-6-(3-chloro-4-carboxyanilino)-9-ethyl-8-azapurine,
2-(1(R)-isopropyl-2-hydroxyethylamino)-6-benzylamino-9-isopropyl-8-azapurine,
2-(1(R)-isopropyl-2-hydroxyethylamino)-6-benzylamino-9-methyl-8-azapurine,
2-(1(R)-isopropyl-2-hydroxyethylamino)-6-benzylamino-9-ethyl-8-azapurine, 2-(1(R)-isopropyl-2-hydroxyethylamino)-6-(3-chloroanilino)-9-isopropyl-8-azapurine,
2-(1(R)-isopropyl-2-hydroxyethylamino)-6-(3-chloroanilino)-9-methyl-8-azapurine, and
2-(1(R)-isopropyl-2-hydroxyethylamino)-6-(3-chloroanilino)-9-ethyl-8-azapurine.

4. A compound according to claim 1 which has the (R) or (S) configuration in R2, R6, or R9.

5. A compound according to claim 1 which has the (R) configuration in R2, R6, or R9.

6. A compound according to claim 1 which has the (S) configuration in R2, R6, or R9.

7. A pharmaceutical composition comprising a compound according to claim 1, or a pharmaceutically acceptable salt thereof, together with a pharmaceutically acceptable carrier, diluent or excipient.

8. A compound selected from
2-[1-(hydroxymethyl)propylamino]-6-benzylamino-8-azapurine,
2-[((R)-2-hydroxymethyl)pyrrolidine-1-yl)]-6-benzylamino-8-azapurine,
2-(2-aminopropylamino)-6-benzylamino-8-azapurine,
2-(2-hydroxypropylamino)-6-benzylamino-8-azapurine,
2-(1(R)-isopropyl-2-hydroxyethylamino)-6-benzylamino-8-azapurine,
2-(2-aminocyclohexylamino)-6-benzylamino-8-azapurine,
2-[1-(hydroxymethyl)propylamino]-6-(3-acetoxybenzylamino)-8-azapurine,
2-[(R)-2-(hydroxymethyl)pyrrolidine-1-yl]-6-(3-acetoxybenzylamino)-8-azapurine,
2-(2-aminopropylamino)-6-(3-acetoxybenzylamino)-8-azapurine,
2-(2-hydroxypropylamino)-6-(3-acetoxybenzylamino)-8-azapurine,
2-(1(R)-isopropyl-2-hydroxyethylamino)-6-(3-acetoxybenzylamino)-8-azapurine,
2-(4-aminocyclohexylamino)-6-(3-acetoxybenzylamino)-8-azapurine,
2-(2-aminocyclohexylamino)-6-(3-acetoxybenzylamino)-8-azapurine,
2-[1-(hydroxymethyl)propylamino]-6-(2-hydroxy-3-methoxybenzylamino)-8-azapurine,
2-[(R)-2-(hydroxymethyl)pyrrolidine-1-yl]-6-(2-hydroxy-3-methoxybenzylamino)-8-azapurine,
2-(2-aminopropylamino)-6-(2-hydroxy-3-methoxybenzylamino)-8-azapurine,
2-(2-hydroxypropylamino)-6-(2-hydroxy-3-methoxybenzylamino)-8-azapurine,
2-(1(R)-isopropyl-2-hydroxyethylamino)-6-(2-hydroxy-3-methoxybenzylamino)-8-azapurine,
2-(4-aminocyclohexylamino)-6-(2-hydroxy-3-methoxybenzylamino)-8-azapurine,
2-(2-aminocyclohexylamino)-6-(2-hydroxy-3-methoxybenzylamino)-8-azapurine,
2-[1-(hydroxymethyl)propylamino]-6-(2,3-dihydroxy-4-methoxybenzylamino)-8-azapurine,
2-((R)-2-(hydroxymethyl)pyrrolidine-1-yl)-6-(2,3-dihydroxy-4-methoxybenzylamino)-8-azapurine,
2-(2-aminopropylamino)-6-(2,3-dihydroxy-4-methoxybenzylamino)-8-azapurine,
2-(2-hydroxypropylamino)-6-(2,3-dihydroxy-4-methoxybenzylamino)-8-azapurine,
2-(1(R)-isopropyl-2-hydroxyethylamino)-6-(2,3-dihydroxy-4-methoxybenzylamino)-8-azapurine,
2-(4-aminocyclohexylamino)-6-(2,3-dihydroxy-4-methoxybenzylamino)-8-azapurine,
2-(2-aminocyclohexylamino)-6-(2,3-dihydroxy-4-methoxybenzylamino)-8-azapurine,
2-[1-(hydroxymethyl)propylamino]-6-(2,5-dihydroxy-4-methoxybenzylamino)-8-azapurine,
2-[(R)-2-(hydroxymethyl)pyrrolidine-1-yl]-6-(2,5-dihydroxy-4-methoxybenzylamino)-8-azapurine,
2-(2-aminopropylamino)-6-(2,5-dihydroxy-4-methoxybenzylamino)-8-azapurine,
2-(2-hydroxypropylamino)-6-(2,5-dihydroxy-4-methoxybenzylamino)-8-azapurine,
2-(1(R)-isopropyl-2-hydroxyethylamino)-6-(2,5-dihydroxy-4-methoxybenzylamino)-8-azapurine,
2-(4-aminocyclohexylamino)-6-(2,5-dihydroxy-4-methoxybenzylamino)-8-azapurine,
2-(2-aminocyclohexylamino)-6-(2,5-dihydroxy-4-methoxybenzylamino)-8-azapurine,
2-[1-(hydroxymethyl)propylamino]-6-(2,6-dihydroxy-4-methoxybenzylamino)-8-azapurine,
2-[(R)-2-(hydroxymethyl)pyrrolidine-1-yl]-6-(2,6-dihydroxy-4-methoxybenzylamino)-8-azapurine,
2-(2-aminopropylamino)-6-(2,6-dihydroxy-4-methoxybenzylamino)-8-azapurine,
2-(2-hydroxypropylamino)-6-(2,6-dihydroxy-4-methoxybenzylamino)-8-azapurine,
2-(1(R)-isopropyl-2-hydroxyethylamino)-6-(2,6-dihydroxy-4-methoxybenzylamino)-8-azapurine,
2-(4-aminocyclohexylamino)-6-(2,6-dihydroxy-4-methoxybenzylamino)-8-azapurine,
2-(2-aminocyclohexylamino)-6-(2,6-dihydroxy-4-methoxybenzylamino)-8-azapurine,
2-[1-(hydroxymethyl)propylamino]-6-(2,3-dihydroxy-4-chlorobenzylamino)-8-azapurine,
2-[(R)-2-(hydroxymethyl)pyrrolidine-1-yl]-6-(2,3-dihydroxy-4-chlorobenzylamino)-8-azapurine,
2-(2-aminopropylamino)-6-(2,3-dihydroxy-4-chlorobenzylamino)-8-azapurine,
2-(2-hydroxypropylamino)-6-(2,3-dihydroxy-4-chlorobenzylamino)-8-azapurine,
2-(1(R)-isopropyl-2-hydroxyethylamino)-6-(2,3-dihydroxy-4-chlorobenzylamino)-8-azapurine,
2-(4-aminocyclohexylamino)-6-(2,3-dihydroxy-4-chlorobenzylamino)-8-azapurine,
2-(2-aminocyclohexylamino)-6-(2,3-dihydroxy-4-chlorobenzylamino)-8-azapurine,
2-[1-(hydroxymethyl)propylamino]-6-(2,5-dihydroxy-4-chlorobenzylamino)-8-azapurine,
2-[(R)-2-(hydroxymethyl)pyrrolidine-1-yl]-dihydroxy-4-chlorobenzylamino)-8-azapurine,
2-(2-aminopropylamino)-6-(2,5-dihydroxy-4-chlorobenzylamino)-8-azapurine,
2-(2-hydroxypropylamino)-6-(2,5-dihydroxy-4-chlorobenzylamino)-8-azapurine,
2-(1(R)-isopropyl-2-hydroxyethylamino)-6-(2,5-dihydroxy-4-chlorobenzylamino)-8-azapurine,
2-(4-aminocyclohexylamino)-6-(2,5-dihydroxy-4-chlorobenzylamino)-8-azapurine,
2-[1-(hydroxymethyl)propylamino]-6-(2,6-dihydroxy-4-chlorobenzylamino)-8-azapurine,
2-[(R)-2-(hydroxymethyl)pyrrolidine-1-yl]-6-(2,6-dihydroxy-4-chlorobenzylamino)-8-azapurine,
2-(2-aminopropylamino)-6-(2,6-dihydroxy-4-chlorobenzylamino)-8-azapurine,
2-(2-hydroxypropylamino)-6-(2,6-dihydroxy-4-chlorobenzylamino)-8-azapurine,
2-(1(R)-isopropyl-2-hydroxyethylamino)-6-(2,6-dihydroxy-4-chlorobenzylamino)-8-azapurine, 2-(4-aminocyclohexylamino)-6-(2,6-dihydroxy-4-chlorobenzylamino)-8-azapurine,
2-(2-aminocyclohexylamino)-6-(2,6-dihydroxy-4-chlorobenzylamino)-8-azapurine,
2-(2-aminocyclohexylamino)-6-(2,6-dihydroxy-4-chlorobenzylamino)-8-azapurine,
2-[1-(hydroxymethyl)propylamino]-6-(2-acetoxybenzylamino)-8-azapurine,
2-[(R)-2-(hydroxymethyl)pyrrolidine-1-yl]-6-(2-acetoxybenzylamino)-8-azapurine,
2-(2-aminopropylamino)-6-(2-acetoxybenzylamino)-8-azapurine,
2-(2-hydroxypropylamino)-6-(2-acetoxybenzylamino)-8-azapurine,
2-(1(R)-isopropyl-2-hydroxyethylamino)-6-(2-acetoxybenzylamino)-8-azapurine,
2-(4-aminocyclohexylamino)-6-(2-acetoxybenzylamino)-8-azapurine,
2-(2-aminocyclohexylamino)-6-(2-acetoxybenzylamino)-8-azapurine,
2-[1-(hydroxymethyl)propylamino]-6-(2-aminobenzylamino)-8-azapurine,
2-[(R)-2-(hydroxymethyl)pyrrolidine-1-yl]-6-(2-aminobenzylamino)-8-azapurine,
2-(2-aminopropylamino)-6-(2-aminobenzylamino)-8-azapurine,
2-(2-hydroxypropylamino)-6-(2-aminobenzylamino)-8-azapurine,
2-(1(R)-isopropyl-2-hydroxyethylamino)-6-(2-aminobenzylamino)-8-azapurine,
2-(4-aminocyclohexylamino)-6-(2-aminobenzylamino)-8-azapurine,
2-(2-aminocyclohexylamino)-6-(2-aminobenzylamino)-8-azapurine,
2-[1-(hydroxymethyl)propylamino]-6-(2-amino-6-chlorobenzylamino)-8-azapurine,
2-[(R)2-(hydroxymethyl)pyrrolidine-1-yl]-6-(2-amino-6-chlorobenzylamino)-8-azapurine,
2-(2-aminopropylamino)-6-(2-amino-6-chlorobenzylamino)-8-azapurine,
2-(2-hydroxypropylamino)-6-(2-amino-6-chlorobenzylamino)-8-azapurine,
2-(1(R)-isopropyl-2-hydroxyethylamino)-6-(2-amino-6-chlorobenzylamino)-8-azapurine,
2-(4-aminocyclohexylamino)-6-(2-amino-6-chlorobenzylamino)-8-azapurine,
2-(2-aminocyclohexylamino)-6-(2-amino-6-chlorobenzylamino)-8-azapurine,
2-[1-(hydroxymethyl)propylamino]-6-(3-amino-4-chlorobenzylamino)-8-azapurine,
2-(2-aminopropylamino)-6-(3-amino-4-chlorobenzylamino)-8-azapurine,
2-(2-hydroxypropylamino)-6-(3-amino-4-chlorobenzylamino)-8-azapurine,
2-(1(R)-isopropyl-2-hydroxyethylamino)-6-(3-amino-4-chlorobenzylamino)-8-azapurine,
2-(4-aminocyclohexylamino)-6-(3-amino-4-chlorobenzylamino)-8-azapurine,
2-(2-aminocyclohexylamino)-6-(3-amino-4-chlorobenzylamino)-8-azapurine,
2-[1-(hydroxymethyl)propylamino]-6-(3-acetylbenzylamino)-8-azapurine,
2-(2-aminopropylamino)-6-(3-acetylbenzylamino)-8-azapurine,
2-(2-hydroxypropylamino)-6-(3-acetylbenzylamino)-8-azapurine,
2-(1(R)-isopropyl-2-hydroxyethylamino)-6-(3-acetylbenzylamino)-8-azapurine,
2-(4-aminocyclohexylamino)-6-(3-acetylbenzylamino)-8-azapurine,
2-(2-aminocyclohexylamino)-6-(3-acetylbenzylamino)-8-azapurine,
2-[1-(hydroxymethyl)propylamino]-6-(2-acetylbenzylamino)-8-azapurine,
2-[(R)-2-(hydroxymethyl)pyrrolidine-1-yl]-6-(2-acetylbenzylamino)-8-azapurine,
2-(2-aminopropylamino)-6-(2-acetylbenzylamino)-8-azapurine,
2-(2-hydroxypropylamino)-6-(2-acetylbenzylamino)-8-azapurine,
2-(1(R)-isopropyl-2-hydroxyethylamino)-6-(2-acetylbenzylamino)-8-azapurine,
2-(4-aminocyclohexylamino)-6-(2-acetylbenzylamino)-8-azapurine,
2-(2-aminocyclohexylamino)-6-(2-acetylbenzylamino)-8-azapurine,
2-[1-(hydroxymethyl)propylamino]-6-anilino-8-azapurine,
2-[(R)-2-(hydroxymethyl)pyrrolidine-1-yl]-6-anilino-8-azapurine,
2-(2-aminopropylamino)-6-anilino-8-azapurine,
2-(2-hydroxypropylamino)-6-anilino-8-azapurine,
2-(1(R)-isopropyl-2-hydroxyethylamino)-6-anilino-8-azapurine,
2-(4-aminocyclohexylamino)-6-anilino-8-azapurine,
2-(2-aminocyclohexylamino)-6-anilino-8-azapurine,
2-[1-(hydroxymethyl)propylamino]-6-(3-chloroanilino)-8-azapurine,
2-[(R)-2-(hydroxymethyl)pyrrolidine-1-yl]-6-(3-chloroanilino)-8-azapurine,
2-(2-aminopropylamino)-6-(3-chloroanilino)-8-azapurine,
2-(2-hydroxypropylamino)-6-(3-chloroanilino)-8-azapurine,
2-(1(R)-isopropyl-2-hydroxyethylamino)-6-(3-chloroanilino)-8-azapurine,
2-(4-aminocyclohexylamino)-6-(3-chloroanilino)-8-azapurine,
2-(2-aminocyclohexylamino)-6-(3-chloroanilino)-8-azapurine,
2-[1-(hydroxymethyl)propylamino]-6-(4-chloroanilino)-8-azapurine,
2-[(R)(2-hydroxymethyl)pyrrolidine-1-yl]-6-(4-chloroanilino)-8-azapurine,
2-(2-aminopropylamino)-6-(4-chloroanilino)-8-azapurine,
2-(2-hydroxypropylamino)-6-(4-chloroanilino)-8-azapurine,
2-(1(R)-isopropyl-2-hydroxyethylamino)-6-(4-chloroanilino)-8-azapurine,
2-(4-aminocyclohexylamino)-6-(4-chloroanilino)-8-azapurine,
2-(2-aminocyclohexylamino)-6-(4-chloroanilino)-8-azapurine,
2-[1-(hydroxymethyl)propylamino]-6-(4-bromoanilino)-8-azapurine,
2-[(R)-2-(hydroxymethyl)pyrrolidine-1-yl]-6-(4-bromoanilino)-8-azapurine,
2-(2-aminopropylamino)-6-(4-bromoanilino)-8-azapurine,
2-(2-hydroxypropylamino)-6-(4-bromoanilino)-8-azapurine, 2-(1(R)-isopropyl-2-hydroxyethylamino)-6-(4-bromoanilino)-8-azapurine,
2-(4-aminocyclohexylamino)-6-(4-bromoanilino)-8-azapurine,
2-(2-aminocyclohexylamino)-6-(4-bromoanilino)-8-azapurine,
2-[1-(hydroxymethyl)propylamino-6-(3-chloro-5-aminoanilino)-8-azapurine,
2-[(R)-2-(hydroxymethyl)pyrrolidine-1-yl]-6-(3-chloro-5-aminoanilino)-8-azapurine,
2-(2-aminopropylamino)-6-(3-chloro-5-aminoanilino)-8-azapurine,
2-(2-hydroxypropylamino)-6-(3-chloro-5-aminoanilino)-8-azapurine,
2-(1(R)-isopropyl-2-hydroxyethylamino)-6-(3-chloro-5-aminoanilino)-8-azapurine,
2-(4-aminocyclohexylamino)-6-(3-chloro-5-aminoanilino)-8-azapurine,
2-(2-aminocyclohexylamino)-6-(3-chloro-5-aminoanilino)-8-azapurine,
2-[1-(hydroxymethyl)propylamino]-6-(3-chloro-4-carboxyanilino)-8-azapurine,
2-[(R)-2-(hydroxymethyl)pyrrolidine-1-yl]-6-(3-chloro-4-carboxyanilino)-8-azapurine,
2-(2-aminopropylamino)-6-(3-chloro-4-carboxyanilino)-8-azapurine,
2-(2-hydroxypropylamino)-6-(3-chloro-4-carboxyanilino)-8-azapurine,
2-(1(R)-isopropyl-2-hydroxyethylamino)-6-(3-chloro-4-carboxyanilino)-8-azapurine,
2-(4-aminocyclohexylamino)-6-(3-chloro-4-carboxyanilino)-8-azapurine,
2-(2-aminocyclohexylamino)-6-(3-chloro-4-carboxyanilino)-8-azapurine,
2-[1-(hydroxymethyl)propylamino]-6-(3-carboxy-4-chloroanilino)-8-azapurine,
2-[(R)-2-(hydroxymethyl)pyrrolidine-1-yl]-6-(3-carboxy-4-chloroanilino)-8-azapurine,
2-(2-aminopropylamino)-6-(3-carboxy-4-chloroanilino)-8-azapurine,
2-(2-hydroxypropylamino)-6-(3-carboxy-4-chloroanilino)-8-azapurine,
2-(1(R)-isopropyl-2-hydroxyethylamino)-6-(3-carboxy-4-chloroanilino)-8-azapurine,
2-(4-aminocyclohexylamino)-6-(3-carboxy-4-carboxyanilino)-8-azapurine,
2-(2-aminocyclohexylamino)-6-(3-carboxy-4-chloroanilino)-8-azapurine,
2-[1-(hydroxymethyl)propylamino]-6-(3-amino-4-chloroanilino)-8-azapurine,
2-[(R)2-(hydroxymethyl)pyrrolidine-1-yl]-6-(3-amino-4-chloroanilino)-8-azapurine,
2-(2-aminopropylamino)-6-(3-amino-4-chloroanilino)-8-azapurine,
2-(2-hydroxypropylamino)-6-(3-amino-4-chloroanilino)-8-azapurine,
2-(1(R)-isopropyl-2-hydroxyethylamino)-6-(3-amino-4-chloroanilino)-8-azapurine,
2-(4-aminocyclohexylamino)-6-(3-amino-4-chloroanilino)-8-azapurine,
2-(2-aminocyclohexylamino)-6-(3-amino-4-chloroanilino)-8-azapurine,
2-[1-(hydroxymethyl)propylamino]-6-(3-chloro-4-aminoanilino)-8-azapurine,
2-[(R)2-(hydroxymethyl)pyrrolidine-1-yl]-6-(3-chloro-4-aminoanilino)-8-azapurine,
2-(2-aminopropylamino)-6-(3-chloro-4-aminoanilino)-8-azapurine,
2-(2-hydroxypropylamino)-6-(3-chloro-4-aminoanilino)-8-azapurine,
2-(1(R)-isopropyl-2-hydroxyethylamino)-6-(3-chloro-4-aminoanilino)-8-azapurine,
2-(4-aminocyclohexylamino)-6-(3-chloro-4-aminoanilino)-8-azapurine,
2-(2-aminocyclohexylamino)-6-(3-chloro-4-aminoanilino)-8-azapurine,
2-[1-(hydroxymethyl)propylamino]-6-(3-carboxy-4-hydroxyanilino)-8-azapurine,
2-[(R)2-(hydroxymethyl)pyrrolidine-1-yl]-6-(3-carboxy-4-hydroxyanilino)-8-azapurine,
2-(2-aminopropylamino)-6-(3-carboxy-4-hydroxyanilino)-8-azapurine,
2-(2-hydroxypropylamino)-6-(3-carboxy-4-hydroxyanilino)-8-azapurine,
2-(1(R)-isopropyl-2-hydroxyethylamino)-6-(3-carboxy-4-hydroxyanilino)-8-azapurine,
2-(4-aminocyclohexylamino)-6-(3-carboxy-4-hydroxyanilino)-8-azapurine,
2-(2-aminocyclohexylamino)-6-(3-carboxy-4-hydroxyanilino)-8-azapurine,
2-(2-hydroxypropylamino)-6-[N-(3,4-dihydroxybenzyl)-N-methyl]amino-8-azapurine,
2-(1(R)-isopropyl-2-hydroxyethylamino)-6-[N-(3,4-dihydroxybenzyl)-N-methyl]amino-8-azapurine,
2-(2-hydroxypropylamino)-6-[1-(3,4-dihydroxyphenyl)ethyl]amino-8-azapurine,
2-(1(R)-isopropyl-2-hydroxyethylamino)-6-[1-(3,4-dihydroxyphenyl)ethyl]amino-8-azapurine,
2-(1(R)-isopropyl-2-hydroxyethylamino)-6-[N-(2-(3,4-dihydroxyphenyl)ethyl)-N-methyl]amino-8-azapurine,
2-(1(R)-isopropyl-2-hydroxyethylamino)-6-[(R)-(1-phenyl-2-hydroxyethyl)amino]-8-azapurine,
2-(1(R)-isopropyl-2-hydroxyethylamino)-6-[(R,S)-(1-phenyl-2-hydroxyethyl)amino]-8-azapurine,
2-chloro-6-[(R,S)-(1-phenyl-2-hydroxyethyl)amino]-8-azapurine,
2-[1-(hydroxymethyl)propylamino]-6-benzylamino-8-azapurine,
2-(2-aminopropylamino)-6-benzylamino-8-azapurine,
2-(2-hydroxypropylamino)-6-benzylamino-8-azapurine,
2-(2-diethylamino)-6-(4-methoxybenzylamino)-8-azapurine,
2-(2-hydroxypropylamino)-6-(3-chloroanilino)-8-azapurine,
2-(2-hydroxypropylamino)-6-(3-chloro-4-carboxyanilino)-8-azapurine,
2-[(R)-(2-(hydroxymethyl)propyrrolidin-1-yl]-6-benzylamino-8-azapurine,
2-(1(R)-isopropyl-2-hydroxyethylamino)-6-(3-chloro-4-carboxyanilino)-8-azapurine,
2-(1(R)-isopropyl-2-hydroxyethylamino)-6-benzylamino-8-azapurine,
2-(1(R)-isopropyl-2-hydroxyethylamino)-6-(3-chloroanilino)-8-azapurine,
6-benzylamino-2-(3-nitrobenzylamino)-8-azapurine,
6-benzylamino-2-(4-nitrobenzylamino) 8-azapurine,
2-(3-aminobenzylamino)-6-benzylamino-8-azapurine,
2-(4-aminobenzylamino)-6-benzylamino-8-azapurine,
6-benzylamino-2-(3-sulfamoylphenylamino)-8-azapurine,
6-benzylamino-2-(4-sulfamoylphenylamino)-8-azapurine, 6-benzylamino-2-(3-sulfamoylbenzylamino)-8-azapurine,
6-benzylamino-2-(4-sulfamoylbenzylamino)-8-azapurine,
6-benzylamino-2-(3-ureidopropylamino)-8-azapurine,
6-benzylamino-2-(2-ureidoethylamino)-8-azapurine,
6-benzylamino-2-(3-guanidinopropyl)-8-azapurine,
6-benzylamino-2-(2-guanidinoethyl)-8-azapurine,
2-benzylamino-6-(3-nitrobenzylamino)-8-azapurine,
2-benzylamino-6-(4-nitrobenzylamino)-8-azapurine,
6-(3-aminobenzylamino)-2-benzylamino-8-azapurine,
6-(4-aminobenzylamino)-2-benzylamino-8-azapurine,
2-benzylamino-6-(3-sulfamoylphenylamino)-8-azapurine,
2-benzylamino-6-(4-sulfamoylphenylamino)-8-azapurine,
2-benzylamino-6-(3-sulfamoylbenzylamino)-8-azapurine,
2-benzylamino-6-(4-sulfamoylbenzylamino)-8-azapurine,
2-benzylamino-6-(3-ureidopropylamino)-8-azapurine,
2-benzylamino-6-(2-ureidoethylamino)-8-azapurine,
2-benzylamino-6-(3-guanidinopropyl)-8-azapurine, and
2-benzylamino-6-(2-guanidinoethyl)-8-azapurine.

* * * * *